US011850449B2

(12) United States Patent
Safavi-Naeini et al.

(10) Patent No.: US 11,850,449 B2
(45) Date of Patent: Dec. 26, 2023

(54) IRRADIATION METHOD AND SYSTEM

(71) Applicants: Australian Nuclear Science and Technology Organisation, Lucas Heights (AU); University of Wollongong, Wollongong (AU)

(72) Inventors: Mitra Safavi-Naeini, Stanwell Park (AU); Andrew Stephen Chacon, Minto (AU)

(73) Assignees: Australian Nuclear Science and Technology Organisation, Lucas Heights (AU); University of Wollongong, Wollongong (AU)

( * ) Notice: Subject to any disclaimer, the term of this patent is extended or adjusted under 35 U.S.C. 154(b) by 718 days.

(21) Appl. No.: 16/644,368

(22) PCT Filed: Sep. 14, 2018

(86) PCT No.: PCT/AU2018/051006
§ 371 (c)(1),
(2) Date: Mar. 4, 2020

(87) PCT Pub. No.: WO2019/051557
PCT Pub. Date: Mar. 21, 2019

(65) Prior Publication Data
US 2020/0197730 A1  Jun. 25, 2020

(30) Foreign Application Priority Data

Sep. 14, 2017 (AU) .................. 2017903739

(51) Int. Cl.
*A61N 5/10* (2006.01)
*H05H 7/10* (2006.01)
(Continued)

(52) U.S. Cl.
CPC ......... *A61N 5/1078* (2013.01); *A61N 5/1065* (2013.01); *G21K 5/04* (2013.01);
(Continued)

(58) Field of Classification Search
CPC .... A61N 2005/1087; A61N 2005/1095; A61N 2005/1096; A61N 5/1043; A61N 5/107;
(Continued)

(56) References Cited

U.S. PATENT DOCUMENTS 7,579,603 B2 * 8/2009 Birgy .................. A61N 5/1079
250/492.1
9,636,525 B1 5/2017 Sahadevan
(Continued)

FOREIGN PATENT DOCUMENTS

CN 104511096 A 4/2015
EP 1658878 A1 5/2006
(Continued)

OTHER PUBLICATIONS

Gavin, Patrick R. et al., "Large Animal Normal Tissue Tolerance with Boron Neutron Capture" Int. J. Radiation Oncology Biol. Phys., 1994, pp. 1099-1106, vol. 28, No. 5.
(Continued)

*Primary Examiner* — Thaddeus B Cox
*Assistant Examiner* — Marc D. Honrath
(74) *Attorney, Agent, or Firm* — Knobbe, Martens, Olson & Bear LLP

(57) ABSTRACT

An irradiation method and system for irradiating a target volume, the method comprising: providing thermal neutron absorbing nuclides (such as in the form of a high neutron cross-section agent) at the target volume; and producing neutrons by irradiating nuclei in or adjacent to the target volume with a beam of particles consisting of any one or more of protons, deuterons, tritons and heavy ions, thereby
(Continued)

prompting production of the neutrons through non-elastic collisions between the atoms in the path of the beam (including the target) and the particles. The neutron absorbing nuclides absorb neutrons produced in the non-elastic collisions, thereby producing capture products or fragments that irradiate the target volume.

26 Claims, 39 Drawing Sheets

(51) Int. Cl.
H05H 13/04 (2006.01)
H05H 13/10 (2006.01)
G21K 5/04 (2006.01)
(52) U.S. Cl.
CPC .............. *H05H 7/10* (2013.01); *H05H 13/04* (2013.01); *H05H 13/10* (2013.01); *A61N 2005/109* (2013.01); *A61N 2005/1034* (2013.01); *A61N 2005/1087* (2013.01); *A61N 2005/1098* (2013.01)
(58) Field of Classification Search
CPC ...... A61N 5/1071; A61N 5/1081; G21K 1/10; H05H 2007/004; H05H 2007/125; H05H 7/12
See application file for complete search history.

(56) References Cited

U.S. PATENT DOCUMENTS

| 10,004,805 | B2* | 6/2018 | Chen ................. A61K 41/0095 |
| 2007/0108922 | A1 | 5/2007 | Amaldi |
| 2016/0074512 | A1 | 3/2016 | Chen |
| 2017/0062086 | A1 | 3/2017 | Park, Jr. et al. |
| 2018/0161602 | A1* | 6/2018 | Kawrykow ............ G21K 1/046 |

FOREIGN PATENT DOCUMENTS

| EP | 1895819 A1 | 8/2006 |
| EP | 2979728 A1 | 2/2016 |
| EP | 3133905 A1 | 2/2017 |
| JP | 2014021078 A * | 2/2014 |
| JP | 2017-96672 A | 6/2017 |
| WO | WO 00/15298 A1 | 3/2000 |

OTHER PUBLICATIONS

Karg, Juergen et al., "The Monte Carlo code MCPTV-Monte Carlo dose calculation in radiation therapy with carbon ions" Phys. Med. Biol., 2010, pp. 3917-3936, vol. 55.
Supplementary European Search Report for EP 18856248 dated Apr. 20, 2021.
Xinchen, Sun et al., "IV.Proton and heavy ion therapy—1. Physical and Biological Characteristics of Proton Rays" Oncology Radiation Therapy Technology, Sep. 30, 2015.
Second Office Action for CN 201880069367.5 dated Mar. 15, 2022.
Agostinelli, S. et al., "Geant4-a simulation toolkit" Nuclear Instruments and Methods in Physics Research, 2003, pp. 250-303, vol. 506.
Alkins, Ryan D. et al., "Enhancing drug delivery for boron neutron capture therapy of brain tumors with focused ultrasound" Neuro-Oncology, 2013, pp. 1225-1235, vol. 15, No. 9.
Allison, J. et al., "Geant4 Developments and Applications" IEEE Transactions on Nuclear Science, Feb. 2006, pp. 270-278, vol. 53, No. 1.
Arcangeli, Stefano et al., ""Hit the primary": A paradigm shift in the treatment of metastatic prostate cancer?" Critical Reviews in Oncology/Hematology, 2016, pp. 231-237, vol. 97.
Barth, Rolf F. et al., "Boron Neutron Capture Therapy of Cancer: Current Status and Future Prospects" Clin Cancer Res., 2005, pp. 3987-4002, vol. 11.
Barth, Rolf F. et al., "Current status of boron neutron capture therapy of high grade gliomas and recurrent head and neck cancer" Radiation Oncology, 2012, pp. 1-21, vol. 7, No. 146.
Battistoni, G. et al., "Nuclear physics and particle therapy" Advances in Physics: X, 2016, pp. 661-686, vol. 1, No. 4.
Blanchard, Pierre et al., "Toward a model-based patient selection strategy for proton therapy: External validation of photon-derived normal tissue complication probability models in a head and neck proton therapy cohort" Radiotherapy and Oncology, 2016, pp. 381-386, vol. 121.
Capala, J. et al., "A Treatment Planning Comparison of BPA- or BSH-based BNCT of Malignant Gliomas" Tech. Rep. BNL-64626, Medical Department, Brookhaven National Laboratories, 1996.
Cerullo, N. et al., "Progress in the use of gadolinium for NCT" Applied Radiation and Isotopes, 2009, pp. S157-S160, vol. 67.
Coderre, Jeffrey A. et al., "The Radiation Biology of Boron Neutron Capture Therapy" Radiation Research, Jan. 1999, pp. 1-18, vol. 151, No. 1.
Coderre, Jeffrey A. et al., "Boron Neutron Capture Therapy: Cellular Targeting of High Linear Energy Transfer Radiation" Technology in Cancer Research & Treatment, Oct. 2003, pp. 355-375, vol. 2, No. 5.
Crane, Christopher H. "Hypofractionated ablative radiotherapy for locally advanced pancreatic cancer" Journal of Radiation Research, 2016, pp. i53-i57, vol. 57, No. S1.
De Stasio, Gelsomina et al., "Gadolinium in Human Glioblastoma Cells for Gadolinium Neutron Capture Therapy" Cancer Research, May 2001, pp. 4272-4277, vol. 61.
De Stasio, Gelsomina et al., "Motexafin-GadoliniumTaken Up In vitro by at Least 90% of Glioblastoma Cell Nuclei" Clin Cancer Res, Jan. 2006, pp. 206-213, vol. 12, No. 1.
Diaz, Aidnag Z. et al., "Assessment of the results from the phase FII boron neutron capture therapy trials at the Brookhaven National Laboratory from a clinician's point of view" Journal of Neuro-Oncology, 2003, pp. 101-109, vol. 62.
Durante, Marco et al., "Nuclear physics in particle therapy: a review" Reports on Progress in Physics, 2016, pp. 1-59, vol. 79, No. 096702.
Durante, Marco et al., "Charged-particle therapy in cancer: clinical uses and future perspectives" Nature Reviews—Clinical Oncology, Aug. 2017, pp. 483-495, vol. 14.
Fairlie, Ian et al., "RBE and WR values of Auger emitters and low-range beta emitters with particular reference to tritium" Journal of Radiological Protection, 2007, pp. 157-168, vol. 27.
Forouzannia, Afshin et al., "Motexafin gadolinium: a novel radiosensitizer for brain tumors" Expert Rev. Anticancer Ther., 2007, pp. 785-794, vol. 7, No. 6.
Gomez-Iturriaga, Alfonso et al., "Incidence of pain flare following palliative radiotherapy for symptomatic bone metastases: multicenter prospective observational study" BMC Palliative Care, 2015, pp. 1-7, vol. 14, No. 48.
González, Elizabeth Musacchio et al., "An accelerator-based Boron Neutron Capture Therapy (BNCT) facility based on the $^7$Li(p,n)$^7$Be" Nuclear Instruments and Methods in Physics Research, 2017, pp. 148-151, vol. A865.
Grantzau, Trine et al., "Risk of second non-breast cancer after radiotherapy for breast cancer: A systematic review and meta-analysis of 762,468 patients" Radiotherapy and Oncology, 2015, pp. 56-65, vol. 114.
Hong, Theodore S. et al., "Multi-Institutional Phase II Study of High-Dose Hypofractionated Proton Beam Therapy in Patients With Localized, Unresectable Hepatocellular Carcinoma and Intrahepatic Cholangiocarcinoma" Journal of Clinical Oncology, Feb. 2016, pp. 460-468, vol. 34, No. 5.
Hopewell, J.W. et al., "Boron neutron capture therapy for newly diagnosed glioblastoma multiforme: An assessment of clinical potential" Applied Radiation and Isotopes, 2011, pp. 1737-1740, vol. 69.

(56) References Cited

OTHER PUBLICATIONS

Humm, John L. et al., "Dosimtery of Auger-electron-emitting radionuclides: Report No. 3 of AAPM Nuclear Medicine Task Group No. 6ª)" Med. Phys., Dec. 1994, pp. 1901-1915, vol. 21, No. 12.
IAEA-TECDOC-1223 "Current status of neutron capture therapy" International Atomic Energy Agency, May 2001.
IAEA Technical Reports Series No. 461 "Relative Biological Effectiveness in Ion Beam Therapy" International Atomic Energy Agency, 2008.
Ichikawa, Hideki et al., "Gadolinium-loaded chitosan nanoparticles for neutron-capture therapy: Influence of micrometric properties of the nanoparticles on tumor-killing effect" Applied Radiation and Isotopes, 2014, pp. 109-113, vol. 88.
Joensuu, Heikki et al., "Boron neutron capture therapy of brain tumors: clinical trials at the Finnish facility using boronophenylalanine" Journal of Neuro-Oncology, 2003, pp. 123-134, vol. 62.
Kasatov, D. et al., "The accelerator neutron source for boron neutron capture therapy" Journal of Physics: Conference Series, 2016, pp. 1-6, vol. 769, No. 012064.
Laine, Aaron Michael et al., "The Role of Hypofractionated Radiation Therapy with Photons, Protons, and Heavy Ions for Treating Extracranial Lesions" Frontiers in Oncology, Jan. 2016, pp. 1-14, vol. 5, Article 302.
Le, Uyen M. et al., "Long-circulating gadolinium-encapsulated liposomes for potential application in tumor neutron capture therapy" International Journal of Pharmaceutics, 2006, pp. 105-112, vol. 312.
Liauw, Stanley L. et al., "New paradigms and future challenges in Radiation Oncology: An Update of Biological Targets and Technology" Science Translational Medicine, Feb. 2013, pp. 1-32, vol. 5, No. 173.
Luderer, Micah John et al., "Advancements in Tumor Targeting Strategies for Boron Neutron Capture Therapy" Pharm Res, 2015, pp. 2824-2836, vol. 32.
Meyers, Christina A. et al., "Neurocognitive Function and Progression in Patients With Brain Metastases Treated With Whole-Brain Radiation and Motexafin Gadolinium: Results of a Randomized Phase III Trial" Journal of Clinical Oncology, Jan. 2004, pp. 157-165, vol. 22, No. 1.
Michiue, Hiroyuki et al., "The acceleration of boron neutron capture therapy using multi-linked mercaptoundecahydrododecaborate (BSH) fused cell-penetrating peptide" Biomaterials, 2014, pp. 3396-3405, vol. 35.
Miyatake, Shin-Ichi et al., "Boron Neutron Capture Therapy for Malignant Brain Tumors" Neurol Med Chir, 2016, pp. 361-371, vol. 56.
Morris, GM et al., "Boron microlocalization in oral mucosal tissue: implications for boron neutron capture therapy" British Journal of Cancer, 2000, pp. 1764-1771, vol. 82, No. 11.
Morrison, Daniel E. et al., "High mitochondrial accumulation of new gadolinium(III) agents within tumour cells" Chem. Commun., 2014, pp. 2252-2254, vol. 50.
Murray, Louise et al., "Second primary cancers after radiation for prostate cancer: A systematic review of the clinical data and impact of treatment technique" Radiotherapy and Oncology, 2014, pp. 213-228, vol. 110.
Nakamura, Hiroyuki et al., "Development of High Boron Content Liposomes and Their Promising Antitumor Effect for Neutron Capture Therapy" Yakugaku Zasshi, 2013, pp. 1297-1306, vol. 133, No. 12.
Nakamura, Hiroyuki et al., "Antitumor effect of boron nitride nanotubes in combination with thermal neutron irradiation on BNCT" Bioorganic & Medicinal Chemistry Letters, 2015, pp. 172-174, vol. 25.
Park, Seo Hyun et al., "Basics of particle therapy I: physics" Radiation Oncology Journal, 2011, pp. 135-146, vol. 29, No. 3.
Peters, Tanja et al., "Cellular uptake and in vitro antitumor efficacy of composite liposomes for neutron capture therapy" Radiation Oncology, 2015, pp. 1-13, vol. 10, No. 52.
Sauerwein, Wolfgang A.G. et al., "Neutron Capture Therapy— Principles and Applications" 2012.
Suzuki, Minoru et al., "The Effects of Boron Neutron Capture Therapy on Liver Tumors and Normal Hepatocytes in Mice" Jpn. J. Cancer Res., Oct. 2000, pp. 1058-1064, vol. 91.
Suzuki, Minoru et al., "Biodistribution of $^{10}$B in a rat liver tumor model following intra-arterial administration of sodium borocaptate (BSH) / degradable starch microspheres (DSM) emulsion" Applied Radiation and Isotopes, 2004, pp. 933-937, vol. 61.
Suzuki, Minoru et al., "A Preliminary Experimental Study of Boron Neutron Capture Therapy for Malignant Tumors Spreading in Thoracic Cavity" Jpn J Clin Oncol, 2007, pp. 245-249, vol. 37, No. 4.
Thomas, Sayana Rachel et al., "Motexafin gadolinium: a promising radiation sensitizer in brain metastasis" Expert Opinion on Drug Discovery, 2011, pp. 195-203, vol. 6, No. 2.
Tietze, Rainer et al., "Boron containing magnetic nanoparticles for neutron capture therapy—an innovative approach for specifically targeting tumors" Applied Radiation and Isotopes, 2015, pp. 151-155, vol. 106.
Tokumitsu, Hiroyuki et al., "Gadolinium neutron-capture therapy using novel gadopentetic acid-chitosan complex nanoparticles: in vivo growth suppression of experimental melanoma solid tumor" Cancer Letters, 2000, pp. 177-182, vol. 150.
Wambersie, André et al., "A Challenge for High-Precision Radiation Therapy: The Case for Hadrons" Strahlenther Onkol, 1999, pp. 122-128, vol. 175, Suppl. 2.
Yoshioka, M. "Review of Accelerator-based Boron Neutron Capture Therapy Machines" Proceedings of IPAC2016, Busan, Korea— OIST, Okinawa Institute of Science and Technology Graduate University, Onna-son, Japan, pp. 3171-3175.
Zamenhof, R. et al., "Treatment Planning for Neutron Capture Therapy of Glioblastoma Multiforme Using an Epithermal Neutron Beam from the MITR-II Research Reactor and Monte Carlo Simulation" Progress in Neutron Capture Therapy for Cancer, 1992, pp. 173-177.
Zeitlin, Cary et al., "The Role of Nuclear Fragmentation in Particle Therapy and Space Radiation Protection" Frontiers in Oncology, Mar. 2016, pp. 1-13, vol. 6, Article 65.
International Search Report for PCT/AU2018/051006 dated Nov. 26, 2018.

\* cited by examiner

IRRADIATION METHOD AND SYSTEM

CROSS REFERENCE TO RELATED APPLICATIONS

This application is a U.S. National Phase Application of PCT International Application Number PCT/AU2018/051006, filed on Sep. 14, 2018, designating the United States of America and published in the English language, which is an International Application of and claims the benefit of priority to Australian Patent Application No. 2017903739, filed on Sep. 14, 2017. The disclosures of the above-referenced applications are hereby expressly incorporated by reference in their entireties.

FIELD OF THE INVENTION

The invention relates to irradiation method and system, of particular but by no means exclusive application in irradiation of a biological material.

BACKGROUND OF THE INVENTION

The principal aim of all forms of radiation therapy is to deliver the maximum therapeutic radiation dose to the target, while sparing surrounding healthy tissue. One of the greatest challenges of radiotherapy is to minimize its latent effects, including the risk of secondary cancer, which can occur anywhere from five years to many decades post-treatment [1-4]. The objective is to minimize normal tissue complication probability (NTCP), which includes the probability of developing treatment-induced cancers, by maximizing the conformity of the delivered dose to the target volume [4, 5]. Technological advancements in radiotherapy (such as intensity modulated radiotherapy, image-guided radiotherapy and particle therapies) have enabled more accurate and selective targetting of tumours, while the use of radiosensitisers increases the local biological efficacy of the therapeutic dose relative to healthy tissues [6, 7].

Particle (or tadron) therapy is a form of radiotherapy in which a beam of highly energetic protons or heavy ions are used to deliver a therapeutic radiation dose to a treatment region. Monoenergetic beams of protons and heavy ions exhibit a very well-defined Bragg peak with an energy-dependent maximum dose depth, allowing highly conformal dose delivery. This depth-selectivity allows the treatment of deep tissues without delivering a harmful dose to healthy tissues at other depths, making proton/heavy ion therapy a superior treatment option than photon and electron beams [6, 8, 9].

During particle therapy, most of the primary particles in the beam deposit their kinetic energy through multiple electromagnetic interactions. However, a fraction of these particles will undergo non-elastic collisions with nuclei in the target. This results in the production of a range of nuclear fragments at the target site, including short-range, high-LET charged particles and neutrons which are emitted more or less isotropically from the point of collision, and which deposit their energy in the region surrounding the path of the incident ion beam [10, 11]. Unfortunately, these fragments irradiate both target and non-target tissues indiscriminately, including depositing a fraction of the beam's kinetic energy outside the target volume [9, 12]. Such interactions are typically regarded as a nuisance, in particular when they occur outside of the treatment region, as their existence undermines one of the main advantages of particle therapy—that is, the large peak-to-plateau dose ratio.

Light water, the principal constituent of human tissue, has a moderate thermal neutron cross-section (0.335 barns), which can be greatly increased by the administration of agents containing isotopes such as $^{10}B$ or $^{157}Gd$ with very high neutron cross sections (3838 and 254000 barns, respectively). Non-elastic thermal neutron interactions with water primarily result in hydrogen capture of the neutron and the release of a high-energy gamma photon, but non-elastic thermal neutron interactions with $^{10}B$ or $^{157}Gd$ result in the production of energetic charged particles with high relative biological effectiveness (RBE): this is the basic operating principle of neutron capture therapy (NCT).

In NCT, the biological dose due to the presence of the capture agent depends on the physical dose (which, in turn, depends on the concentration of neutron capture agent), together with the relative biological effectiveness (RBE) of the secondary particles as determined by the specific NCA. The latter factor varies significantly between different cell types and context (i.e., in vitro versus in vivo); it is also specific to each specific neutron capture agent. In BNCT literature this compound-specific RBE factor is commonly referred to as 'compound biological effectiveness' (CBE), though most researchers working with gadolinium simply refer to it as RBE.

In the case of $^{10}B$, the capture mechanism results in the production of several high LET products [15]:

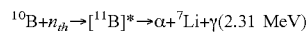
$$^{10}B + n_{th} \rightarrow [^{11}B]^* \rightarrow \alpha + ^{7}Li + \gamma (2.31 \text{ MeV})$$

Both the alpha particles and the lithium ions are high LET particles that produce closely spaced ionizations in the immediate vicinity of the reaction, with a range of approximately 5 to 9 μm, the diameter of the target cell [16, 17].

For the most widely used $^{10}B$-based neutron capture agent, $^{10}B$-4-borono-L-phenylalanine ($^{10}B$-BPA), CBE values of 3.6-3.8 and 0.9-1.3 have been reported for brain tumour cells and normal tissues, respectively, with tumour to healthy tissue concentration ratios between 5:1 and 8:1 [14, 16, 17]. An alternative capture agent, borocaptate sodium (BSH), has shown potential for NCT applications; the reported range of CBE is between 1.2 and 2.3 in brain tumours and 0.37 to 0.5 in normal tissues, although the uptake concentration ratio tends to be much lower than for BPA (1.2-3.5 in the brain) [28]. The specific values differ for other target tissues, with higher values of CBE reported for liver tumours for both agents (tumour/liver CBE values of 9.94/4.25 and 4.22/0.94, and concentration ratios of 2.8/0.3 for BPA and BSH, respectively) [26, 27, 39].

The $^{157}Gd$ neutron capture reaction follows a somewhat different path, and results in the production of an excited $^{158}Gd$ nucleus and a high-energy gamma ray:

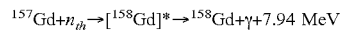
$$^{157}Gd + n_{th} \rightarrow [^{158}Gd]^* \rightarrow ^{158}Gd + \gamma + 7.94 \text{ MeV}$$

Upon relaxation of the excited state, internal conversion (IC) and low-energy Auger electrons are produced, the latter responsible for the majority of the useful therapeutic effects. Classified as a high-LET radiation, Auger electrons travel only a very short distance (a few nanometers in tissue) before depositing their kinetic energy, making them very effective if the source is concentrated in immediate vicinity of a DNA molecule or vital organelles (such as mitochondria). A yield of 5 Auger electrons, 1.8 γ photons and 0.69 IC electrons and 1.0 recoil nucleus has been estimated for the thermal neutron capture reaction.

$^{157}Gd$ is of great interest for neutron capture therapy owing to its extremely high thermal neutron cross-section—the highest of any stable isotope. Free $Gd^{3+}$ ion is highly toxic to organisms both in vitro and in vivo, but chelated $Gd^{3+}$ compounds can be used safely due to their physiological stability [45]. Very high cellular concentrations of gadolinium can be achieved in vitro without significant cytotoxicity (of the order of several thousand ppm). While gadolinium contrast agents such as Gd-DOTA and Gd-DTPA are approved for use in humans diagnostically, neither accumulates to significant concentration within the cell nucleus [40]. Amongst the experimental gadolinium compounds, motexafin-gadolinium (MGd) been proposed as a potential candidate for GdNCT [45]. It is a tumour-specific radiosensitiser, and its combined use with whole-brain radiation therapy has reached Phase III clinical trials [53]. With a 70:1 tumour to healthy tissue uptake ratio, prolonged retention of gadolinium in vitro (up to 2 months) and 90% uptake in glioblastoma cell nuclei, it is a promising candidate for use in NCT [54-56]. Recent efforts towards the development of DNA and mitochondria-targeting gadolinium agents has resulted in a number of promising agents. Morrison et al.\ have reported on the development of a tumour-cell selective mitochondrial agent designed for NCT applications, with cellular concentrations of up to 3000~ppm [45].

Radiotherapy based on $^{10}B$ neutron capture with neutron beams from a nuclear reactor is already an established radiotherapy modality, with a number of accelerator-based epithermal neutron facilities under consideration in Russia, Argentina, Italy and the U.K. [18, 19]. Two $^{10}B$ delivery agents, L-p-boronophenylalanine (L-$^{10}$BPA) and sodium mercaptoundecahydro-closo-dodecaborate ($Na_2{}^{10}B_{12}H_{11}SH$; $Na_2{}^{10}$ BSH) have been used clinically to treat patients suffering from glioblastoma multiforme and malignant melanoma, with phase I clinical trials for the treatment of head and neck tumours and liver metastases under way in Argentina, Finland, Sweden, Japan, Taiwan, and the United States [20, 21]. However, treatment of tissues deeper than approximately 3 cm is not feasible with this technique, owing to the very high neutron fluence at the surface which is required to achieve a therapeutic effect at the target—a consequence of the neutron-moderating effect of the water in human tissue [22].

JP 2016/088895 A discloses a sensitizer for heavy-ion radiotherapy and a heavy-ion radiotherapy, using a fluoridation porphyrinoid binding a boron compound as a sensitizer for heavy-ion radiotherapy administered before the radiation of a carbon ion ray to a tumour, or by using a substance containing a metal complex thereof.

JP 2014/177421 A discloses a sensitizer for proton beam therapy and a proton beam therapeutic method. A fluorinated porphyrinoid binding a boron compound or a metal complex thereof is employed as a sensitizer for proton beam therapy, and a proton beam therapeutic method is disclosed in which this radiosensitizer is administered to a mammal and then a tumour with accumulated radiosensitizer is irradiated with a proton beam.

KR 1568938 B1 discloses a radiation therapy and a diagnosis device using a proton boron nuclear reaction, in which boron captured in a tumour is irradiated by protons to produce three alpha particles that irradiate the region of the tumour.

WO 2017/048944 A1 discloses a method of using of high-Z nanoparticles in radiation therapy, in which target cells are sensitized to ionizing radiation by administering the high-Z particles in conjunction with a de-aggregation agent. The particles may comprise a targeting molecule to enable cellular uptake by the target cells.

JP 2017/096672 A discloses a radiation dosimetry apparatus for use in particle beam therapy system, which has a dose position analyzer that determines correction values for correcting positional information on a fluorescent substance.

SUMMARY OF THE INVENTION

According to a first broad aspect of the invention, there is provided an irradiation method for irradiating a target volume, the method comprising:

providing thermal neutron absorbing nuclides (e.g. a high neutron cross-section agent, such as $^{10}B$ and/or $^{157}Gd$) in or adjacent to the target volume, and producing neutrons by irradiating nuclei (which may be, for example, in the target volume, adjacent to the target volume, and/or be distributed throughout the target volume) with a beam of particles (the 'primary beam') consisting of any one or more of protons, deuterons, tritons and heavy ions (such as ionized $^4He$ (i.e. alpha particles, which are generally regarded as heavy ions), C, O and Si—in particular but by no means exclusively $^9C$, $^{10}C$, $^{11}C$, $^{12}C$, $^{15}O$ $^{16}O$ and high n isotopes of Si), thereby prompting production of the neutrons through non-elastic collisions between the nuclei and the particles;

wherein the neutron absorbing nuclides absorb neutrons (whether by neutron capture or nuclear reactions) produced in the non-elastic collisions (that is, those of the produced neutrons with suitable energies that interact with the neutron absorbing nuclides), thereby producing capture products or fragments that irradiate the target volume.

The method may include configuring the beam of particles so as also to irradiate the target volume. Indeed, in some embodiments, if a sufficient thermal neutron fluence is generated during—for example—particle therapy, that fluence can be exploited therapeutically via the administration of a suitable non-toxic neutron capture agent containing $^{10}B$ or $^{157}Gd$, preferentially absorbed by a tumour at an elevated concentration compared to the surrounding normal tissue. This example, involving a combined therapeutic modality, may be denoted 'neutron capture enhanced particle therapy' (NCEPT).

Generally, it should be appreciated that the term "adjacent" is used in its broadest, conventional sense, thus embracing both "next to or adjoining" and "nearby", but is limited by the requirement that the neutron absorbing nuclides absorb neutrons produced in the non-elastic collisions between the irradiated nuclei and the particles of the beam and in response produce capture products or fragments that irradiate the target volume. Furthermore, the terms "nuclides" and "nuclei" are employed herein because the reactions of interest occur with those species; it will be understood that the relevant species—whether those interacting with the beam of particles (the "nuclei") or those provided for thermal neutron absorption (the "nuclides")—are generally present in atomic form.

Thus, a neutron field can be generated that may be broader than the (primary) beam of particles—in some examples, 3 to 5 times broader. This also allows the targeting of areas (the "target volume") that is outside the volume targeted by or otherwise impinged upon by the primary particle beam. Hence, the nuclei to be irradiated by the primary particle beam can be outside the target volume (including—where appropriate—outside the subject within which is located the target volume, or to create a neutron field in a target volume deep within the subject). This provides a mechanism for irradiation of solid tumours and their surrounding satellite lesions, as well as diffuse cancers, or cancers that by nature are detected late (e.g. pancreatic, stomach, liver, lung) that have involved critical organs in their vicinity, or indeed parasites. In some cases, such as the last example or parasites, it may be desired to irradiate the entire subject (such as a patient's body) with neutrons, such that the target volume is essentially coterminous with the subject or body.

It may be advantageous to configure the primary particle beam so as to deliver its maximum energy outside the subject's body (that is, with the Bragg peak is placed outside the subject's body), while the nuclei are located inside the subject (within which is located the target volume) if it is desired to create a very broad neutron field, such as to irradiate a target volume that includes a diffuse tumour. This technique may be suitable, for example, for treating parasitic organisms.

It is envisaged that the beam may comprise stable and/or radioactive isotopes.

In an embodiment, the beam comprises highly energetic protons and/or heavy ions.

It will be appreciated that some primary particles will be more suitable than others according to application, especially in applications in which n-damage must be weighed against benefit. For example, in the irradiation of some biological samples, ions heavier than oxygen may be unsuitable, as their peak radiobiological effectiveness may lead the peak of their physical dose deposition. It is expected that the most useful primary beam particles, especially for biological applications, will be (ionized) $^{1}H$, $^{2}H$, $^{3}H$, $^{4}H$, $^{5}H$, $^{6}H$, $^{3}He$, $^{4}He$, $^{6}He$, $^{6}He$, $^{7}He$, $^{8}He$, $^{9}He$, $^{10}He$, $^{18}He$, $^{19}He$, $^{9}C$, $^{10}C$, $^{11}C$, $^{12}C$, $^{13}C$, $^{14}C$, $^{15}C$, $^{16}C$, $^{17}C$, $^{18}C$, $^{19}C$, $^{20}C$, $^{21}C$, $^{12}O$, $^{13}O$, $^{14}O$, $^{15}O$, $^{16}O$, $^{17}O$, $^{18}O$, $^{19}O$, $^{20}O$, $^{21}O$, $^{22}O$, $^{23}O$, $^{24}O$, $^{25}O$, $^{26}O$ and $^{28}O$.

In another embodiment, the method includes providing the thermal neutron absorbing nuclides in the form of a composition containing $^{10}B$ and/or $^{157}Gd$. The composition may be preferentially absorbed by a malignant target tissue.

In one embodiment, the capture products or fragments comprise energetic charged particles. The capture products or fragments may comprise energetic charged particles of high relative biological effectiveness.

In a further embodiment, the beam irradiates matter along its path (which may include the target volume) in a spot scanning manner, a uniform scanning manner, a fast scanning manner, raster scanning manner, and/or a passively scattered manner. The beam may obtain appropriate energy by cyclotron or synchrotron. The irradiation results in the production of thermal neutrons for subsequent capture by the thermal neutron absorbing nuclides.

According to a second broad aspect of the invention, there is provided a method of irradiating biological tissue (e.g. a tumour, invasive satellite lesions and/or intracranial metastatic lesions—such as in the brain) using a proton, deuteron, triton or heavy ion beam, the method comprising irradiating a target volume that includes the biological tissue according to the method of the first aspect.

In an embodiment, the target volume is inside a subject, and the point at which the beam deposits its maximum energy (or 'stops') is outside the subject.

This aspect also provides a method of treating a patient by irradiating the biological tissue.

In an embodiment, the target volume is inside the patient, and the beam deposits its maximum energy (or 'stops') outside the patient.

According to this aspect, the method may further comprise applying an immunotherapy in combination or conjunction with the irradiating of the biological tissue. It is envisaged that this may provide a mechanism for controlling/activating an immune-regulatory response, such as to treat cancer and/or an autoimmune disease.

According to a third broad aspect of the invention, there is provided a method of inhibiting growth of any one or more of a tumour, satellite lesion (e.g. one or more invading satellite lesions) and/or a metastatic lesion (e.g. an intracranial lesion), the method comprising:

dosing the tumour, satellite lesion and/or metastatic lesion (including more than one thereof) with a composition comprising thermal neutron absorbing nuclides (such as in the form of a high neutron cross-section agent); and irradiating nuclei in or adjacent to the tumour, satellite lesion and/or metastatic lesion with a beam of particles (the 'primary beam') consisting of any one or more of protons, deuterons, tritons and heavy ions (such as ionized $^{4}He$, C, O and Si), thereby producing neutrons through non-elastic collisions between nuclei in or adjacent to the tumour, satellite lesion and/or intracranial metastatic lesion and the particles;

wherein the neutron absorbing nuclides absorb neutrons produced in the non-elastic collisions, thereby producing capture products or fragments that irradiate the tumour, satellite lesion and/or intracranial metastatic lesion.

Thus, in some embodiments, a tumour (and possibly other malignant tissues) uptake the neutron capture agent(s). The tumour is irradiated with the primary beam and a broad neutron field is formed through fragmentation; the neutrons of that neutron field are in turn captured by the tissues that have taken up the neutron capture agent, resulting in the emission of high LET by-products at cell level.

In certain other embodiments, a tumour, parasites and/or immunoregulators may uptake the neutron capture agent. The primary beam of high energy is typically used in such applications, with a point of maximum energy deposition outside the body/patient/object that either includes or constitutes the target volume. A broad field of neutrons is created inside the body/patient/object (in addition to a low dose deposited along the path of the primary beam). Any organism or cell that has taken up the neutron capture agent(s) receives a dose—which may be lethal—through the emission of the by-products from the secondary capture (i.e. of neutrons by the neutron capture agent or agents).

Inhibiting the growth of a satellite lesion and/or a metastatic lesion may be in the form of inhibiting the growth of a plurality of satellite or metastatic lesions, or in the form of inhibiting the development of one or more additional invasive satellite or metastatic lesions.

For example, if a sufficient thermal neutron fluence is generated during heavy ion therapy, it may be exploited (such as therapeutically) via the administration of a suitable (generally non-toxic) composition (e.g. a $^{157}Gd$ and/or $^{10}B$-bearing composition), preferentially absorbed by the tumour, satellite lesion and/or intracranial metastatic lesion at an elevated concentration compared to the surrounding normal tissue.

In an embodiment, the beam comprises highly energetic protons and/or heavy ions.

In another embodiment, the method includes providing the thermal neutron absorbing nuclides in the form of a composition containing $^{157}Gd$ and/or $^{10}B$. The composition may be preferentially absorbed by a malignant target tissue.

In a further embodiment, the capture products or fragments comprise energetic charged particles. The capture products or fragments may comprise energetic charged particles of high relative biological effectiveness.

The invention also provides a method for controlling an irradiation system, comprising controlling the irradiation system to perform the method of any of the above aspects of the invention.

According to a fourth broad aspect of the invention, there is provided a computer-implemented method of determining parameters for particle therapy, the method comprising:

modelling or simulating (such as by Monte Carlo simulation), based on a set of default or selected parameters (which may include neutron fluences, determined either theoretically or empirically):

a) irradiation of nuclei in or adjacent to a target volume with a beam of primary particles consisting of any one or more of protons, deuterons, tritons and heavy ions (such as $^4$He, C, O and Si);

b) production of neutrons through non-elastic collisions between the nuclei in or adjacent to the target volume and the primary particles; and c) production of capture products or fragments released as a result of neutron capture and nuclear reactions between at least one high neutron cross section agent (such as $^{10}$B and/or $^{157}$Gd) and thermal neutrons produced from the non-elastic collisions between atoms in the target volume and the primary particles (expressed, for example, in the form of total biological effective dose);

determining a difference between the production of the capture products or fragments with either (i) a predetermined template or desired production of the capture products or fragments, or (ii) empirical validation data; and generating a modified set of parameters (that is, typically by modifying one or more of the parameters) according to the difference.

In an embodiment, the modelling further comprises modelling irradiation of a tissue within the target volume by the capture products or fragments. The tissue may comprise a tumour or a portion thereof, one or more (e.g. invading) satellite lesions and/or one or more metastatic lesions.

In another embodiment, the modelling further comprises locating a composition comprising the thermal neutron absorbing nuclides in the target volume.

The parameters may comprise any one or more of:
i) duration of irradiation;
ii) composition of the beam;
iii) energy of the particles of the beam;
iv) peak radiobiological effectiveness of the particles of the beam;
v) physical dose deposition of the particles of the beam;
vi) the composition;
vii) concentration (e.g. in parts per million or ppm) of the composition;
viii) spatial distribution of the composition;
ix) fluence of the produced neutrons;
x) target volume position relative to the beam; and
xi) ion specific radiobiological efficacy.

In a further embodiment, the method includes modelling or simulating the target volume as a tissue equivalent material, such as PMMA (poly(methyl methacrylate)). In one alternative, the tissue equivalent material comprises a skull phantom, such as in the form of a phantom that simulates bone followed by muscle.

In one embodiment, the empirical reaction validation data comprises neutron fluence data.

The method may include determining one or more sets of parameters for a particle therapy parameter library.

According to this aspect, there is also provided computer software configured to, when executed by one or more processors, implement the method of determining parameters for particle therapy of this aspect. This aspect also provides a computer-readable medium (which may be non-transitory), comprising such computer software.

According to a fifth broad aspect of the invention, there is provided an irradiation system, comprising:

a particle source for supplying primary particles comprising any one or more of protons, deuterons, tritons and heavy ions;

an accelerator for providing a particle beam by accelerating the particles;

an extraction beamline for extracting the particle beam from the accelerator;

one or more beam steering units configured to direct the particle beam; and a control system for controlling the irradiation system;

wherein the control system includes or is configured to access an irradiation program (typically comprising a set of particle therapy parameters) for implementing a predetermined irradiation of a target volume, the predetermined irradiation comprising:

irradiating nuclei in or adjacent to the target volume with the particle beam, thereby prompting production of neutrons through non-elastic collisions between nuclei provided in or adjacent to the target volume and the particles, whereby thermal neutron absorbing nuclides (such as in the form of a high neutron cross-section agent) provided before irradiation at the target volume absorb neutrons produced in the non-elastic collisions, thereby producing capture products or fragments that irradiate the target volume (and possibly, in biological applications, satellite lesions, parasites and/or metastatic lesions).

It will be appreciated that the particle beam in this (and each of the other aspects) will commonly interact with other matter in its path, and therefore prompt the production of neutrons through such additional non-elastic collisions. These neutrons may also usefully contribute to the consequent neutron field that then interacts with the thermal neutron absorbing nuclides.

In an embodiment, the irradiation program, or a set of parameters employed thereby, is adapted or personalized for a specific target volume or subject.

In another embodiment, the irradiation system comprises beam cleaning and/or scanning elements (e.g. proportional counters and filters).

In another embodiment, the particle source includes an ionizer for ionizing (and optionally decomposing where required) hydrogen, helium, carbon dioxide, oxygen or other feed gas. It will be appreciated by the skilled person that there are other suitable techniques, and these may be employed as suitable. For example, an oxygen beam may be obtained by fragmentation of $^{18}$O in a beryllium target, and separated using a fragment separator (FRS).

In an embodiment, the accelerator comprises a cyclotron or a synchrotron. The accelerator may further comprise a linear accelerator for providing an initial acceleration to the particles and feeding the cyclotron or a synchrotron.

In an embodiment, the target volume includes a tumour or part thereof, or one or more micrometastases.

According to a sixth broad aspect of the invention, there is provided a control system for controlling an irradiation system, the control system comprising:

a particle supply controller configured to control a particle source of the irradiation system, the particle source supplying primary particles comprising any one or more of protons, deuterons, tritons and heavy ions;

an accelerator controller configured to control an accelerator of the irradiation system, the accelerator providing a particle beam by accelerating the particles;

a beam steerer for controlling one or more beam steering units configured to direct the particle beam; and an extraction controller for controlling extraction of accelerated particles from the accelerator;

wherein the control system includes or is configured to access an irradiation program (typically comprising a set of particle therapy parameters) for implementing a predetermined irradiation of a target volume, the predetermined irradiation comprising:

irradiating nuclei in or adjacent to the target volume with the particle beam, thereby prompting production of neutrons through non-elastic collisions between nuclei in or adjacent to the target volume and the particles, whereby thermal neutron absorbing nuclides provided before irradiation at the target volume (and possibly, in biological applications, satellite lesions, parasites and/or metastatic lesions) absorb neutrons produced in the non-elastic collisions, thereby producing capture products or fragments that irradiate the target volume.

The system may comprise a treatment planning system (TPS) configured to determine the irradiation program, such as based on a standard set of parameters for the accelerator and subject data (e.g. medical images of the subject).

The system may further comprise a couch controller for controlling a position and/or orientation of a subject couch one or more times, so as to locate the target volume relative to a particle beam provided by the irradiation system to deliver the predetermined irradiation.

In another aspect, the invention provides a method for controlling an irradiation system, comprising controlling the irradiation system to perform the method of any one of the first, second and third aspects.

It should be noted that any of the various individual features of each of the above aspects of the invention, and any of the various individual features of the embodiments described herein including in the claims, can be combined as suitable and desired. In addition, it is possible to provide various embodiments by combining appropriately a plurality of components disclosed in the disclosed embodiments. For example, some components may be deleted from the disclosed embodiments. Further, the components of different embodiments may be combined appropriately.

BRIEF DESCRIPTION OF THE DRAWING FIGURES

In order that the invention be better ascertained, embodiments will now be described, by way of example, with reference to the accompanying drawing in which.

Figure 7A:
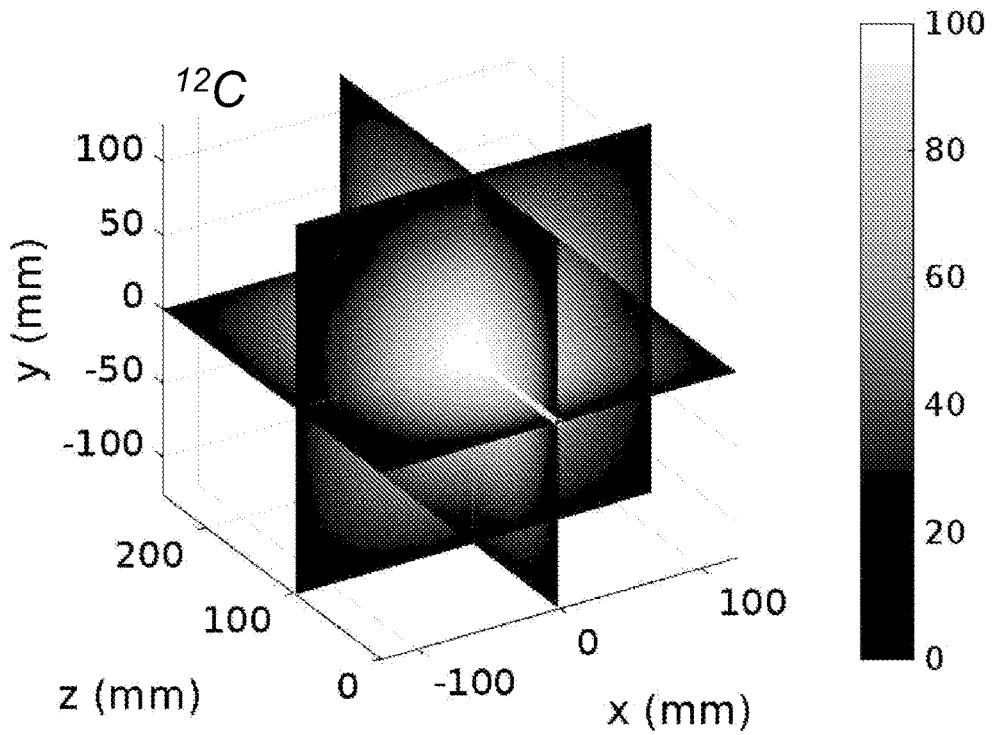
FIGS. 7A to 7C are three-dimensional visualisations of the thermal neutron distribution resulting from irradiation of the PMMA phantom monoenergetic 250 MeV/u, 290 MeV/u and 350 MeV/u $^{12}C$ beams, normalised per primary particle.
Figure 7B:
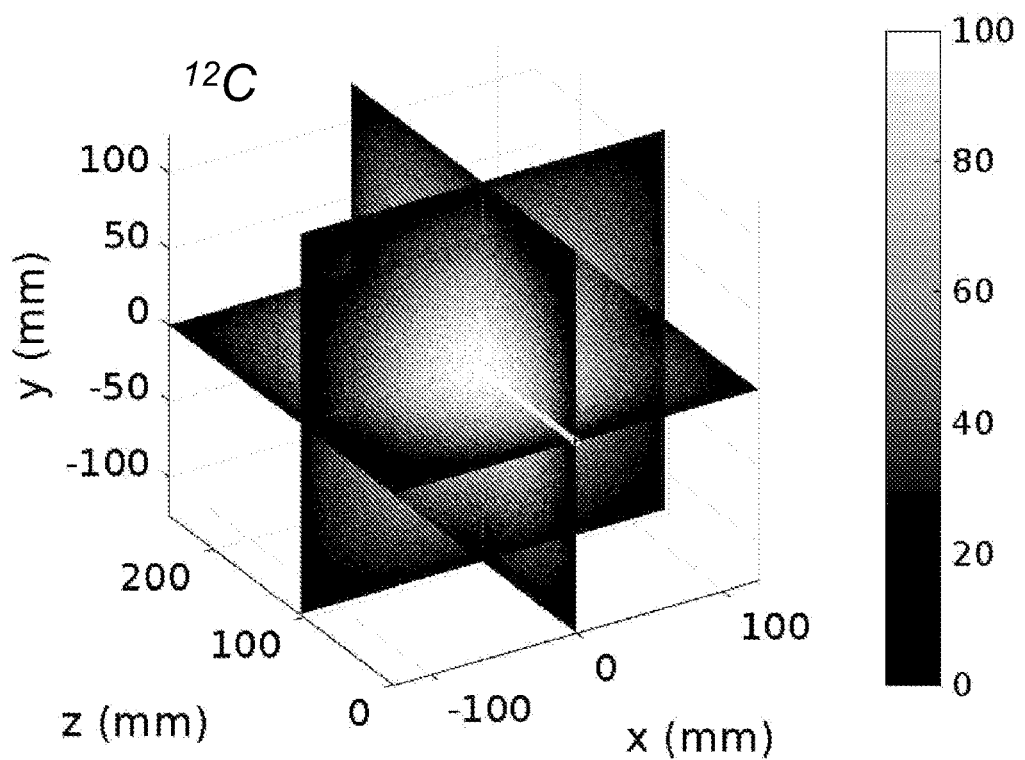
Figure 7C:
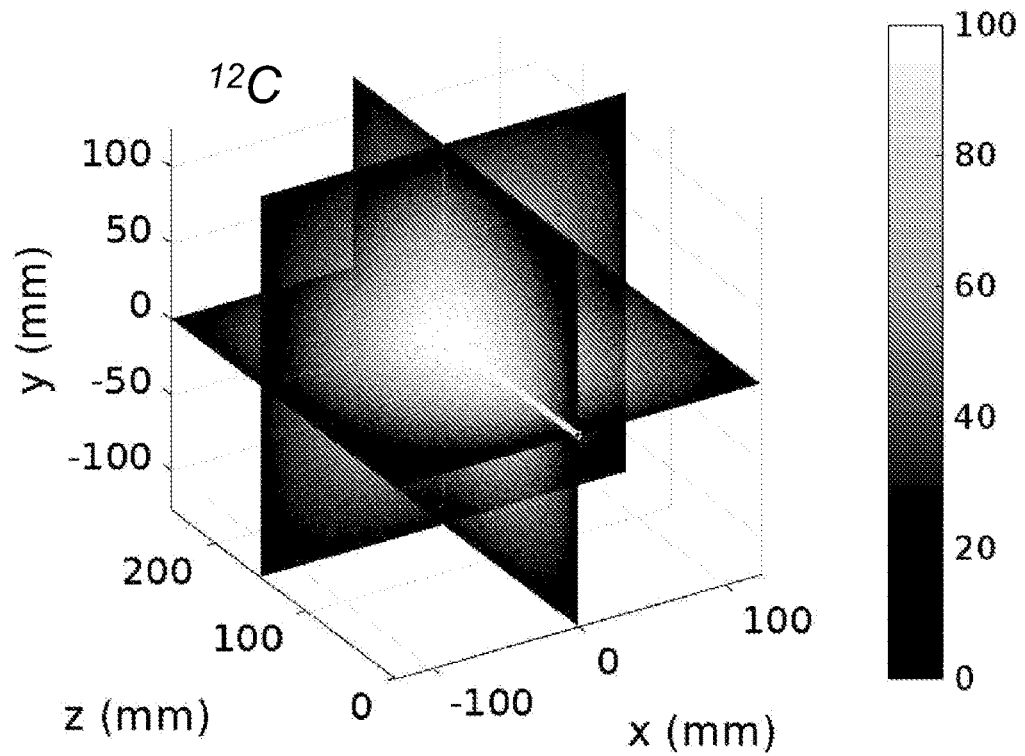
Figure 8A:
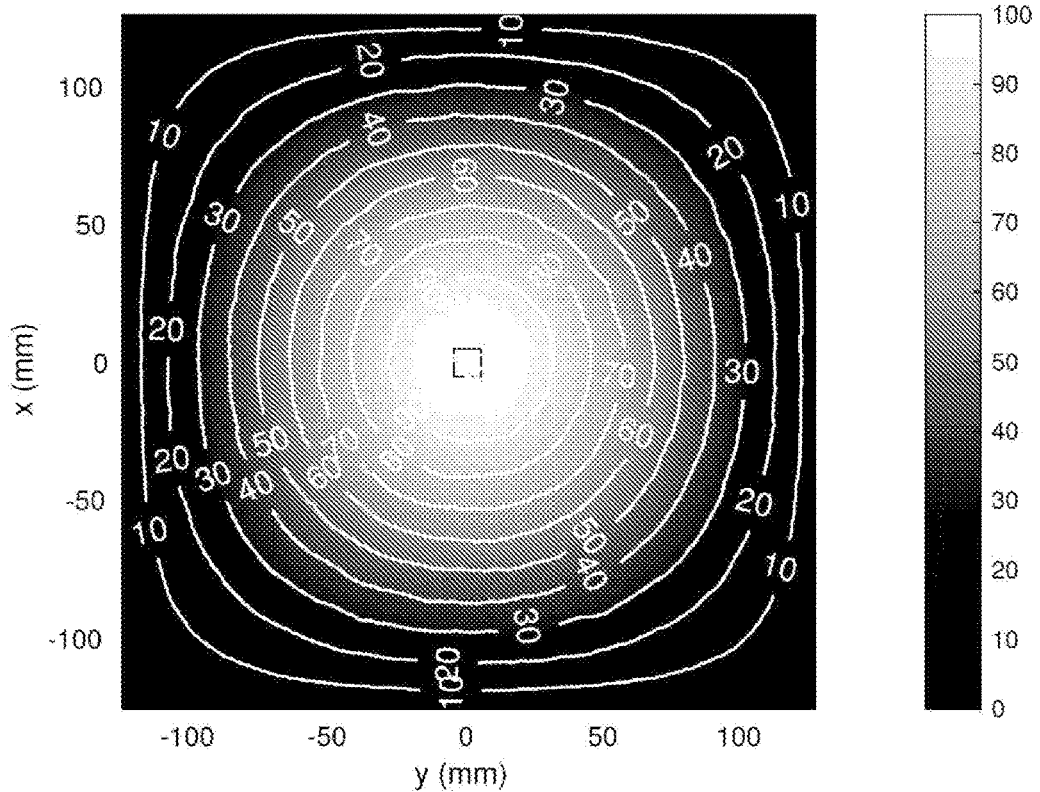
Figure 8B:
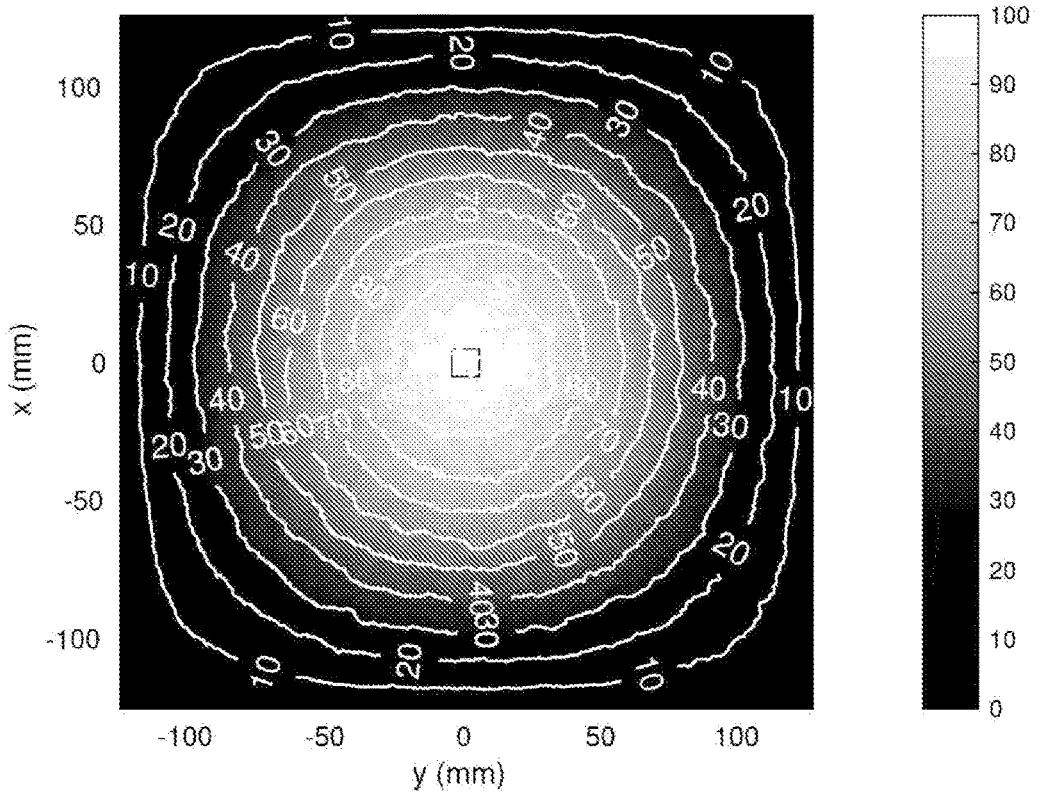
Figure 8C:
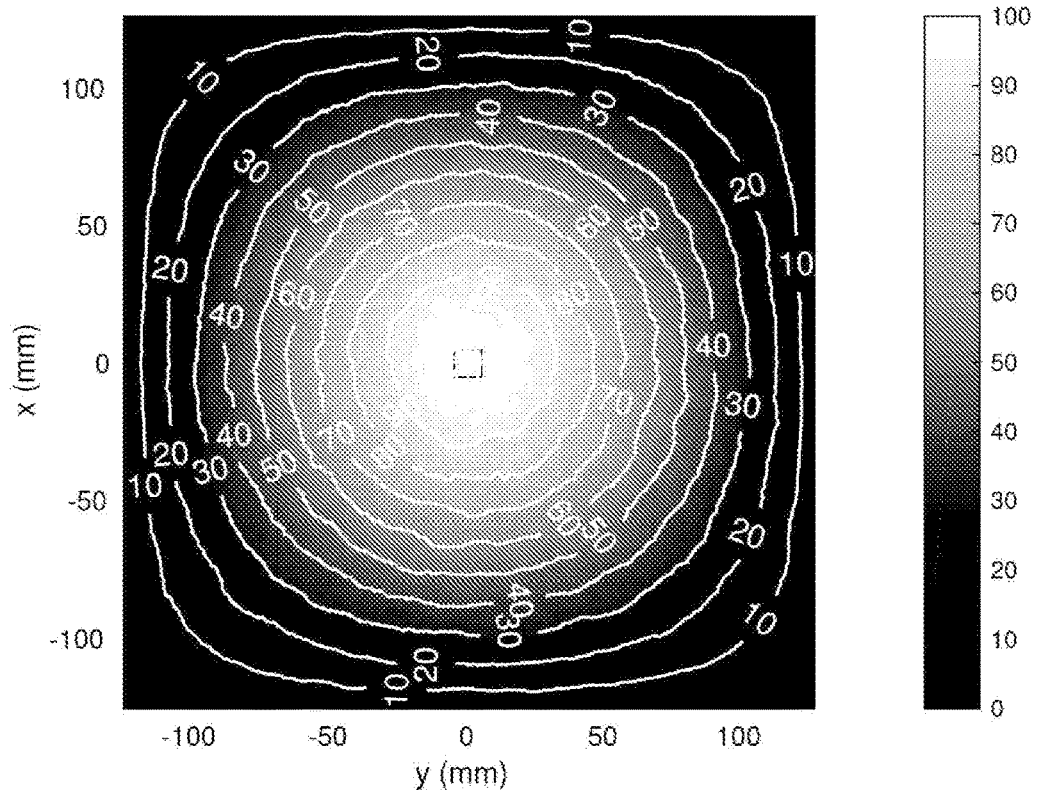
Figure 8D:
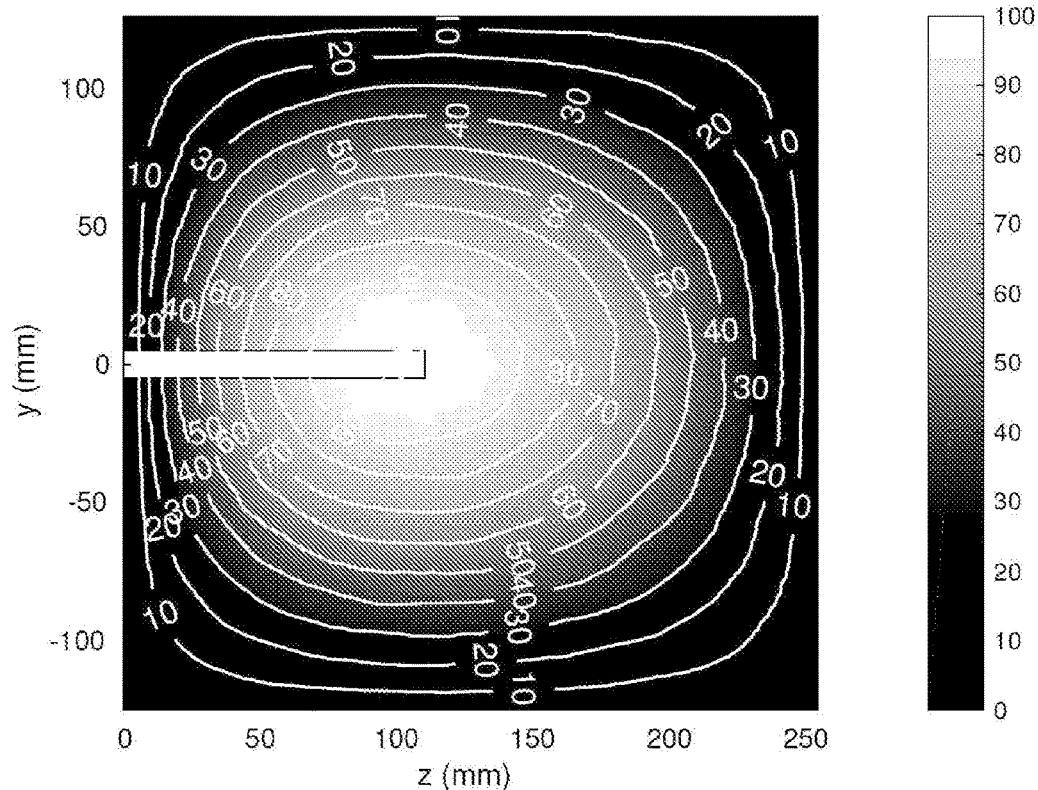
Figure 8E:
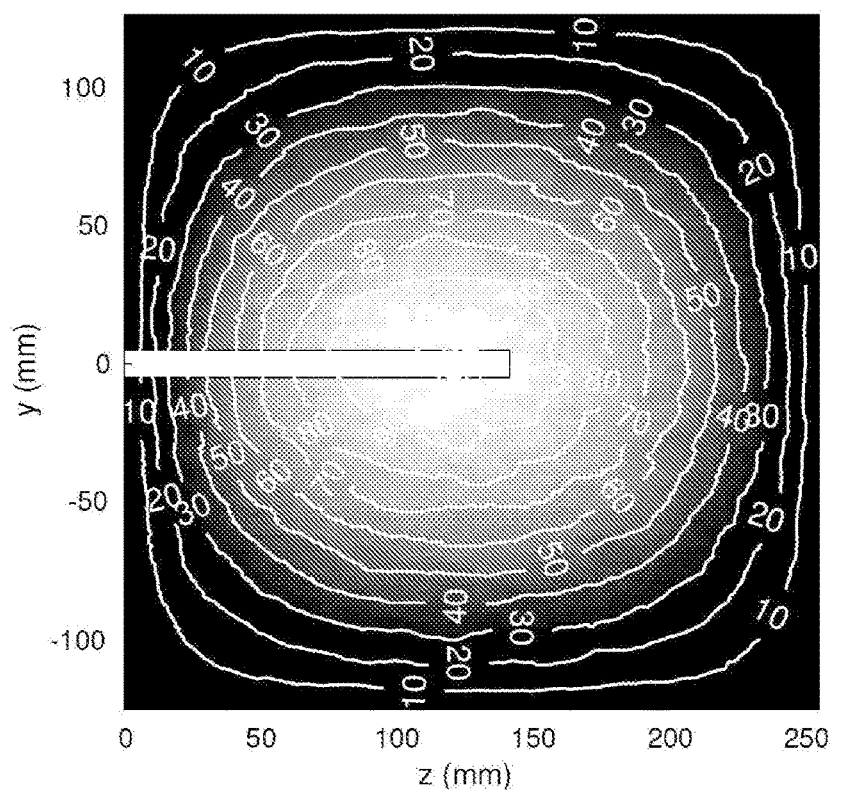
Figure 8F:
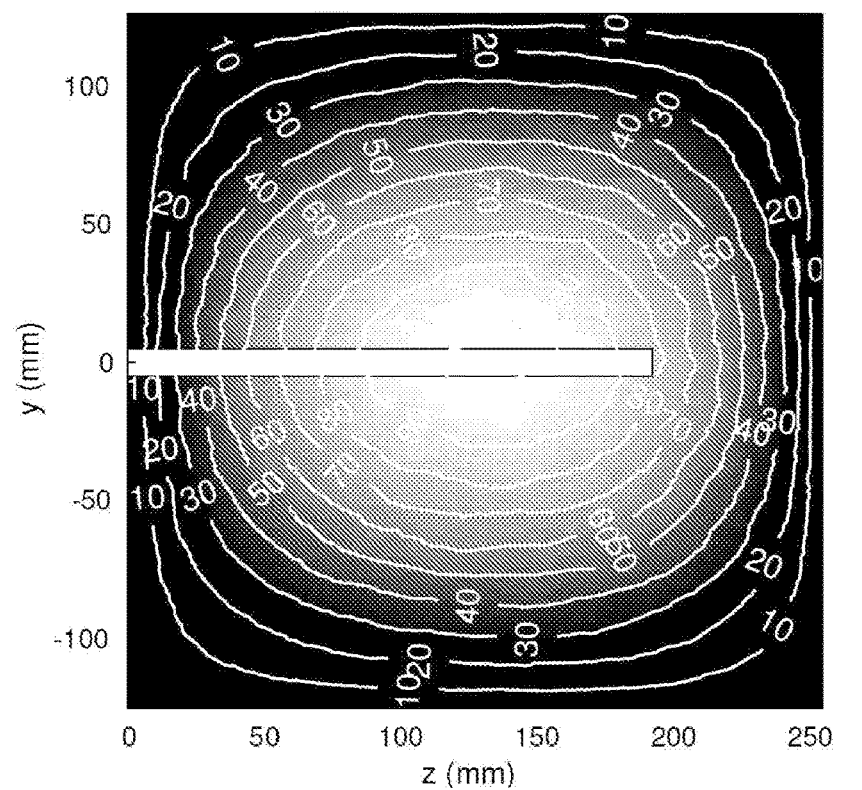
Figure 9A:
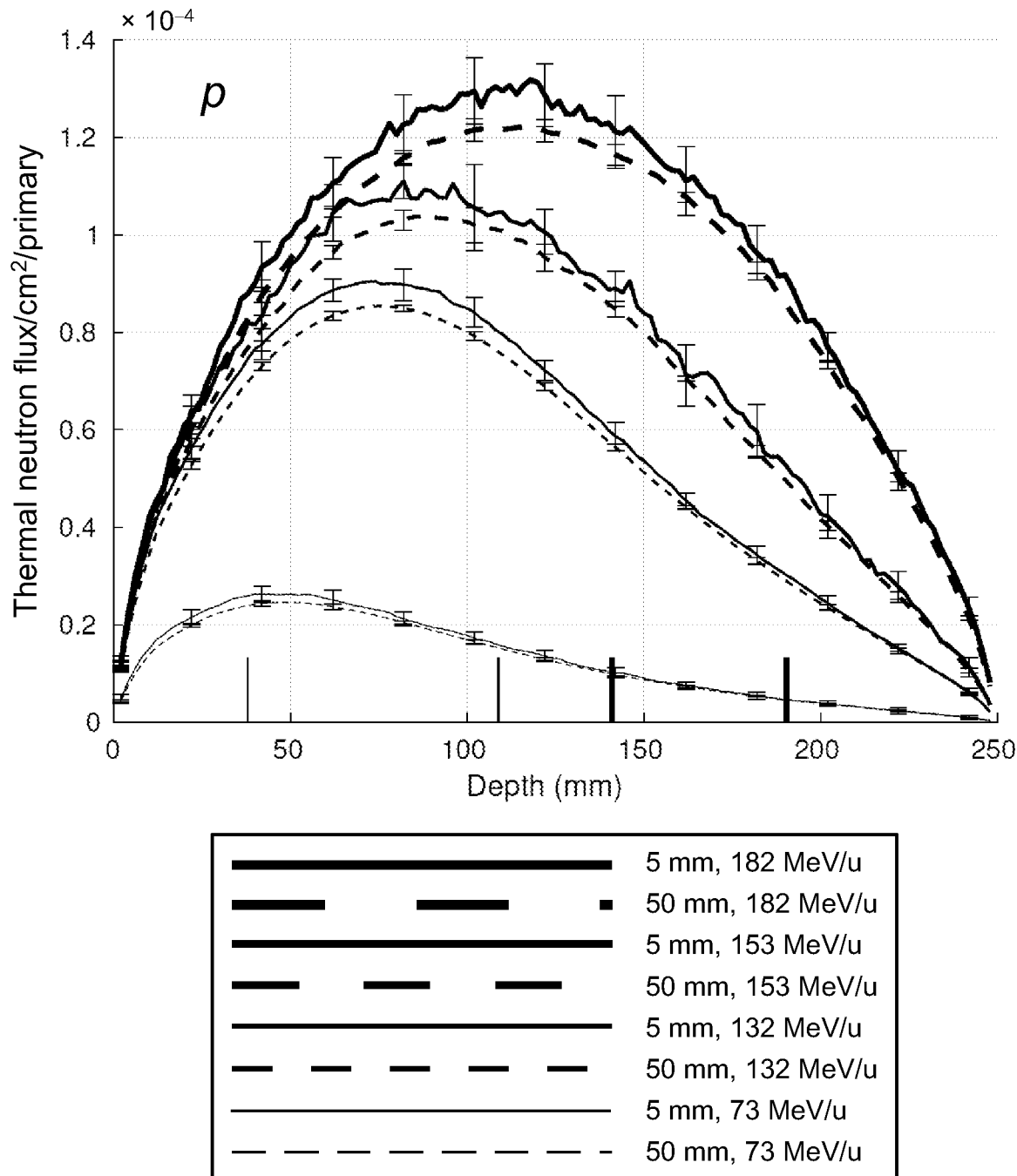
Figure 9B:
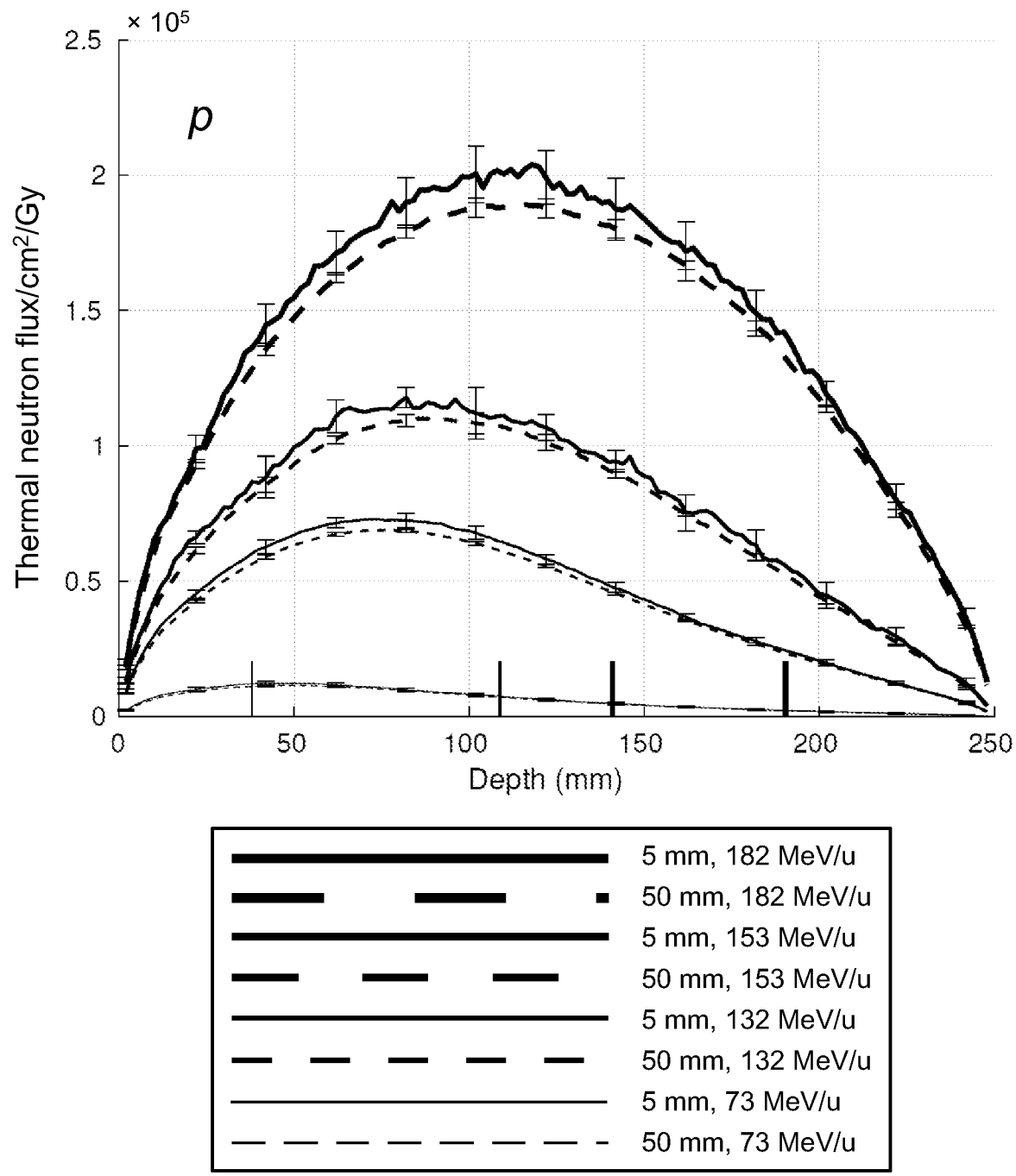
Figure 9C:
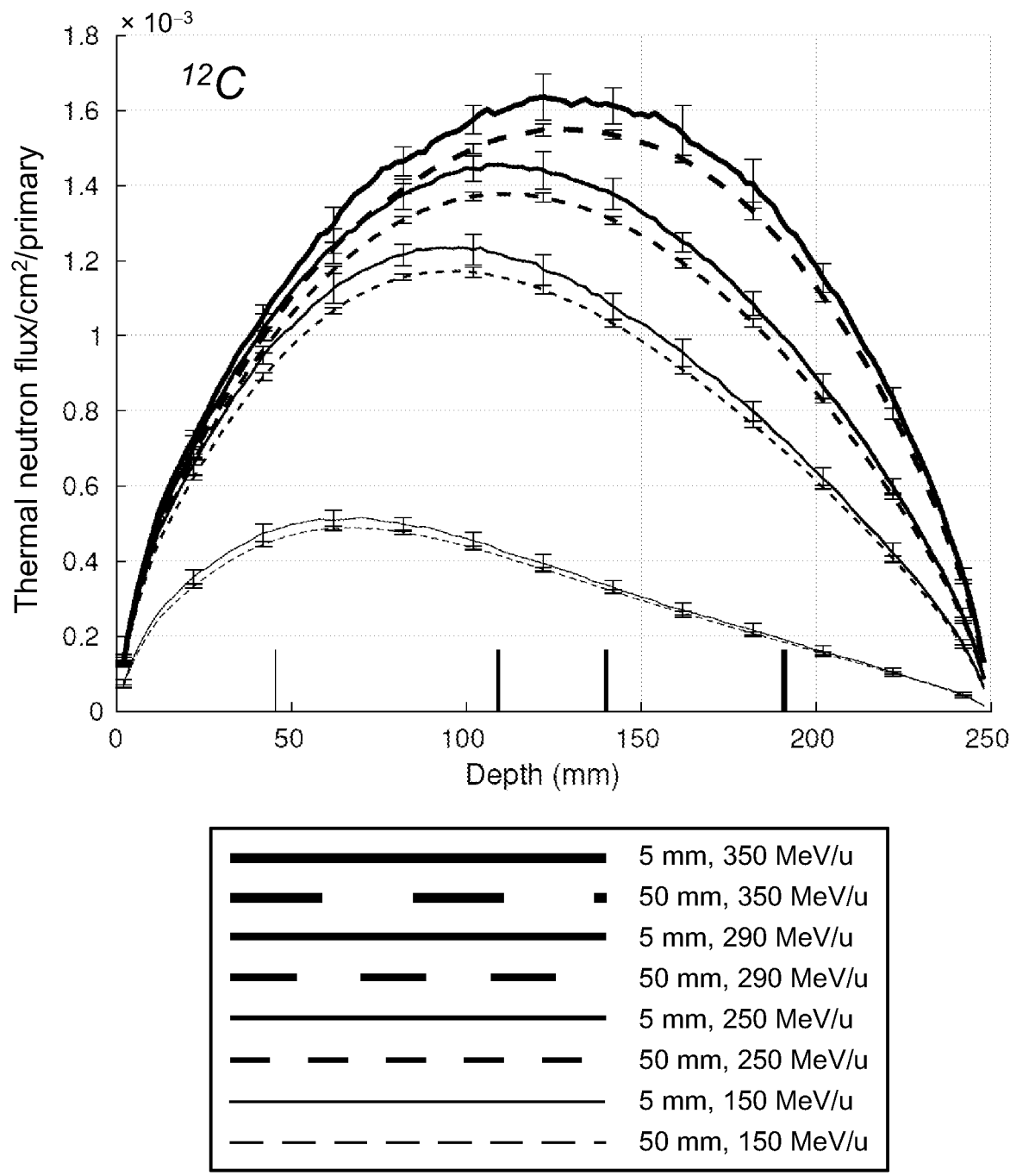
Figure 9D:
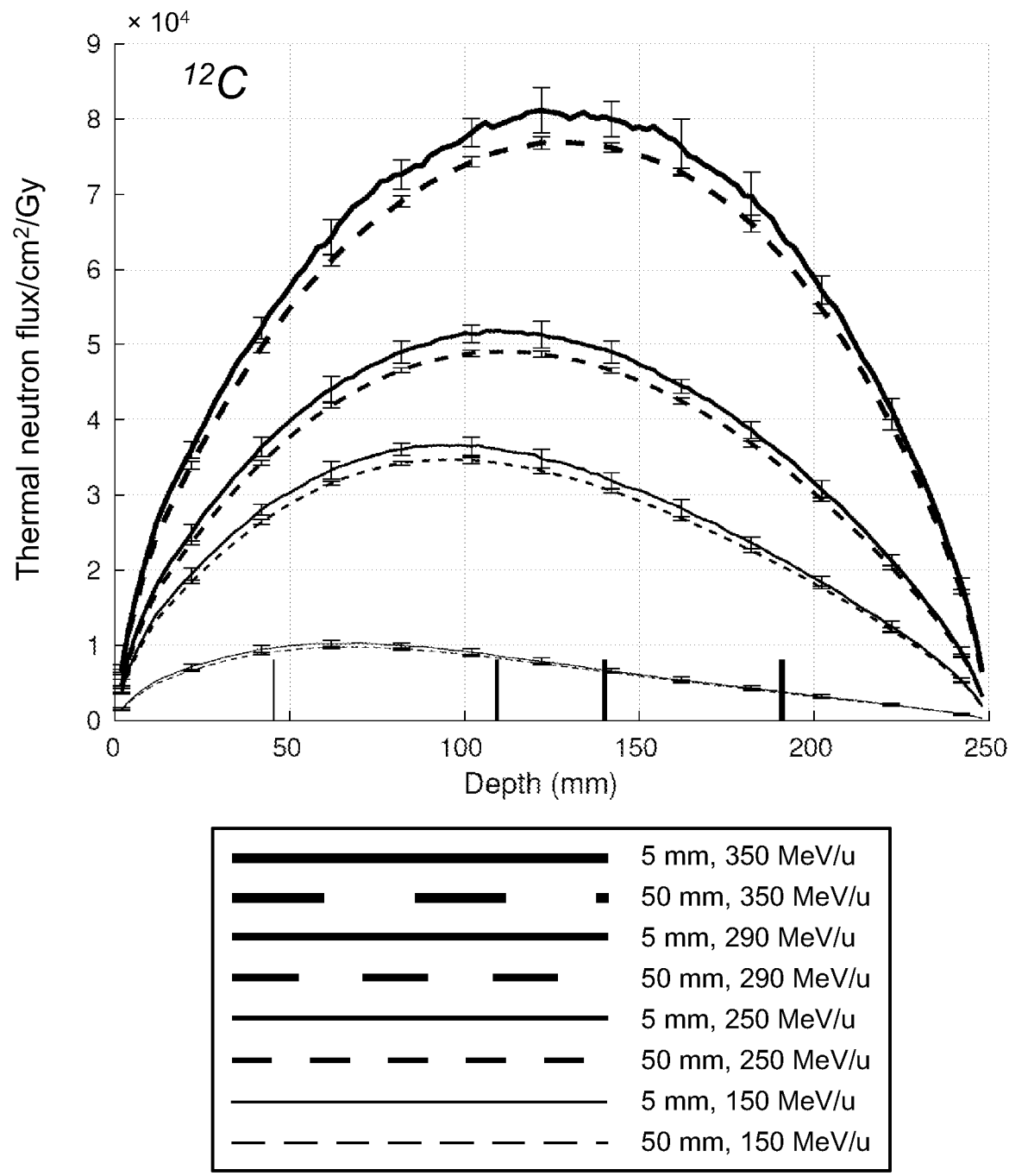
Figure 9E:
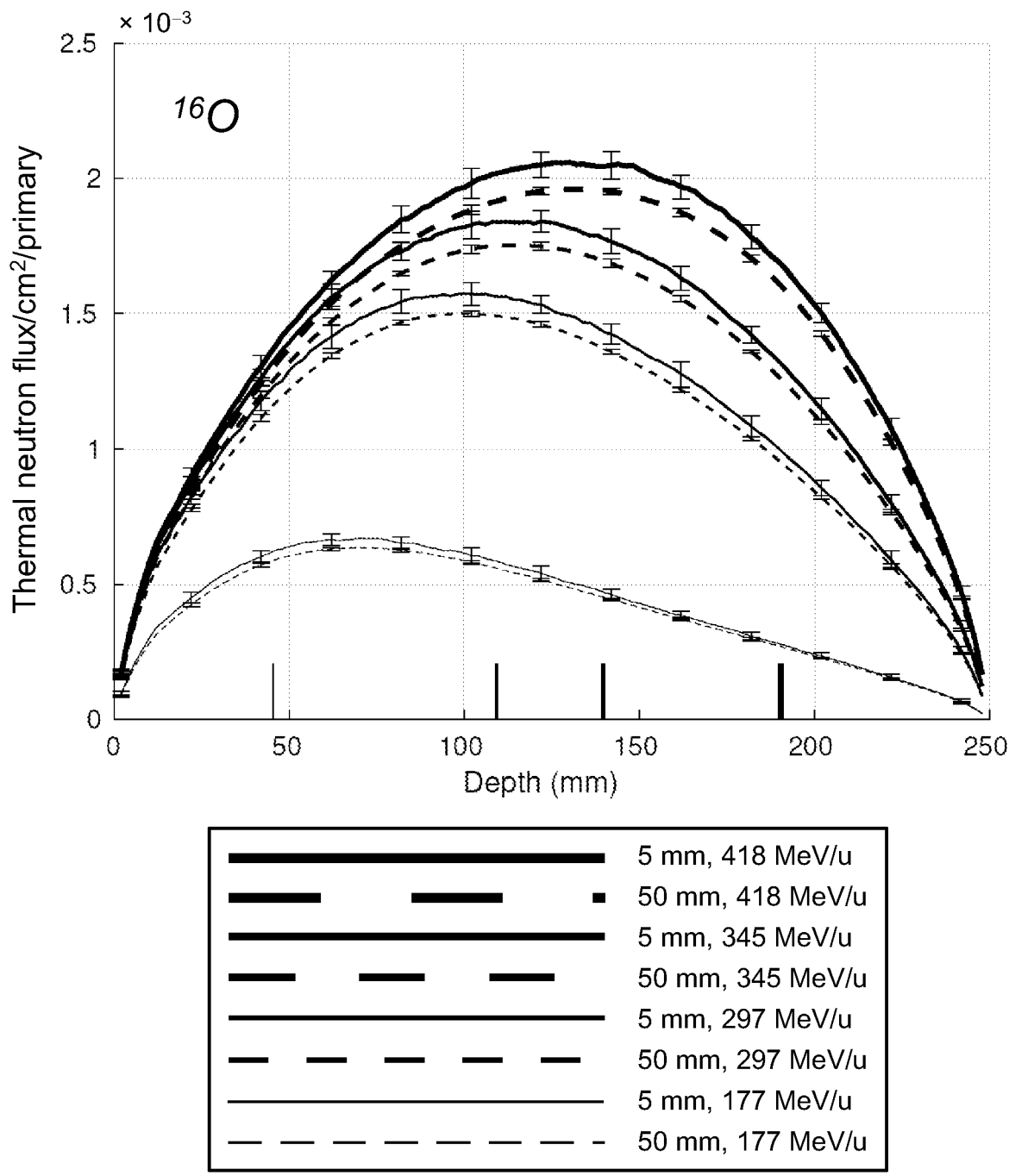
Figure 9F:
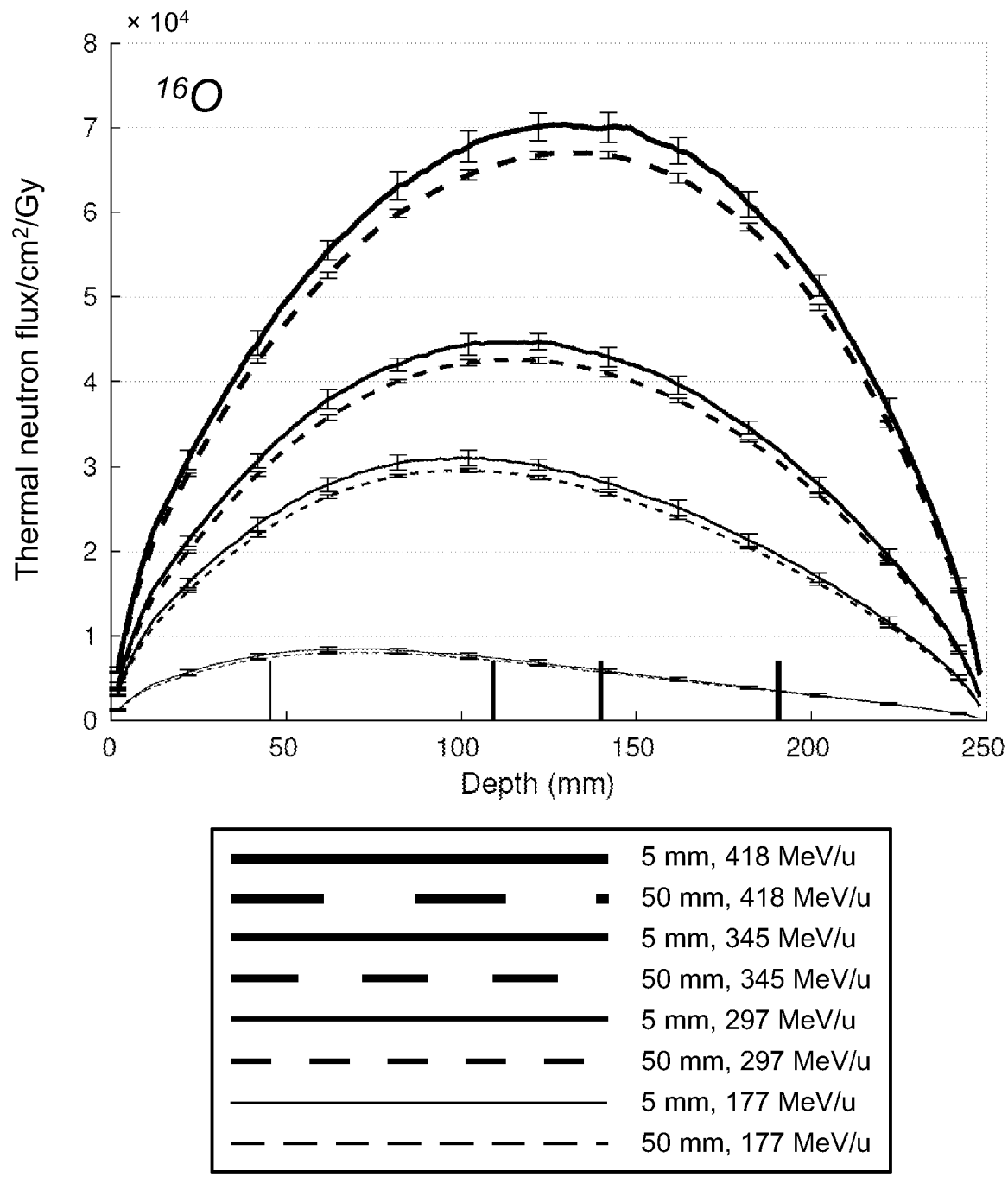
Figure 10:
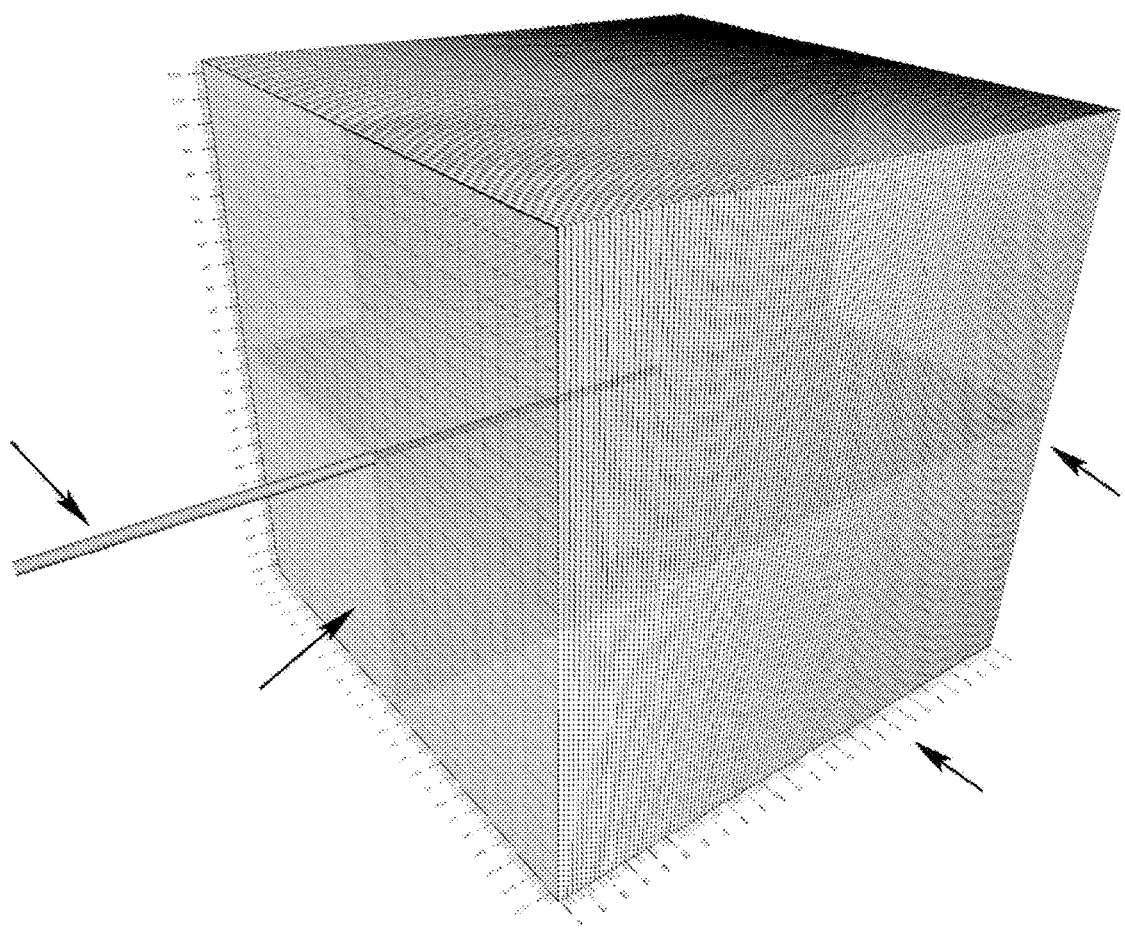
Figure 11A:
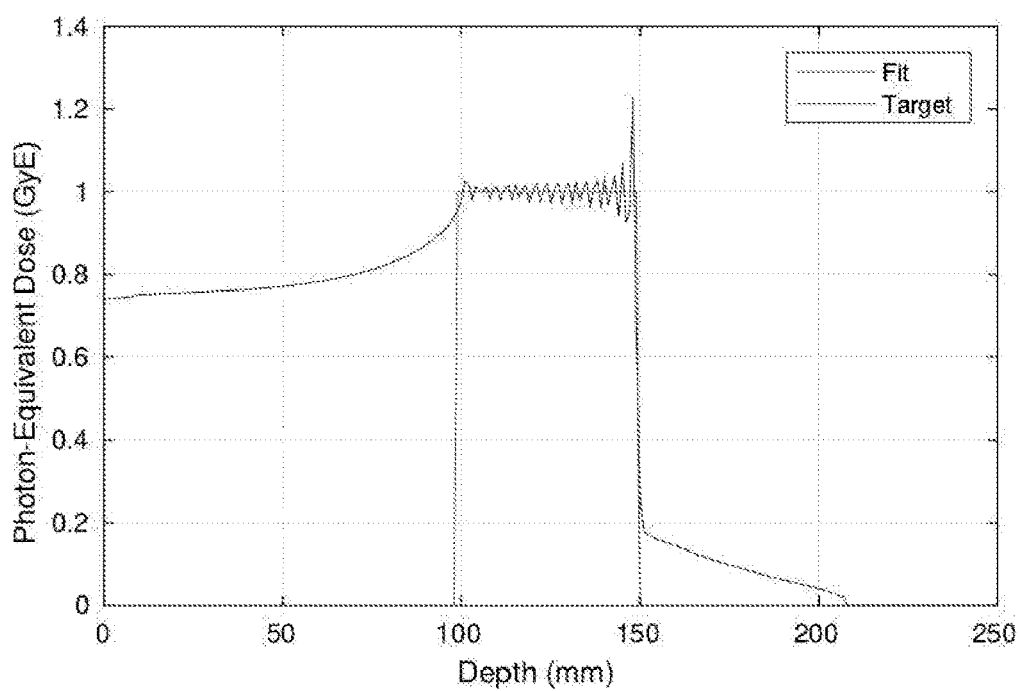
Figure 11B:
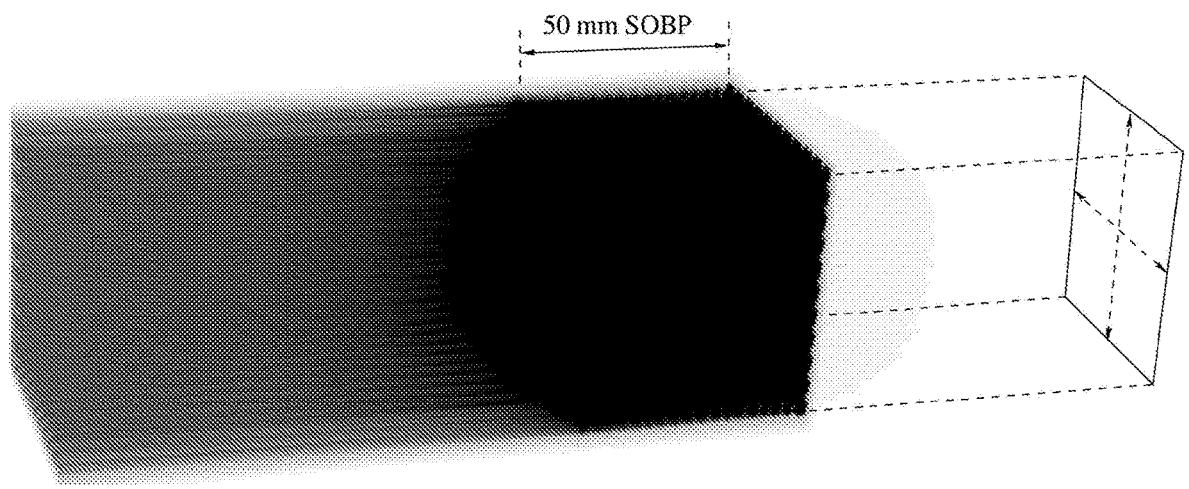
Figure 11C:
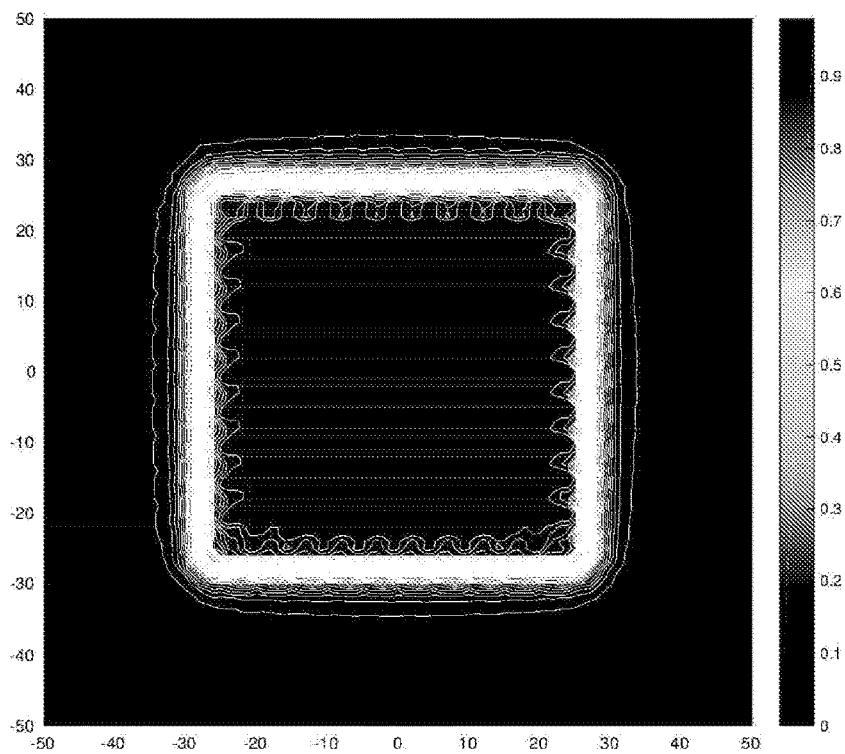
Figure 11D:
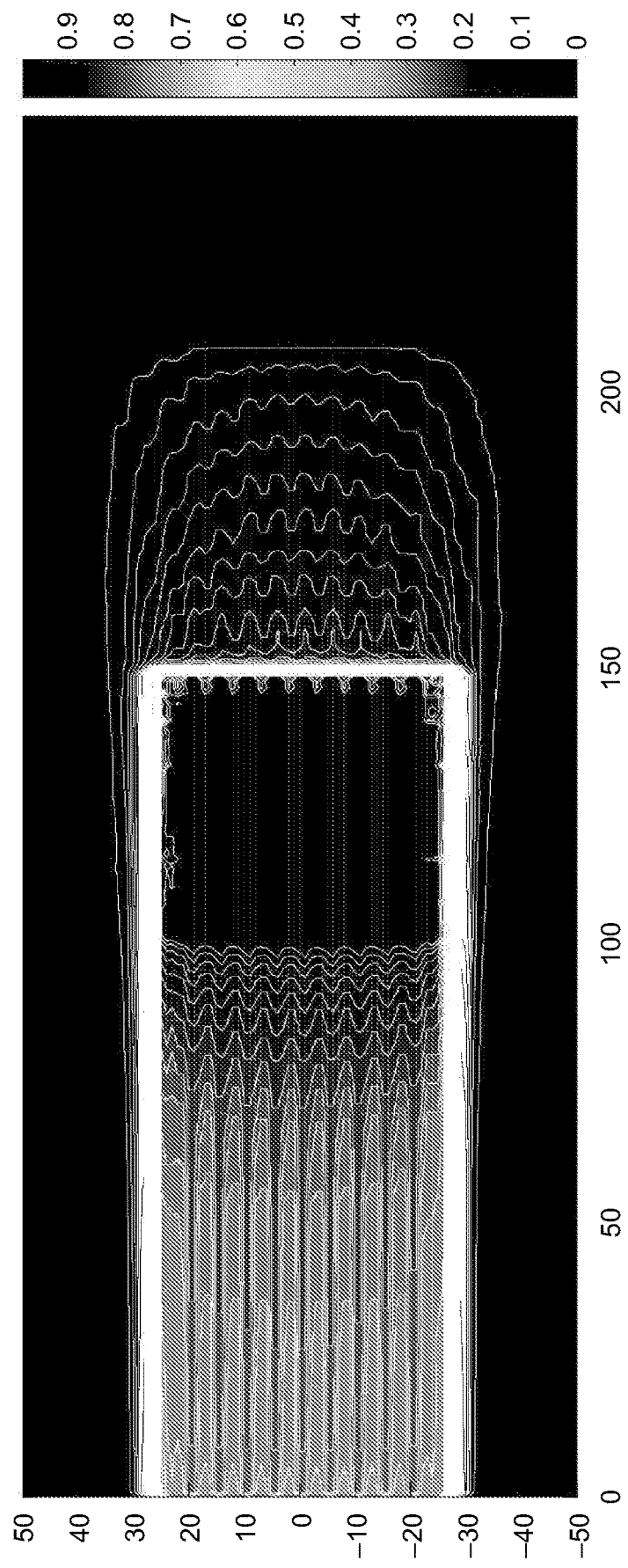
Figure 12A:
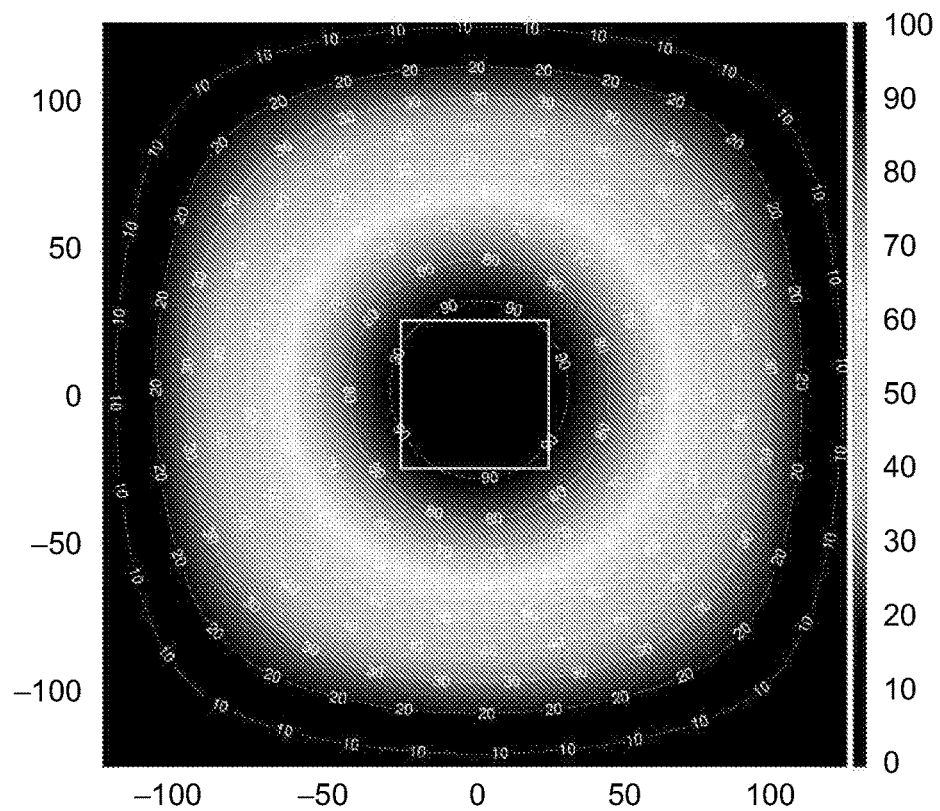
Figure 12B:
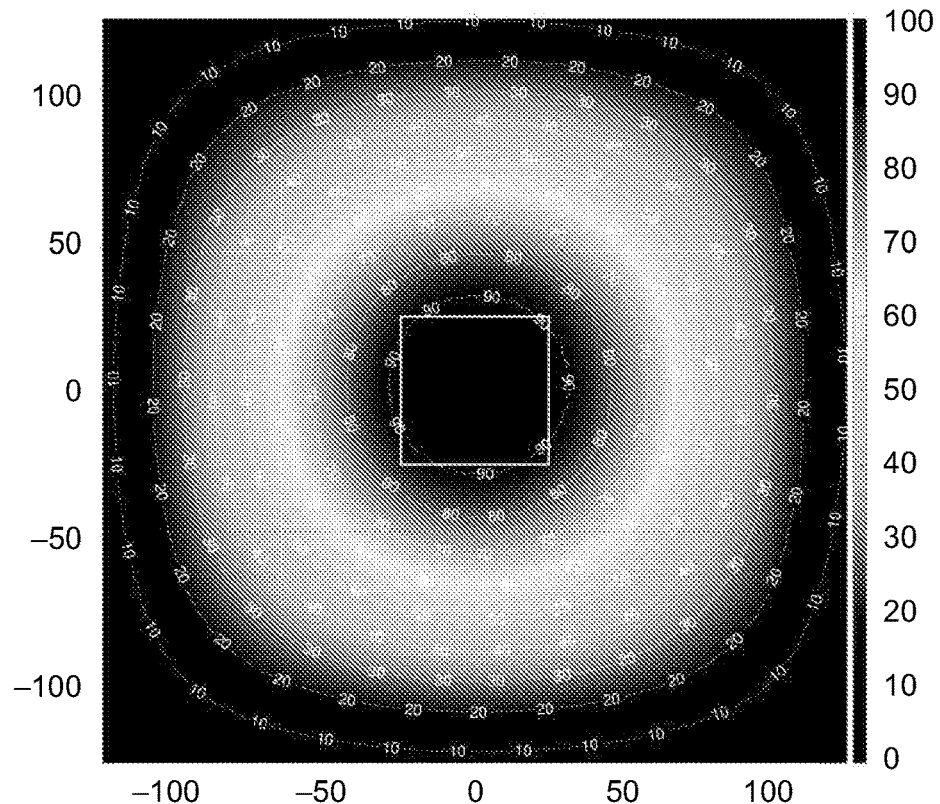
Figure 12C:
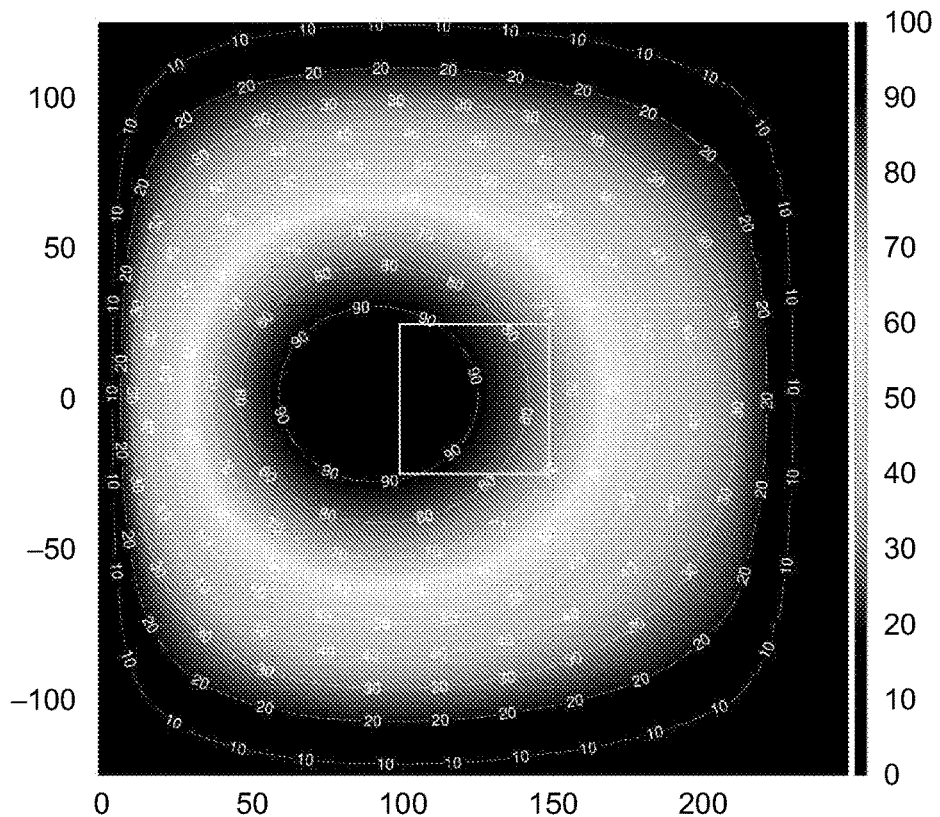
Figure 12D:
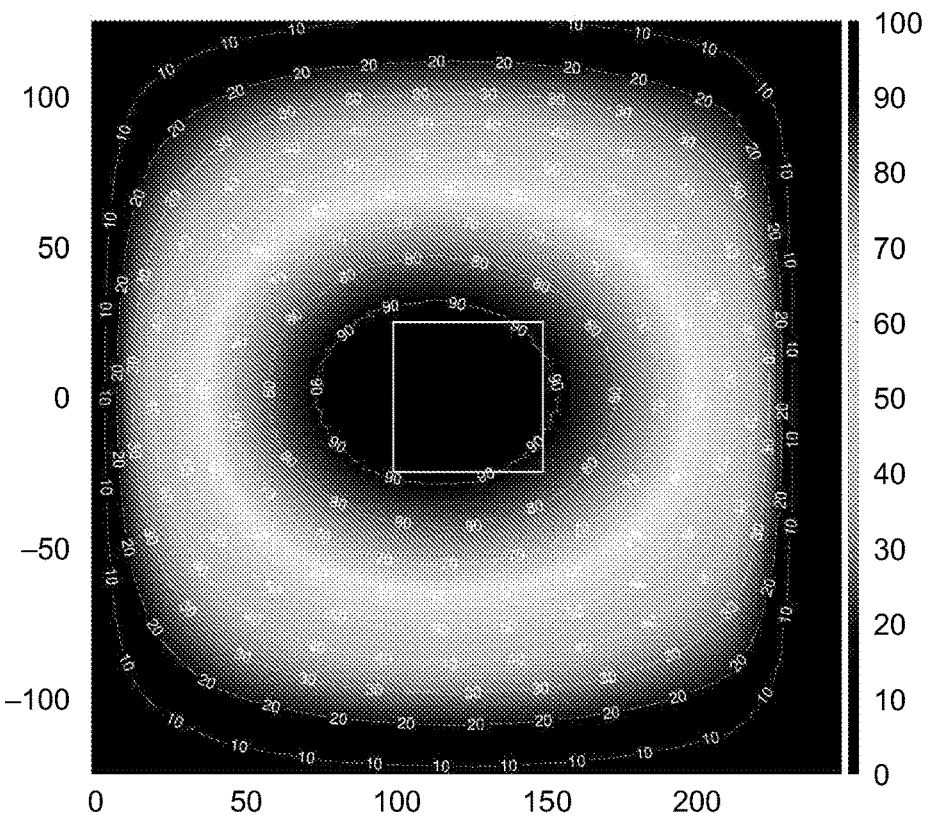
Figure 12E:
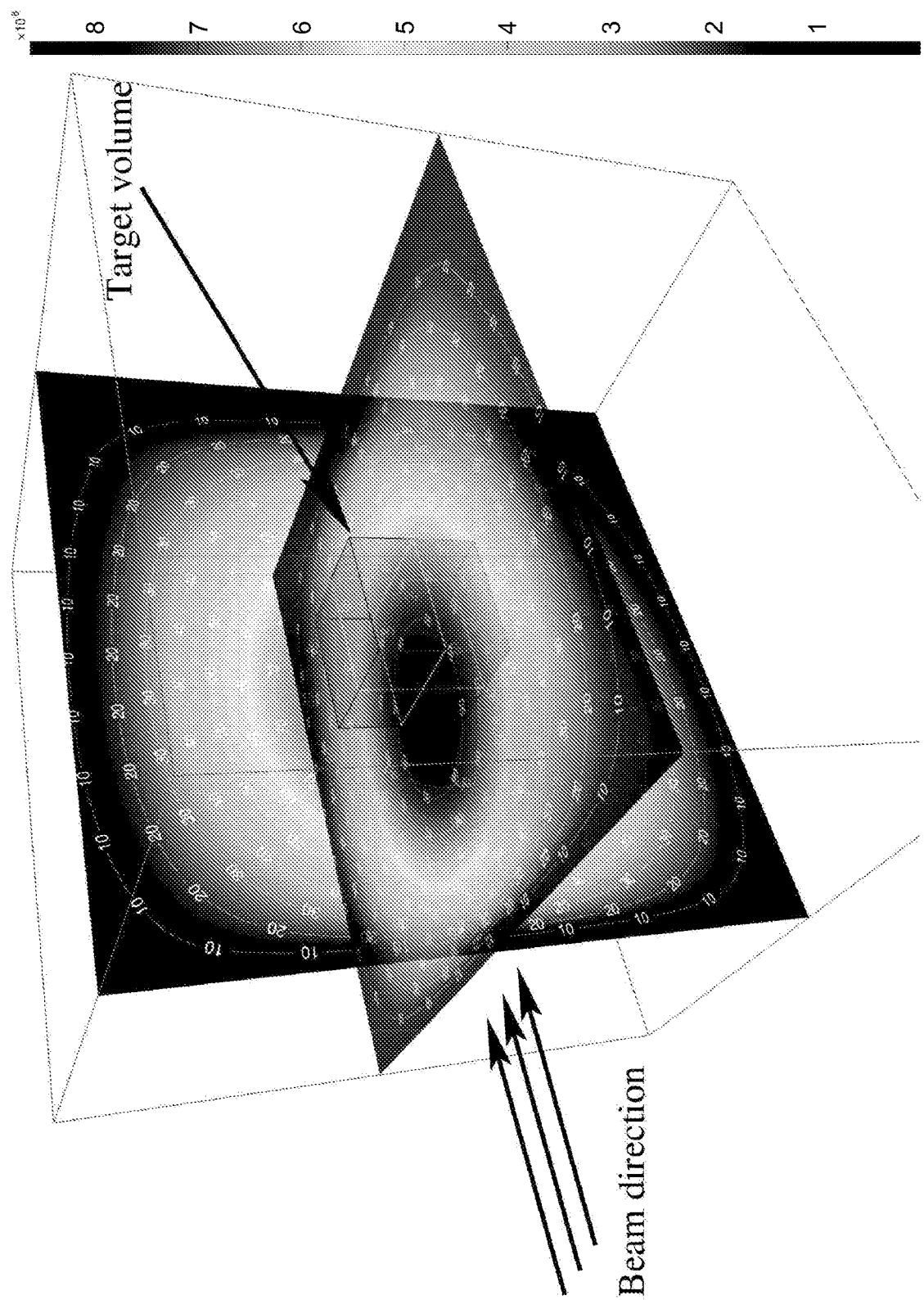
Figure 12F:
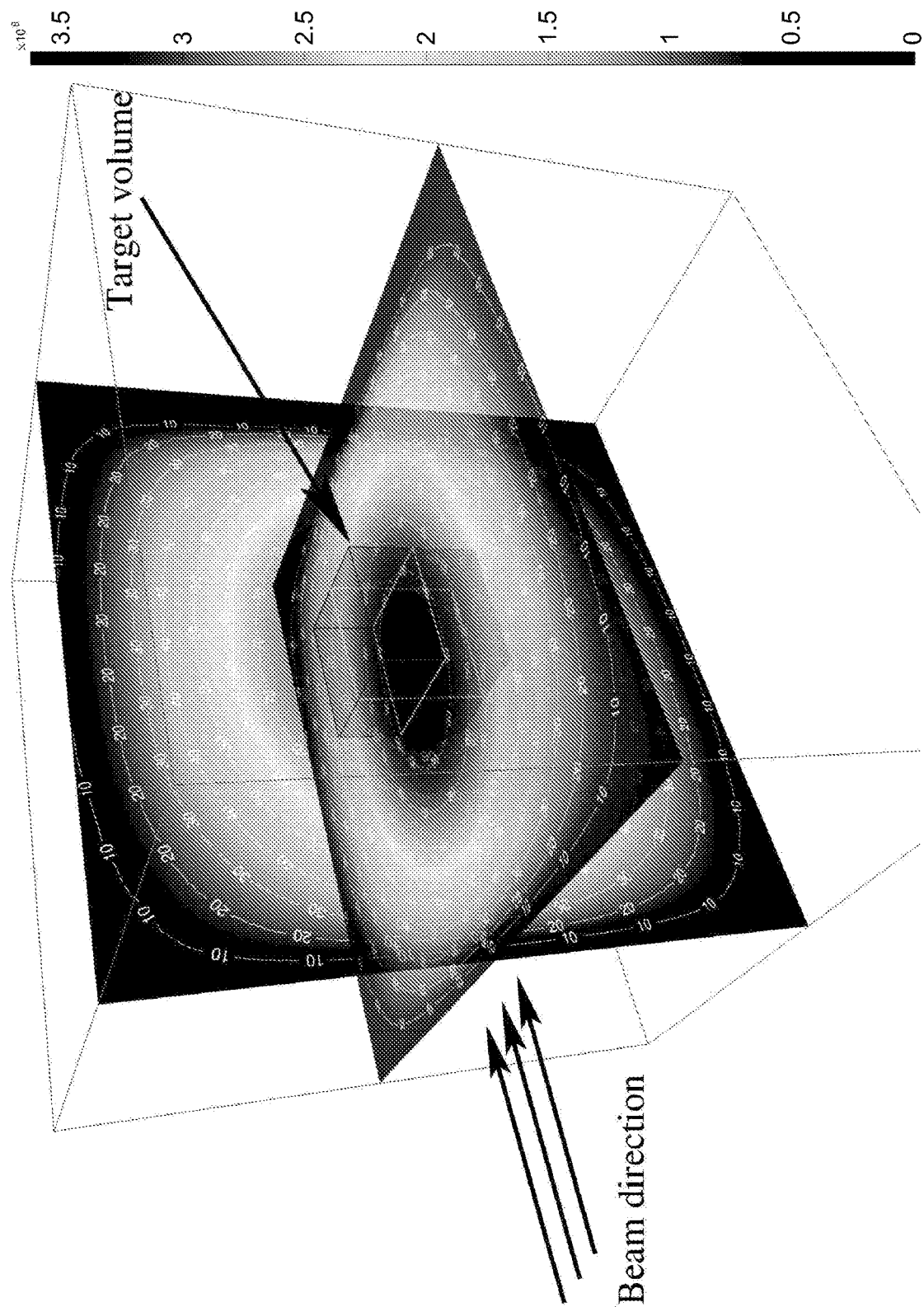
Figure 13:
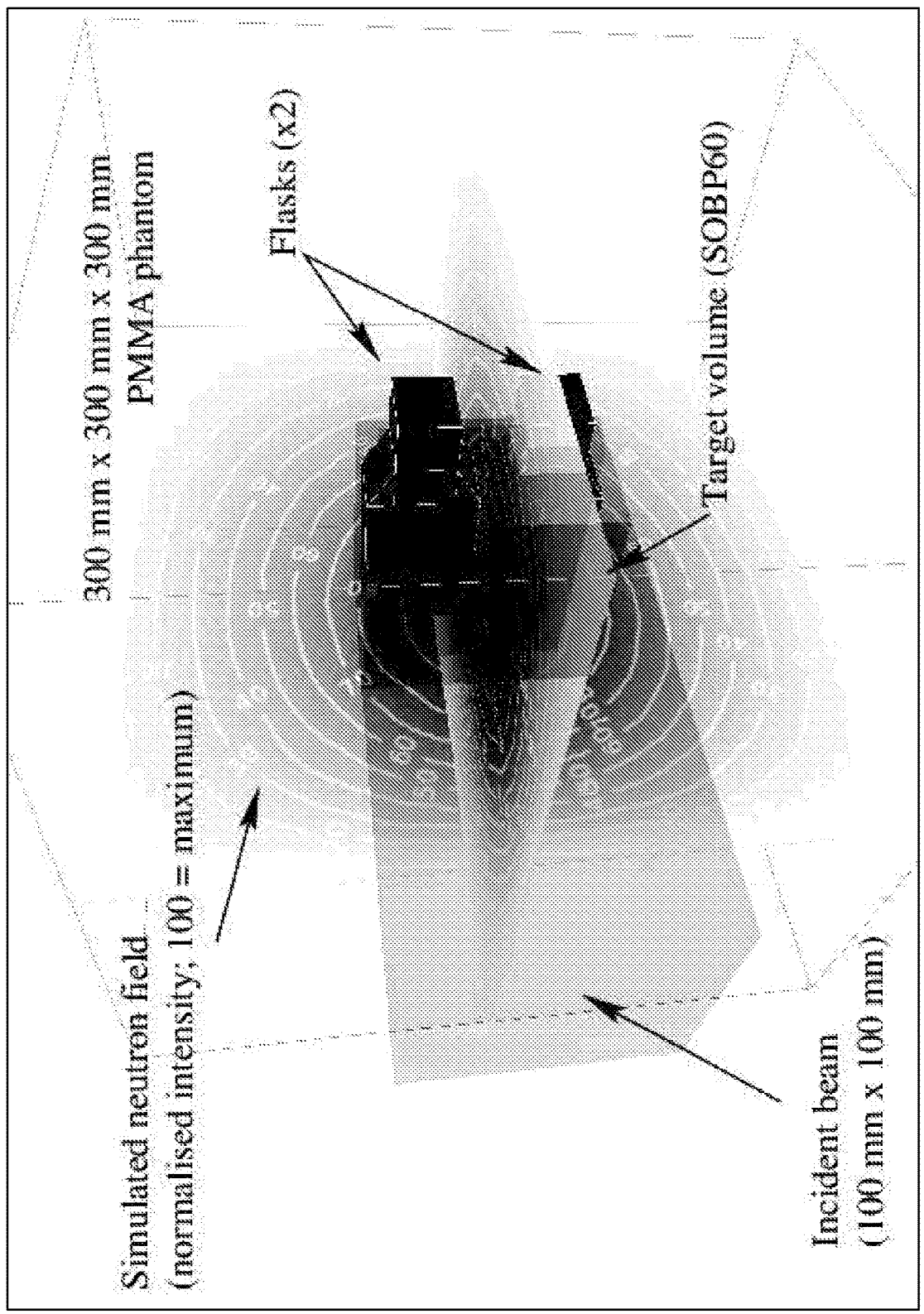
Figure 14:
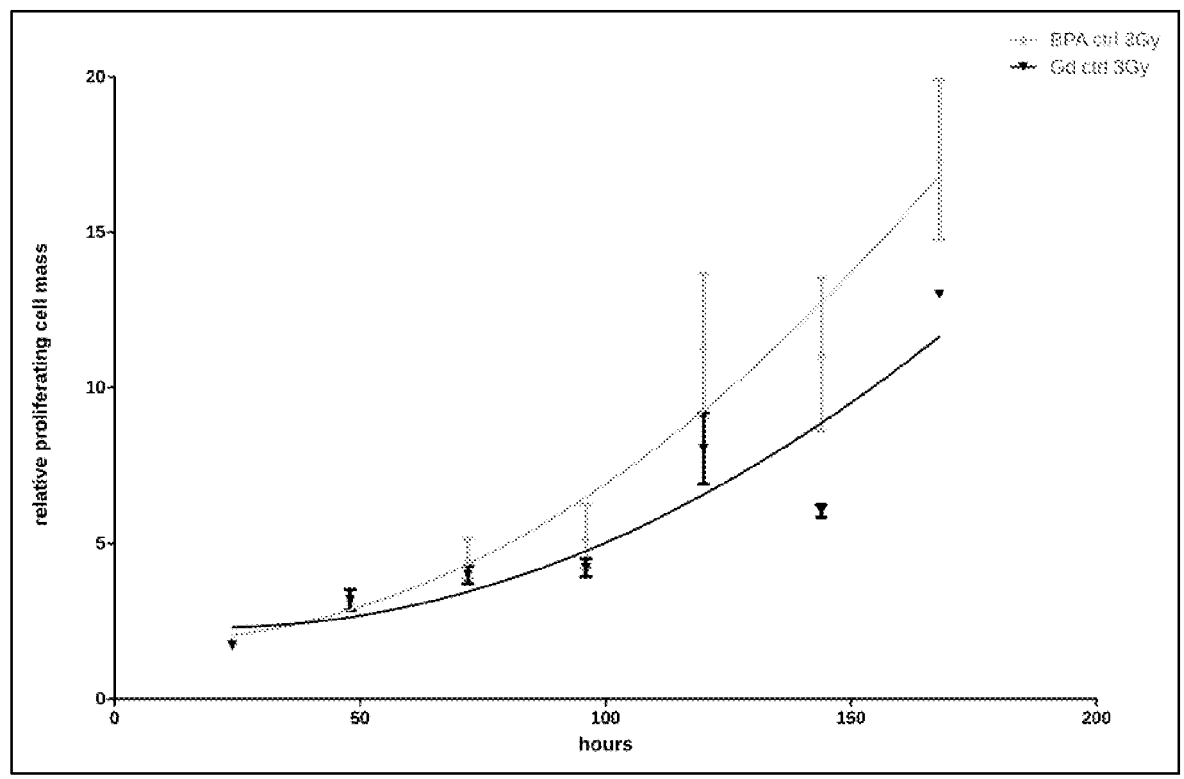
Figure 15:
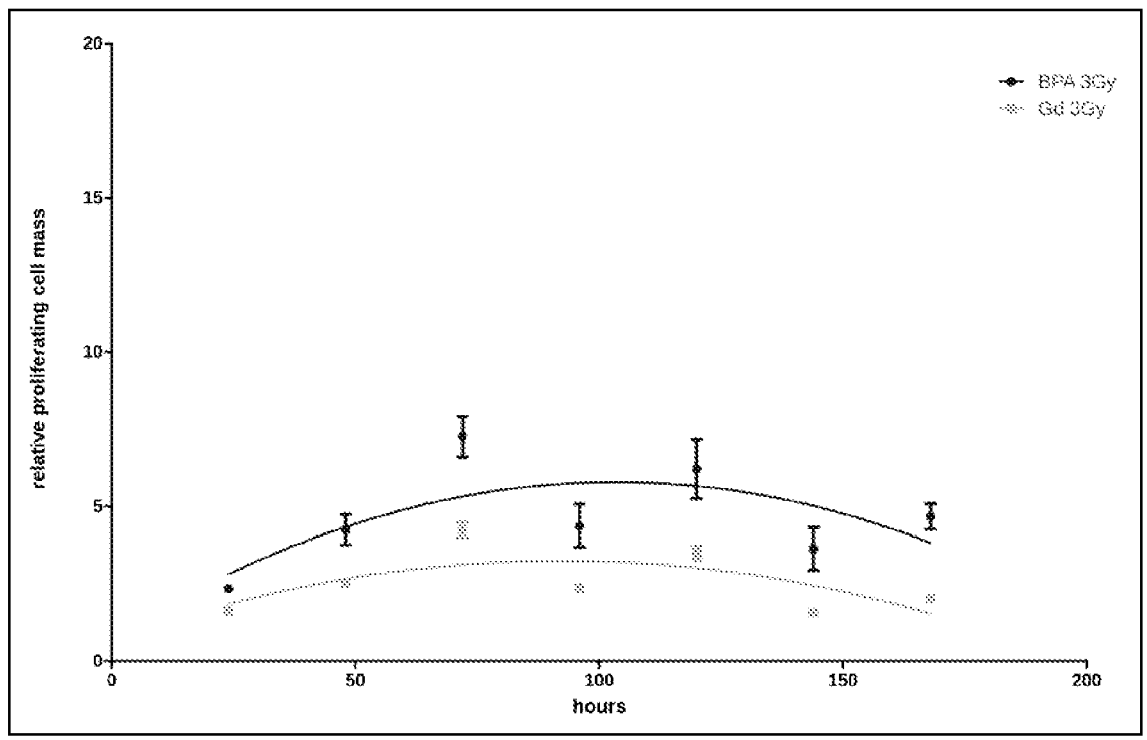
Figure 16:
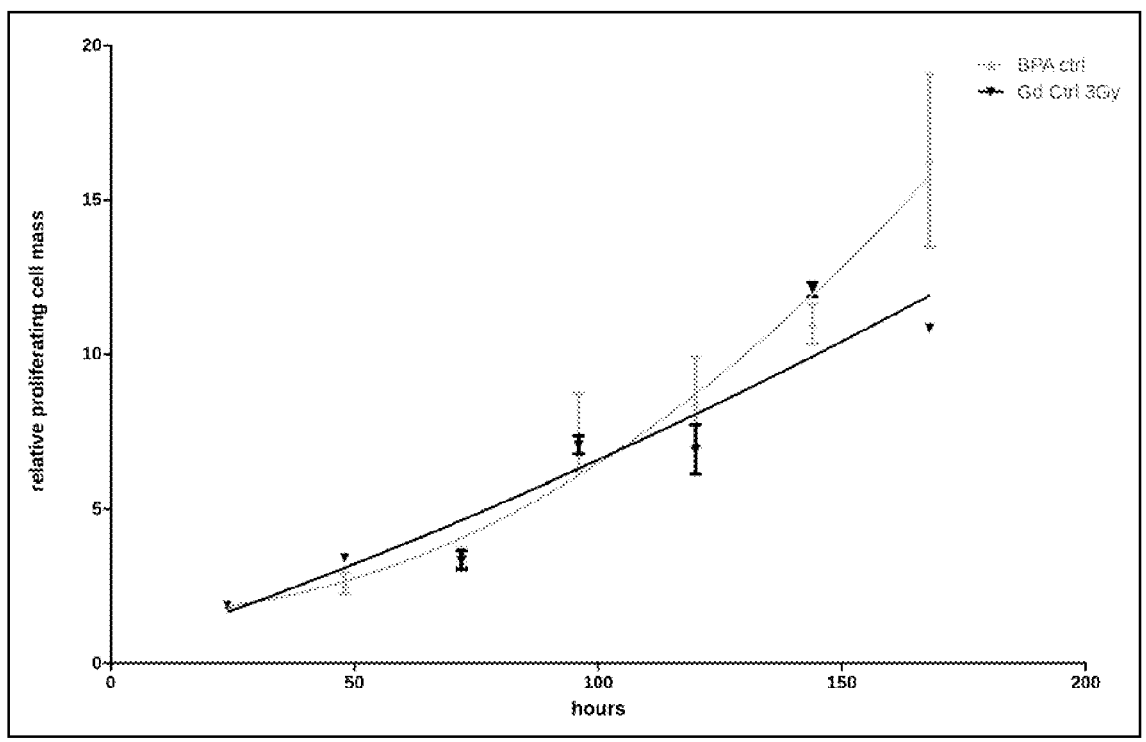
Figure 17:
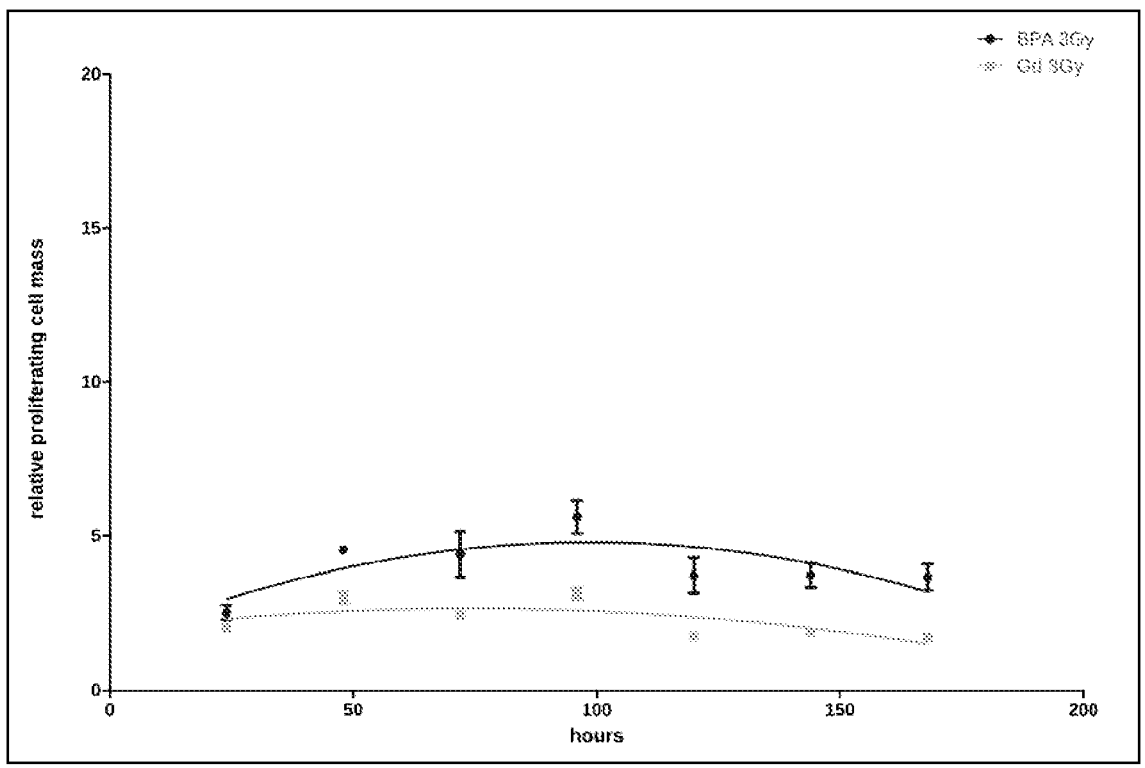

FIGS. 8A to 8F are two-dimensional thermal neutron fluence maps shown on the XY and XZ planes, intersecting with the incident beam and the point of maximum fluence, corresponding to the three-dimensional visualisations of FIGS. 7A to 7C; and FIGS. 9A to 9F are plots of thermal neutron fluence (expressed in terms of neutrons per unit area per primary and per gray of delivered dose) as a function of depth resulting from irradiation of a skull phantom by monoenergetic proton, $^{12}C$ and $^{16}O$ beams;

FIG. 10 is a view of the simulation configuration used for pencil beam thermal neutron fluence estimation in Example 2;

FIG. 11A to 11D are plots of dose distribution resulting from 1 GyE carbon ion beam treatment of a 50 mm×50 mm×50 mm volume (100-150 mm depth; discrete beam energies range from 240-300 MeV/u in steps of 6 MeV/u): FIG. 11A is an SOBP fitting (along YZ plane), FIG. 11B is a full volume rendering of dose distribution, FIG. 11C is a centre slice (XY plane), and FIG. 11D is a centre slice (YZ plane); and FIG. 12A to 12F are plots of normalised neutron fluence resulting from irradiation of the 100-150 mm target volume, in which contour lines represent fluence as a percentage of the maximum value in the slice (with shading in the 3D figures showing absolute fluence): FIG. 12A is a plot in the XY plane (proton), FIG. 12B is a plot in the XY plane (carbon), FIG. 12C is a plot in the YZ plane (proton), FIG. 12D is a plot in the YZ plane (carbon), FIG. 12E is a 3D plot (proton), and FIG. 12F is a 3D plot (carbon);

FIG. 13 is a view of an experimental configuration employed to test certain embodiments of the present invention;

FIG. 14 is a plot of T98G cell line (two flasks) proliferation over 1 week, irradiated with 3 Gy of carbon ions;

FIG. 15 is a plot of T98G cell line proliferation over 1 week, incubated with 10B-BPA (black) and 157Gd-DOTA-TPP (gray), and irradiated with 3 Gy of carbon ions;

FIG. 16 is a plot of T98G cell line (two flasks) proliferation over 1 week, irradiated with 3 Gy of helium ions;

FIG. 17 is a plot of T98G cell line proliferation over 1 week, incubated with 10B-BPA (black) and 157Gd-DOTA-TPP (gray), and irradiated with 3 Gy of helium ions;

FIGS. 18A to 18D are plots of T98G cell line cell proliferation versus time (hours) post irradiation, up to a maximum of 7 days after irradiation, for cells irradiated with 9 dose values of a carbon beam;

FIGS. 19A to 19D are plots of T98G cell line cell proliferation versus time (hours) post irradiation, up to a maximum of 7 days (168 hours) after irradiation, for cells irradiated with all 9 dose values of a helium beam (viz. 0 to 5 Gy); and FIGS. 20A to 20D present the same data as that of FIGS. 19A to 19D, respectively, but fitted with an exponential growth model.

DESCRIPTION OF EMBODIMENTS

Figure 1A:
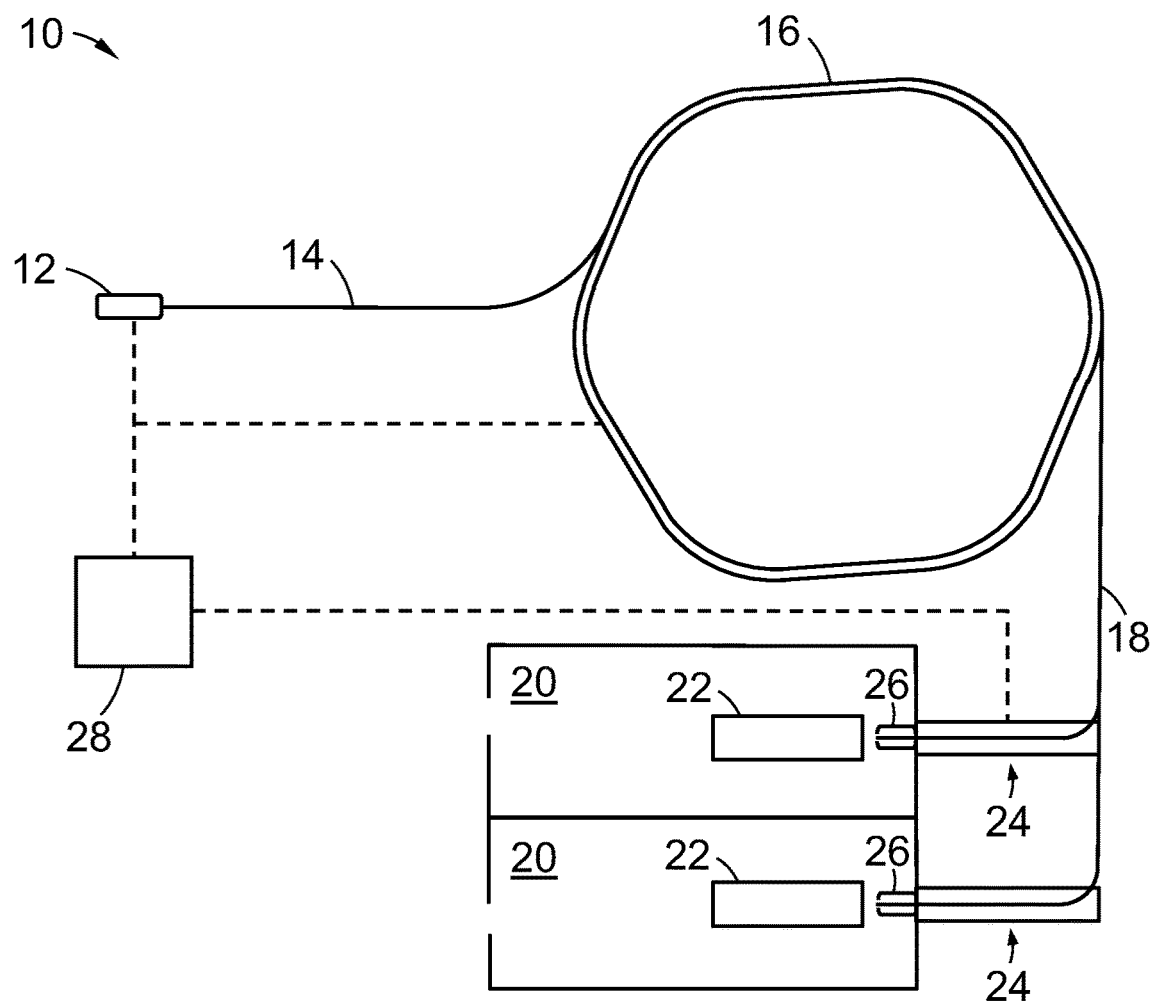
FIG. 1A is a schematic view of an irradiation system according to an embodiment of the present invention.

FIG. 1A is a schematic view of an irradiation system 10 according to an embodiment of the present invention. System 10 includes a gas supply 12 for supplying and ionizing (including decomposing where required), for example, hydrogen, helium, carbon dioxide or oxygen and thereby generate a particle beam of protons, deuterons, tritons, alpha particles, carbon ions and/or oxygen ions respectively. System 10 also includes a linear accelerator 14 that provides an initial acceleration to the particles, and a synchrotron accelerator 16 that receives the particles from linear accelerator 14 and further accelerates the particles to the desired energy.

System 10 includes an extraction beamline 18, which delivers the accelerated beam of primary particles as desired to one or more treatment rooms 20 (which include respective patient couches or gurneys 22). System 10 includes a gantry 24 at the distal ends of beamline 18. Gantry 24 includes a mechanical support structure, drive mechanism, magnets (viz. dipoles and quadrupoles), a vacuum vessel and, at the point where the beam exits (which consists of the components between a final bending magnet and an exit window to the patient), a treatment nozzle 26.

A patient on a couch 22 is located with the target tissue positioned to receive the beam that is transported by gantry 24 and exits treatment nozzle 26. The depth of penetration of the primary particles in the patient is controlled by controlling the beam energy and shape, and thereby to locate the Bragg peak of the beam as desired relative to (and within) the desired target volume.

The beam that exits treatment nozzle 26 may be controlled to irradiate the target volume in any desired pattern, such as in a spot scanning manner, a uniform scanning manner, a fast scanning manner, raster scanning manner, and/or a scatter manner. In the illustrated embodiment, the beam is raster scanned as a spot in successive planes within the target volume (the planes being perpendicular to the beam direction).

System 10 also includes a control system 28 that is controllable by a user to control the aforementioned components of system 10, including gas supply 12 (which includes an ionizer for ionizing the gas—such as hydrogen, helium or carbon dioxide—supplied by gas supply 12), linear accelerator 14, synchrotron accelerator 16, and extraction beamline 18, as well as the position and orientation of couches 22. A console (not shown) from which the user may operate control system 28 may be located in each treatment room 20 and/or at control system 28 itself. Control system 28 controls system 10 generally by reference to one or more treatment programs stored in or accessible by control system 28, and established before the commencement of treatment based on the parameters applicable to the particular patient (such as digitized X-ray computer tomography or proton tomography of the patient) and parameters derived from historical treatment, experimental and modelling/simulation data. Such parameters are typically in the form of control parameters or settings employed by control system 28 over the course of the irradiation.

Irradiation system 10 also includes a plurality of beam steering units (not shown) configured to direct the particle beam.

Control system 28 includes a particle supply controller configured to control the particle source (viz. gas supply 12), an accelerator controller configured to control linear accelerator 14 and synchrotron accelerator 16 (including to control the mean energy of the particle beam), one or more beam steering units (comprising magnets) for directing the particle beam, and an extraction controller for controlling extraction of accelerated particles from synchrotron accelerator 16. Delivery of a homogenous treatment dose to the target volume is provided by a spread out Bragg peak, which is either passively shaped (viz. by placing a ridge filter in the path of the beam), or delivered dynamically, in which a monoenergetic beam is used to 'paint' the treatment volume, slice by slice. The depth is controlled by tuning the energy of the beam and positioning the Bragg peak onto the targeted slice, while the beam is steered in the X and Y axes through the use of the magnets of the beam steering units.

Thus, control system 28 allows the delivery of the desired irradiation program, preferably in a manner that delivers a flat biological dose to the target volume through (in this embodiment) spot scanning, raster scanning or passively scattered delivery. Control system 28 can also be used to plan an irradiation program, such as by the irradiating of a phantom; an irradiation program can also be prepared by simulation of the desired irradiation.

Figure 1B:
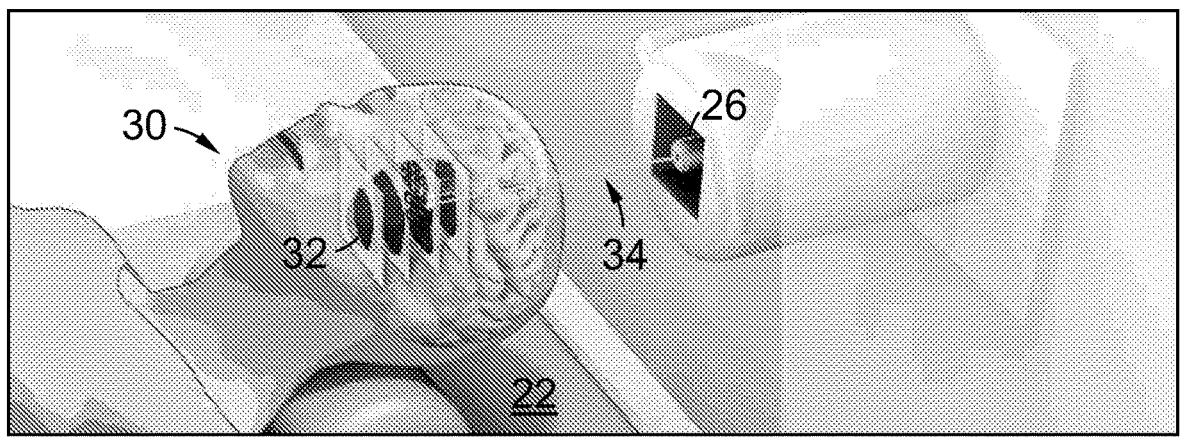
FIG. 1B is a schematic view of a patient recumbent on a couch of the irradiation system of FIG. 1A having a tumour irradiated by a beam of particles generated by the irradiation system.

FIG. 1B is a schematic view of a patient 30 recumbent on a couch 22 and having a tumour 32 irradiated by the beam 34 generated by system 10.

In use, the patient is administered with a dose of a thermal neutron absorbing nuclide such as a composition containing $^{157}$Gd and/or $^{10}$B that is preferentially absorbed by the tumour 32. The target volume containing the tumour 32 is then irradiated with the beam 34 of primary particles (viz. protons, helium, carbon ions, etc) in the desired scan pattern, depth, duration, beam energy, etc (according to the treatment program established earlier). This may include moving the couch 22—and hence the target volume—between or during the period of irradiation. However, patient movement is generally minimized as it can introduce time delays and may result in large target volume misalignment and positioning errors; in most cases, gantry 24—or the particle transport line supported thereby—is rotated around an axis (or multiple axes) instead.

During irradiation, a fraction of the primary particles in beam 34 undergo non-elastic collisions with nuclei in the tumour 32. This results in the production of a range of nuclear fragments at the target site, including short-range, high-LET charged particles and neutrons which are emitted from the point of collision, and which deposit their energy in the region surrounding the path of the incident primary beam 34. The neutrons may then be absorbed by the thermal neutron absorbing nuclide of the administered composition, resulting in the production of energetic charged particles with high relative biological effectiveness.

Figure 2:
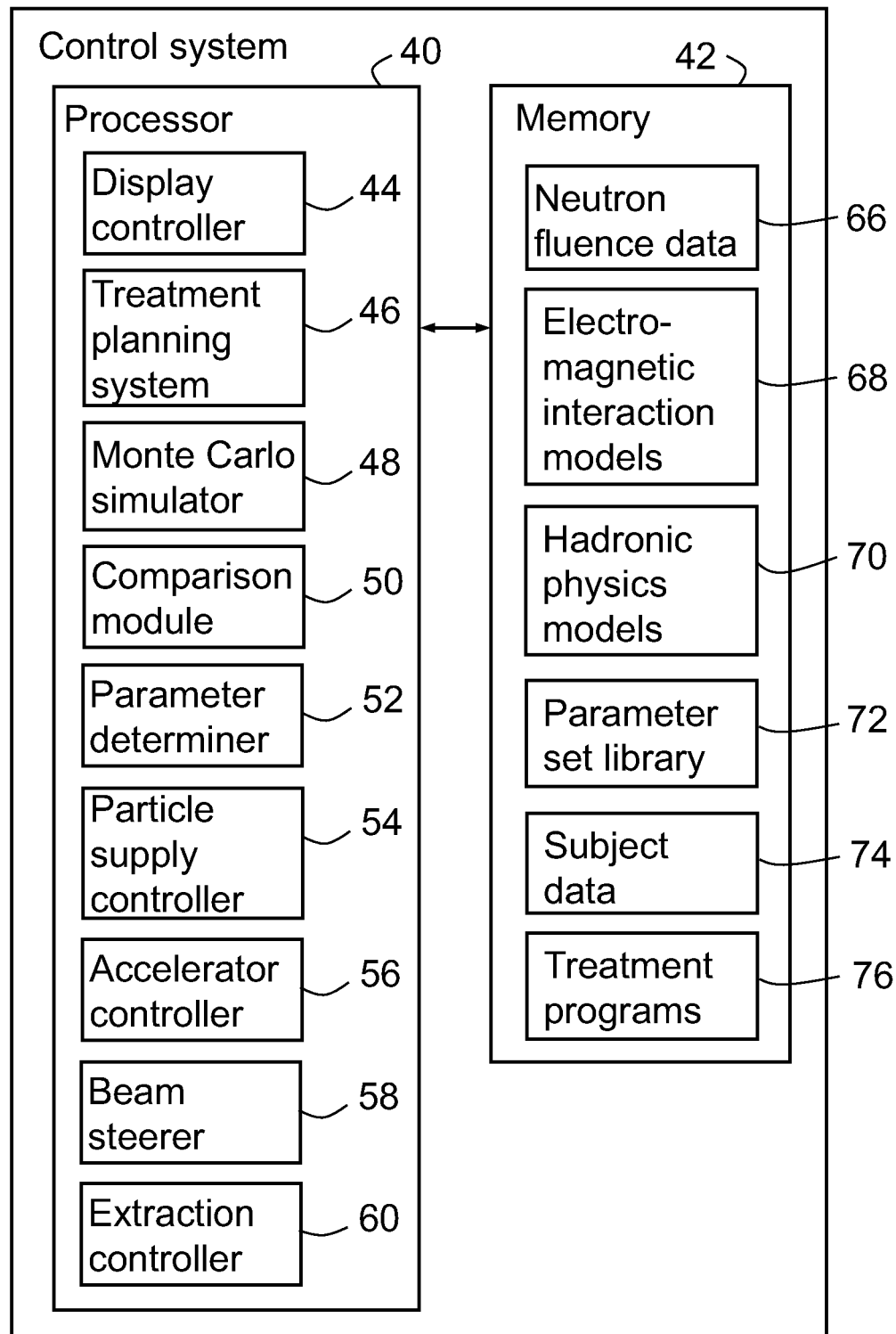
FIG. 2 is a schematic view of the control system of the irradiation system of FIG. 1A.

FIG. 2 is a more detailed schematic view of control system 28 of irradiation system 10. Control system 28 is typically implemented as a computer (or other computing device), in communication with those components of irradiation system 10 that are controlled by or from control system 28.

Control system 28 combines the simulation of the method implemented by irradiation system 10, generation and validation of irradiation parameters, and the control of irradiation system 10, but it will be appreciated that these may be implemented separately. For example, it may be desirable to implement simulation of the method off-line; likewise, the generation and validation of irradiation parameters may also be conducted off-line, the resulting parameters then loaded into or otherwise made accessible to control system 28.

Referring to FIG. 2, control system 28 includes a processor 40 and memory 42. Processor 40 implements several components, including a display controller 44, a treatment planning system 46, a Monte Carlo simulator 48, a comparison module 50, a parameter determiner 52, a particle supply controller 54, an accelerator controller 56, a beam steerer 58 and an extraction controller 60.

It will be appreciated that other standard components (such as a user interface, I/O bus and the like) have been omitted for clarity.

Display controller 44 controls the display of parameters, images and control panels to the display of a user interface (not shown) of control system 28. Treatment planning system 46 is configured to receive standard irradiation parameters adapted for irradiation system 10, a desired biological effective dose distribution for the tissue (e.g. tumour), empirical models (e.g. phantom simulations and experiments), and subject data (specific to a particular subject or patient, so typically including CT/MR data or other medical imaging data), and to generate a specific irradiation or treatment program. Monte Carlo simulator 48 is adapted to simulate the irradiation provided by irradiation system 10, for the purposes of evaluating a proposed irradiation plan, and of preparing new irradiation plans, including simulating the relevant phantom.

Comparison module 50 is configured to compare an irradiation plan simulated by Monte Carlo simulator 48 with the specific irradiation or treatment program outputted by treatment planning system 46, in particular by comparing the resulting total biological effective dose distribution. Monte Carlo simulator 48 also uses the relevant subject data. The results are provided to parameter determiner 52, which modifies or refines the parameters employed by Monte Carlo simulator 48 according to any difference between the results of the simulation and the desired irradiation, and generates new or modified parameters adapted to bring the simulation more closely into conformity with the desired irradiation (a procedure that may be conducted incrementally/iteratively).

Particle supply controller 54 is configured to control source 45 of irradiation system 10, accelerator controller 56 is configured to control accelerator 16 of irradiation system 10 (including linear accelerator 14), beam steerer 58 is configured to control one or more beam steering units of irradiation system 10, and extraction controller 60 is configured to control the extraction of accelerated particles from accelerator 16.

Memory 42 includes empirical reaction validation data in the form, in this example, of neutron fluence data 66, electromagnetic interaction models 68 for use by Monte Carlo simulator 48 when modelling electromagnetic interactions, and Hadronic physics models 70 for use by Monte Carlo simulator 48 when modelling radioactive decay, particle decay, hadron elastic collisions, ion inelastic collisions, neutron capture, neutron inelastic collisions and proton inelastic collisions.

Memory 42 also stores a parameter set library in the form, in this example, of a particle therapy parameter library 72, including duration of irradiation by the beam 34, the composition and energy of beam 34, the peak radiobiological effectiveness of the particles of beam 34, the physical dose deposition of the particles of beam 34, the composition to be administered to the subject and its dose distribution, the fluence of the neutrons produced in the specific irradiation configuration, the target volume position relative to the beam 34, and the therapeutic parameters of the ions constituting beam 34.

Memory 42 also includes subject data 74 pertaining to one or more subjects or patients (which typically includes, in medical applications, image data pertaining to the subject), and irradiation programs in the form, in this example, of treatment programs 76, also pertaining to one or more subjects or patients.

Example 1

To demonstrate the viability of this approach, the generation of the neutrons under proton or heavy ion irradiation, and the absorption of those neutrons by a composition containing $^{10}$B, was simulated using Monte Carlo techniques. This was done to determine the neutron fluence that would be generated by typical forms of proton or heavy ion irradiation, and hence the applications to which that neutron fluence could be put.

I. Materials and Methods

All Monte Carlo simulations were performed using the Geant4 toolkit (version 10.2.p03) [23, 24]. Electromagnetic interactions were modelled using the standard Geant4 physics option 3 model (G4EmStandardPhysics option3), while the hadronic physics models used in the simulations are listed in Table I.

TABLE I

Hadron physics models used in all simulations

| Interaction | Energy Range | Geant4 Model |
| --- | --- | --- |
| Radioactive Decay | N/A | G4RadioactiveDecayPhysics |
| Particle Decay | N/A | G4Decay |
| Hadron Elastic | 0-100 TeV | G4HadronElasticPhysicsHP |
| Ion Inelastic | 0-110 MeV | Binary Light Ion Cascade |
|  | 100 MeV-10 GeV | QMDModel |
|  | 9.99 GeV-1 TeV | FTFP |
| Neutron Capture | 0-20 MeV | NeutronHPCapture |
|  | 19.9 MeV-100 TeV | nRadCapture |
| Neutron Inelastic | 0-20 MeV | NeutronHPInelastic |
|  | 19.9 MeV-9.9 GeV | Binary Cascade |
| Neutron Elastic | 0-20 MeV | NeutronHPElastic |
|  | 20 MeV-100 TeV | hElasticCHIPS |
| Proton Inelastic | 0-9.9 GeV | Binary Cascade |

Section I B (below) examines the three-dimensional distribution of the thermal neutron fluence (both per primary particle and per Gy delivered to the Bragg Peak) resulting from irradiation of a homogeneous poly(methyl methacrylate) phantom (PMMA) with monoenergetic proton, $^{12}$C and $^{16}$O beams with different energies; Section I C (below) describes how this fluence distribution can be used to calculate the increase in dose attributable to boron capture of the generated thermal neutrons.

A. Simulation and Analysis Configuration

Figure 3:
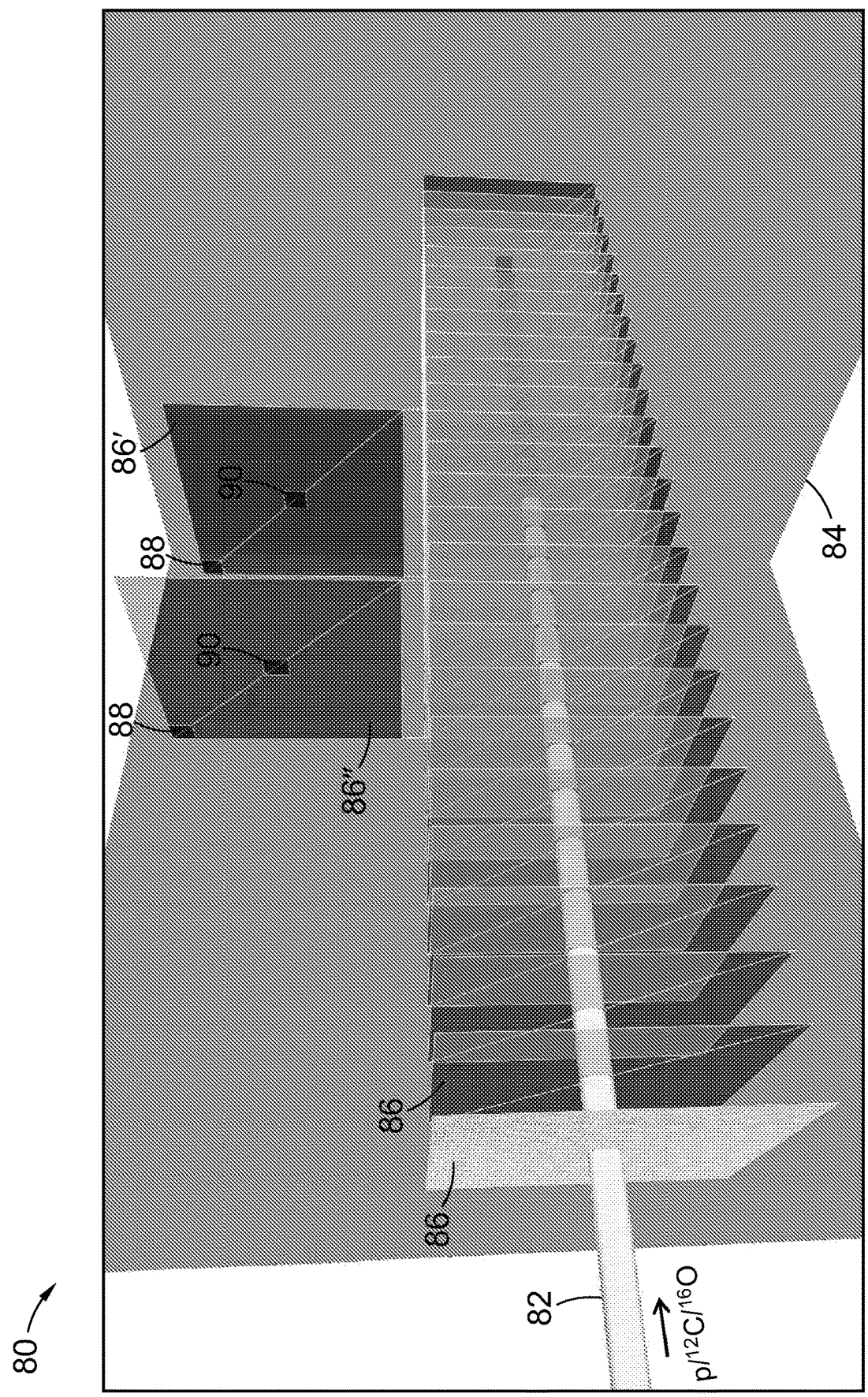
FIG. 3 is a schematic view of the simulation configuration used for thermal neutron fluence and spectra estimation in Example 1.
Figure 4A:
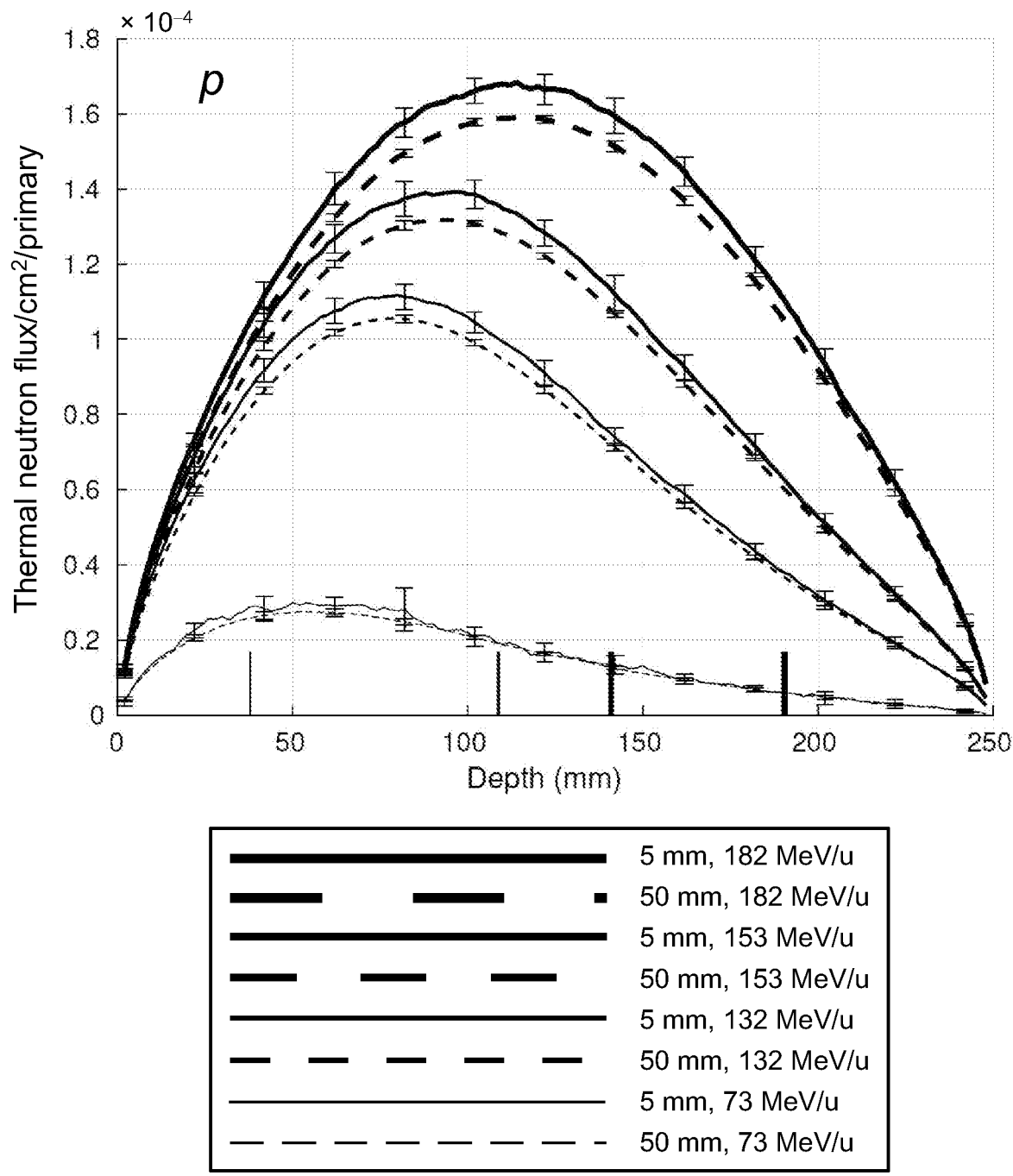
FIGS. 4A to 4F are plots of thermal neutron fluence (expressed in terms of neutrons per unit area per primary and per gray of delivered dose) as a function of depth resulting from irradiation of a PMMA phantom by monoenergetic proton, $^{12}C$ and $^{16}O$ beams.
Figure 4B:
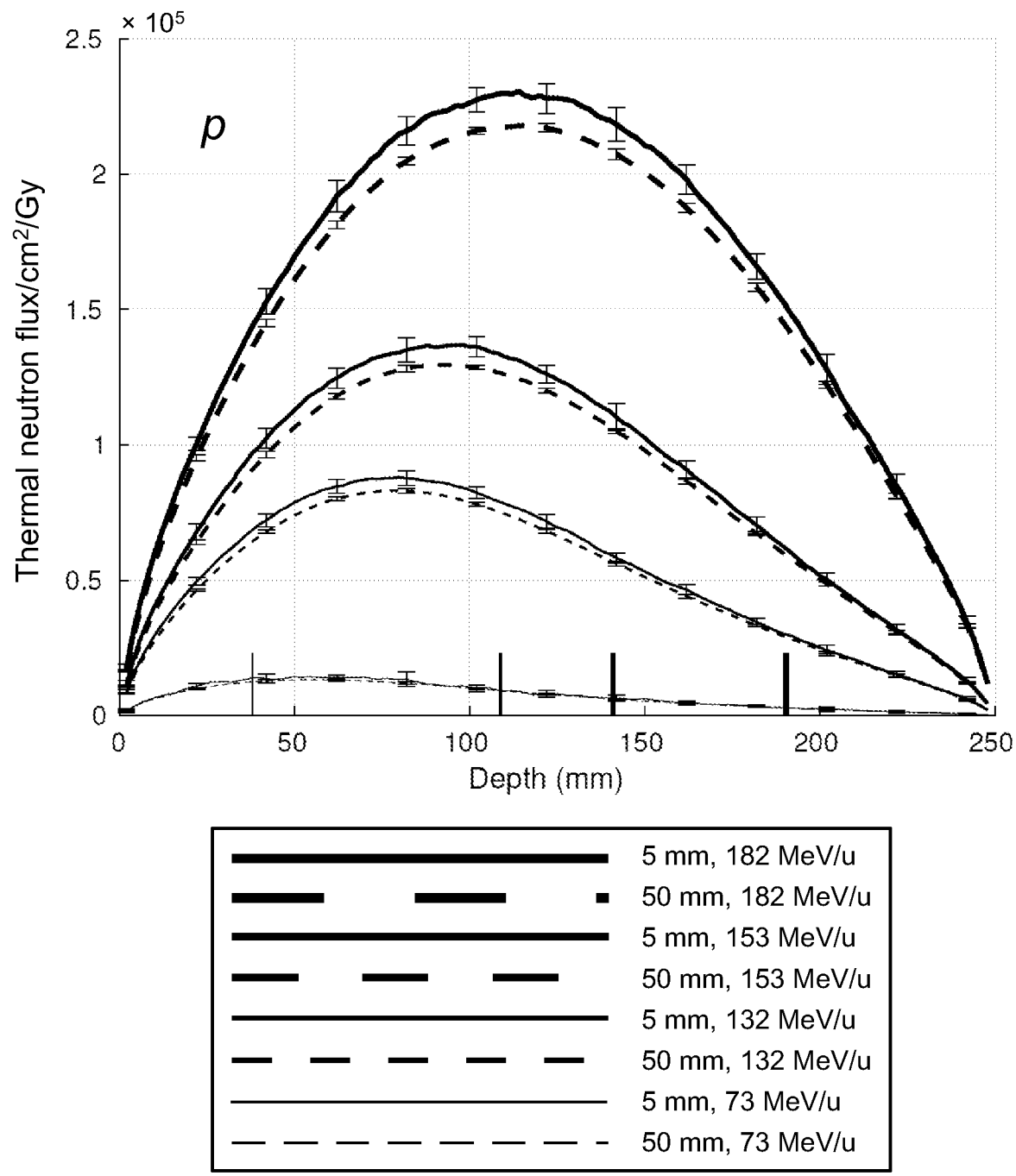
Figure 4C:
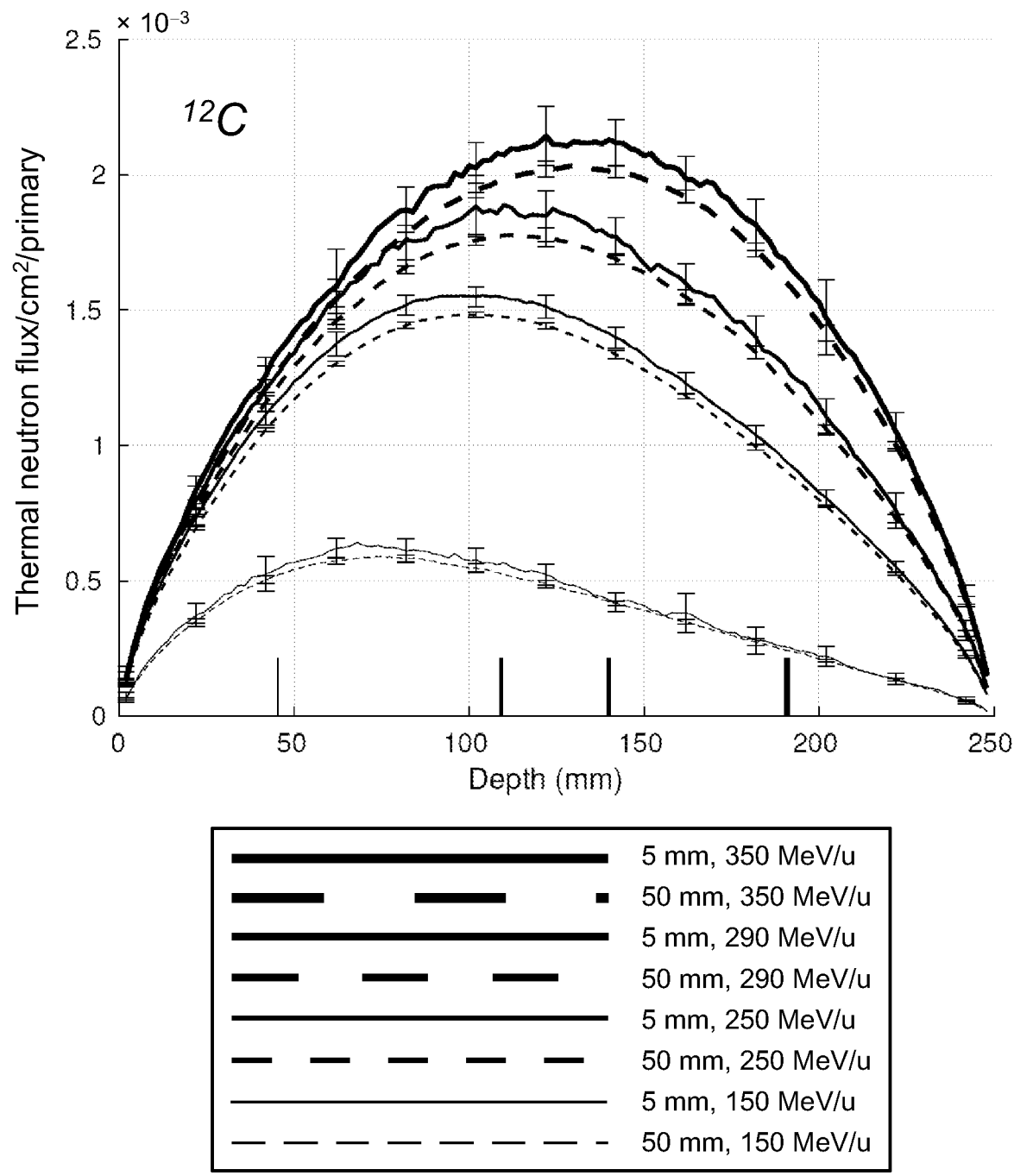
Figure 4D:
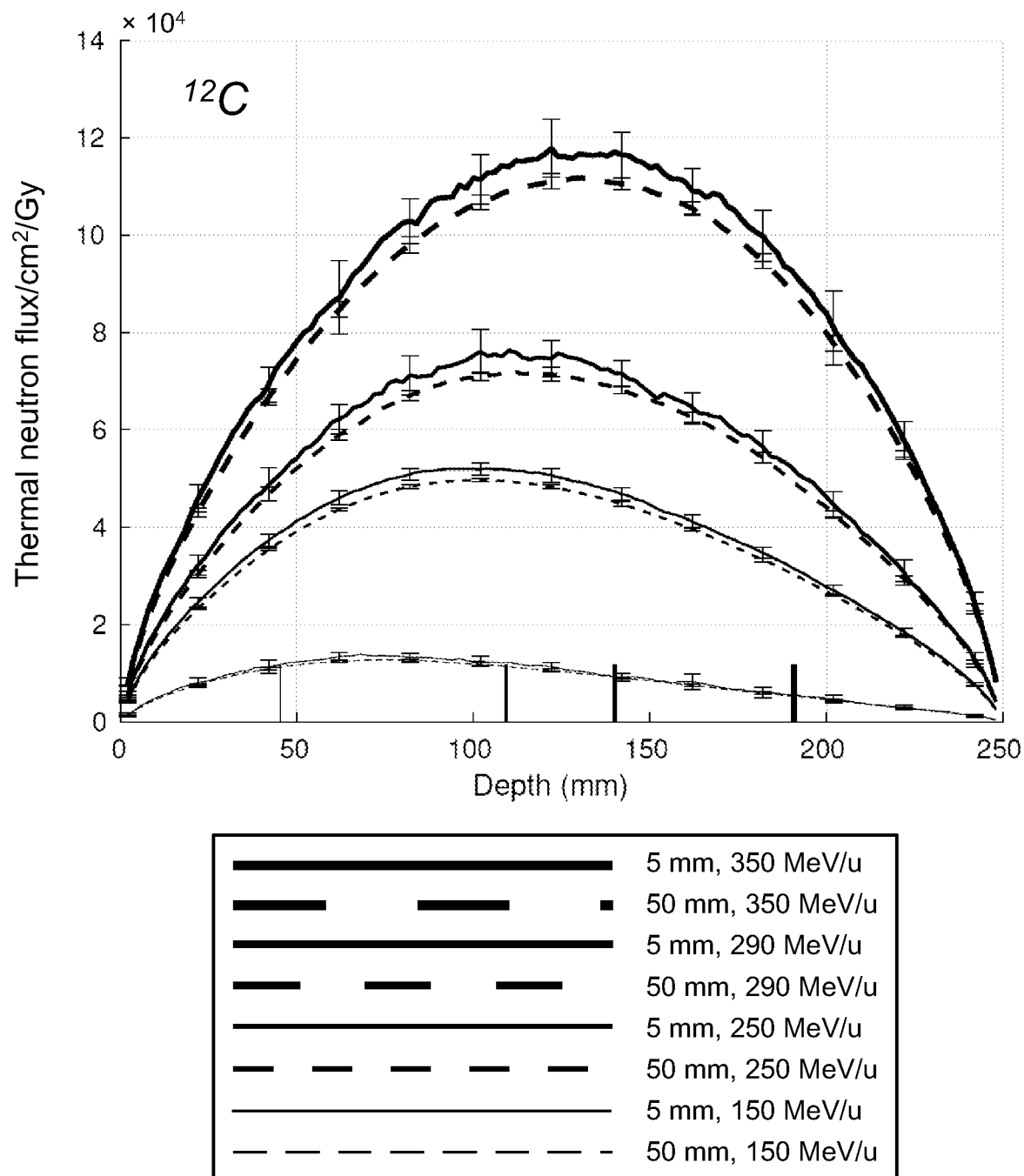
Figure 4E:
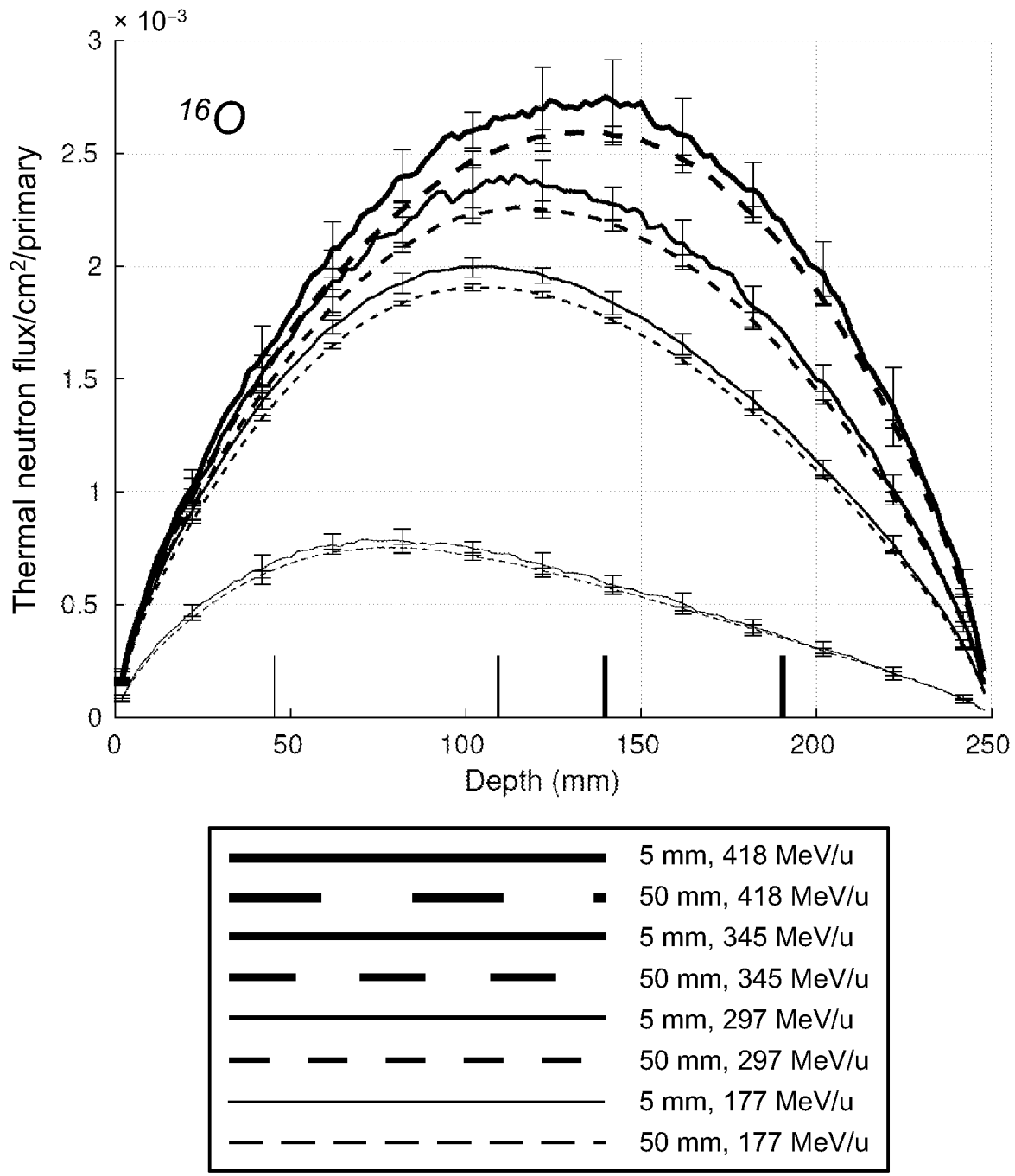
Figure 4F:
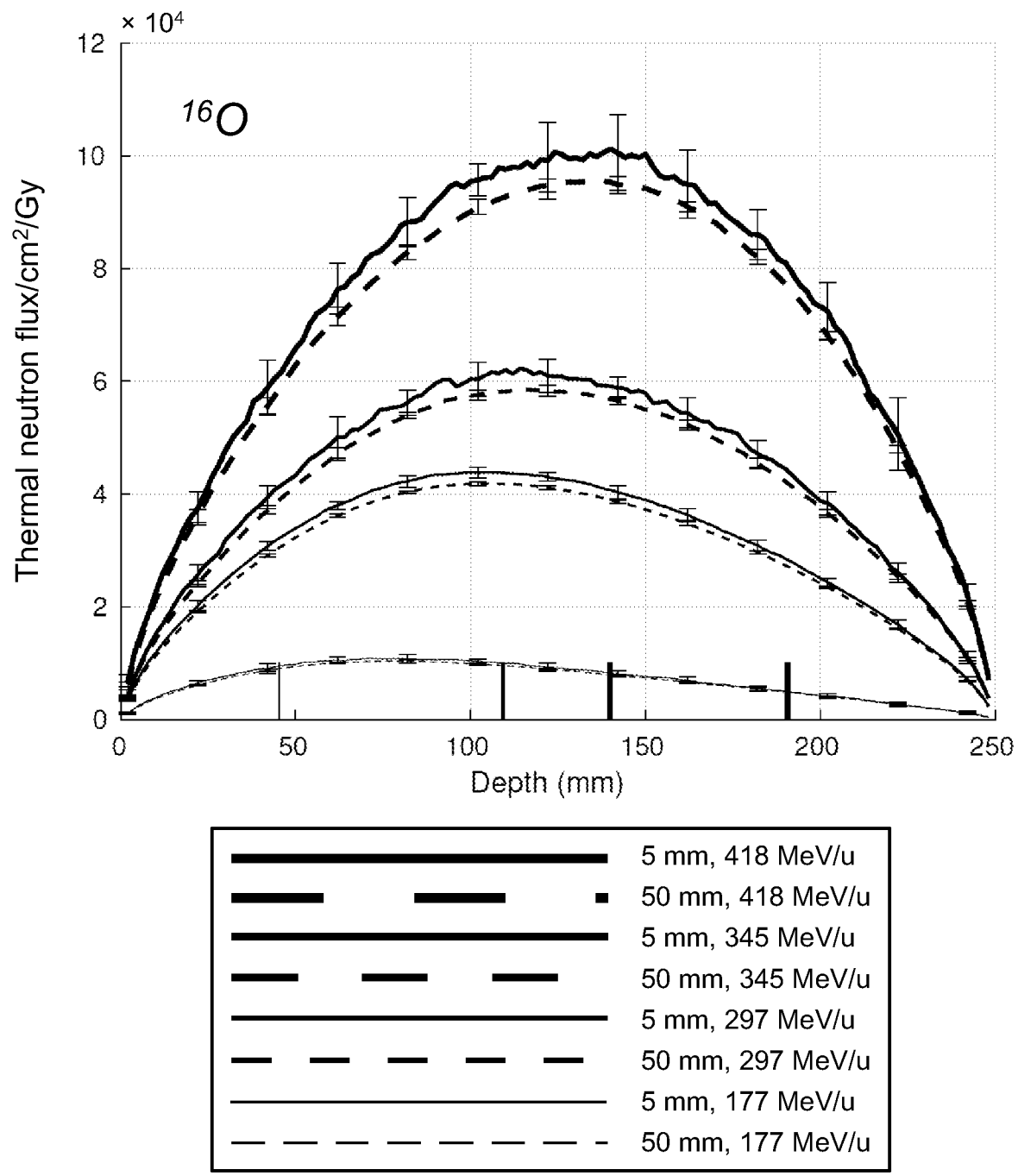

The Geant4 simulation and analysis configuration is shown schematically generally at 80 in FIG. 3. Referring to FIG. 3, monoenergetic beams 82 of protons, $^{12}$C ions and $^{16}$O ions, respectively, with a rotationally symmetric 5 mm FWHM Gaussian beam profile, were directed in the simulations perpendicularly towards the surface of a simulated homogeneous PMMA phantom 84 of 250 mm×250 mm×250 mm.

One hundred and twenty-five parallel neutron fluence quantisation planes 86 (each of 50 mm×50 mm) were defined every 2 mm along the path of beam 34 within PMMA phantom 84, normal to the beam and centred on the beam axis (though only ever fifth quantisation plane is shown in FIG. 3 for clarity).

Four reference primary beam energies were chosen for the $^{12}$C beam, resulting in Bragg peak depths in PMMA of between 4 cm and 20 cm. Beam energies were then calculated for the proton and $^{16}$O beams such that their Bragg peaks were located at approximately the same depths. The full set of beam energies for each primary particle type and the corresponding locations of Bragg peaks in each phantom are listed in Table II.

TABLE II

Primary energies of the beams at the surface of the PMMA phantom and the location of the point of maximum dose deposition (Bragg peak)

| Particle | Energies (MeV/u) | Depths of Bragg Peaks (mm) |
|---|---|---|
| Proton (p) | 73.0, 132, 153, 182 | 38.0, 109, 141, 191 |
| $^{12}$C | 150, 250, 290, 350 | 45.0, 109, 140, 191 |
| $^{16}$O | 177, 297, 345, 418 | 45.0, 109, 140, 191 |

The simulated phantom was a 250 mm×250 mm×250 mm cube of PMMA (poly(methyl methacrylate)), with physical properties taken from the National Institute of Standards and Technology (NIST) database [25].

B. Thermal Neutron Fluence Estimation

The conventional definition of neutron fluence is the number of neutrons traversing a unit area (n/cm$^2$), but a more useful measure of fluence in this instance is neutrons per unit area per primary particle or per gray of delivered peak dose, since these express fluence in terms of heavy ion therapeutic parameters, while being independent of the intensity of the primary beam. Importantly, this definition conveniently allows the effect of the neutron field for boron neutron capture dose enhancement to be predicted, based on assumed achievable tissue concentrations of boron and heavy ion treatment parameters.

The thermal neutron fluence (as defined above) resulting from heavy ion irradiation of the phantom was evaluated at each of planes 86. Each plane 86 was scored with a spatial resolution of 1 mm×1 mm. Fluence was calculated over the central 5 mm×5 mm area of each plane and over the whole 50 mm×50 mm plane, for all planes 86.

Additionally, the fluence was also calculated over the 5 mm×5 mm area at the extreme top-left corner of both the plane 86' closest to the Bragg peak and also the plane 86" passing through the region of maximum neutron fluence. The ratio between the fluence measured in the top-left corner 88 and centre 90 of each of these planes 86', 86" was calculated to assess the uniformity of the neutron field in planes 86', 86".

To obtain an estimate of the thermal neutron fluence per unit dose, the dose deposited at the Bragg peak was also estimated. A 5 mm×5 mm×5 mm sensitive volume centred at the Bragg peak was defined, and the energy deposited was scored and converted to dose. This was then used as a conversion factor to calculate the thermal neutron fluence per unit dose.

A simple variance analysis method was used to estimate the minimum number of primary particles to use in the simulations. A series of test simulations were conducted, each with M=50 runs of N(k)=2k N$_0$, N$_0$=1×10$^5$ primary particles. Thermal neutron fluence was calculated for each simulation within a test area centred on the Bragg peak, and the mean and standard deviation (SD) calculated across the M simulations. The inter-run standard deviation should approach zero as N(k) tends to infinity; accordingly, the experiment was repeated with progressively larger values of k until the ratio of inter-run standard deviation to mean was less than an arbitrary threshold of 5%. This analysis suggested that N=5×10$^7$ incident protons and N=5×10$^6$ $^{12}$C and $^{16}$O ions would be sufficient to obtain a satisfactory estimate of thermal neutron fluence (99% probability of the estimated fluence being within ±5% of the true fluence).

C. Quantification of Neutron Capture Dose Enhancement

To estimate the order of magnitude of the achievable overall boost to the biological dose in the treatment region, and thereby evaluate the feasibility and potential benefit of neutron-capture enhanced particle therapy, a simple treatment plan was implemented to convert the estimated thermal neutron fluence (n/cm$^2$/Gy) to the total number of thermal neutrons (N$_{th}$) generated within the treatment volume. In this software implementation, spread out Bragg peaks were simulated as the superposition of plural, pristine Bragg peaks, and the corresponding neutron fluence was estimated using the result of simulated scored neutron fluences for a number of monoenergetic beams.

Two cubic 50 mm×50 mm×50 mm target volumes were defined within the phantom, centred at depths of 125 mm and 175 mm along the axis of the beam.

Each target volume was divided into a series of ten slices, each 5 mm thick and further divided into a 10×10 grid, resulting in a total of one thousand 5 mm×5 mm×5 mm voxels. The treatment dose was delivered slice by slice. Once the planned particle dose in each voxel was achieved, the beam was translated to the next voxel.

After irradiation of each slice, the beam energy was changed to reduce the depth of the Bragg peak for treatment of the next slice. The process was repeated until the whole target volume had been treated. For simplicity, the plan did not account for the dose resulting from the build-up part of the particle dose deposition profile; although this would be essential in designing a real treatment plan, for the purpose of determining the feasibility of the proposed scheme, it was sufficient to assume that all energy is delivered at the Bragg peak.

For a planned treatment dose, the total number of thermal neutrons in each voxel within the target volume was evaluated by summing the fluence per gray (n/cm$^2$/Gy) as the beam was stepped through all planned positions within the target volume, multiplied by the planned physical dose at each position:

$$n_{i,j,k} = \sum_{l=1}^{10} \sum_{m=1}^{10} \sum_{n=1}^{10} D_{l,m,n} \times \phi_{[(i-l),(j-m),(k-n)],d_n} \cdot \delta A$$

where $n_{i,j,k}$ is the total number of thermal neutrons traversing the voxel at location (i, j, k), $D_{l,m,n}$ is the physical dose delivered to a voxel with coordinates (l, m, n), $\phi_{[(i-l),(j-m),(k-n)],d_n}$ is the fluence (expressed in neutrons per square centimetre per gray) at (i, j, k), contributed by the beam at positioned at (l, m, n) and $\delta A$ is the voxel surface area. The fluence $\phi$ takes an additional argument to explicitly express the fact that the shape of the neutron fluence distribution is dependent on the Bragg peak depth $d_n$; as only a limited number of beam energies were simulated, the fluence distributions were linearly interpolated/extrapolated for other Bragg peak depths. This is a first order approximation and is sufficient for order-of-magnitude calculations needed for this evaluation.

The total number of thermal neutrons (Nth) generated within the full target volume resulting from the delivery of the entire planned treatment dose was then calculated by summing the total number of thermal neutrons traversing all voxels within the target volume:

$$N_{th} = \sum_{i_1=1}^{10} \sum_{j_1=1}^{10} \sum_{k_1=1}^{10} n_{i,j,k}$$

The total absorbed dose in each voxel of the treatment volume is the sum of the physical dose delivered by the primary proton or heavy ion beam, $D_P$, and the boron neutron capture dose, which results from the boron neutron capture reaction ($^{10}B(n, \alpha)^7Li$) occurring within the target volume, $D_B$. This latter reaction is the dominant means by which thermal neutrons deposit energy in tissue bearing high concentrations of boron [26, 27]. The total weighted biological dose, $D_w$ was then estimated through the incorporation of the RBE and composition biological effectiveness (CBE) of each component, and expressed in photon-equivalent-dose (Gy-Eq) [28]:

$$D_w = RBE_P \times D_P + CBE \times D_B$$

where $RBE_P$ is the relative biological effectiveness of particle P, and $D_P$ and $D_B$ are the primary particle and boron neutron capture physical dose components (in gray), respectively. RBE is assumed to be 1.1 for protons ($RBE_H=1.1$), 3.04 for carbon and oxygen at the Bragg peak ($RBE_{ion,BP}$), 2.5 for carbon and oxygen at the centre of a spread out Bragg peak with a width of 5 cm ($RBE_{ion}$) [28]. CBE is assumed to be 3.8 for tumour tissue [22, 28].

The estimated number of thermal neutrons was then used to estimate boron physical dose:

$$D_B = N_{th} \times C_a \times N_B$$

where $C_a=6.933 \times 10^{-14}$ is the neutron fluence-to-dose conversion factor for $^{10}B$ reaction (Gy/cm$^2$/ppm), and $N_B$ is the $^{10}B$ concentration (parts per million) [29].

A range of boron concentrations have previously been reported in the literature. Concentrations, together with the ratio of concentration in tumours to healthy tissue, are listed in III.

The boron neutron capture dose is calculated for a photon-equivalent-dose of 100 Gy-Eq delivered by proton, $^{12}C$ and $^{16}O$ beams to both target volumes, with four different concentrations of $^{10}B$.

TABLE III

Boron-based neutron capture agent concentrations and the ratios of tumour to healthy tissue concentrations reported in the literature.

| Reported by | Method | Compound | Target | Concentration (PPM) | Concentration ratio |
|---|---|---|---|---|---|
| Barth et al., 2012 [14] | Intravenous infusion | BPA | Brain | 30 ± 12 | 5:1 |
| Luderer et al., 2015 [30] | Convection enhancement | BPA | Brain | 68.3 ± 17.9 | 8:1 |
| Alkins et al., 2013 [31] | Ultrasonic enhancement | BPA | Brain | 123 ± 25 | 6.7:1 |
| Suzuki et al., 2004 [39] | Inter-arterial infusion | BSH + lipidol | Liver | 200 (6 h) | 3.6:1 (1 h), 14.9:1 (6 h) |
| Suzuki et al., 2004 [39] | Inter-arterial infusion | BSH + degradable starch microspheres | Liver | 231 (1 h) | 1.4:1 (1 h), 1.1:1 (6 h) |
| Koganei et al., 2013 [32] | Intravenous infusion | BSH-encapsulating 10% DSBL liposomes | Colon | 174 ± 20 | 1.2:1-3.5:1 |

It is also envisaged that $^4$He will be a suitable heavy ion, as would the radioactive isotopes of the other heavy ions discussed herein; deuterium and tritium may also be suitable in some applications. Ions heavier than oxygen have shown to reach their maximum RBE prior to their maximum dose deposition point (BP), making them less suitable for use in therapy than 16O and lighter ions.

II. Results

A. Neutron Flux

FIGS. 4A to 4F show simulated thermal neutron fluence plotted as a function of depth in PMMA phantom 84 for monoenergetic proton, $^{12}$C and $^{16}$O beams at each of the four beam energies used with each ion species. In FIGS. 4A to 4F, fluence is expressed in units of neutrons per square centimetre per primary particle and per gray of ion dose. Flux is averaged over square 5 mm×5 mm and 50×50 mm² regions normal to the beam and centred on the beam axis; results averaged over the full 50 mm×50 mm planes and over the central 5 mm×5 mm region of each plane only are indicated with solid lines and dashed lines, respectively. For clarity, 95% confidence intervals (±2σ) are shown only every 20 mm; inter-run fluence variations at any given depth are distributed approximately normally. The location of each Bragg peak is displayed as a solid vertical marker attached to the horizontal axis, with its width matching that of the corresponding fluence-depth curve.

Figure 5A:
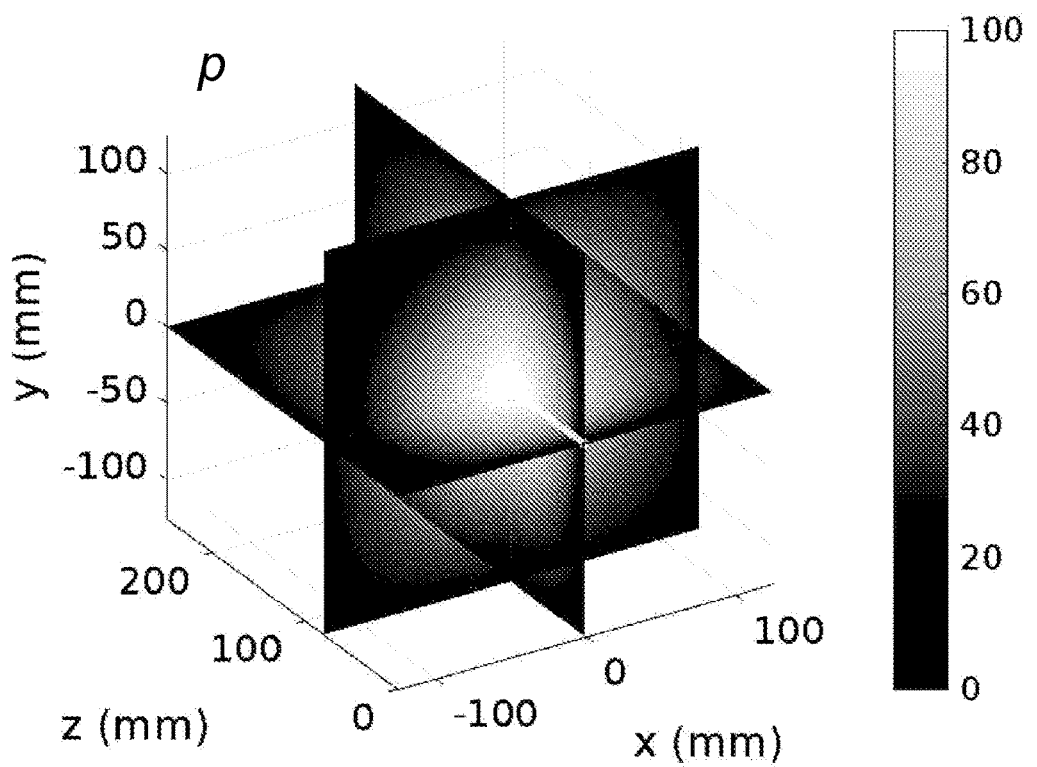
FIGS. 5A to 5C are three-dimensional visualisations of the thermal neutron distribution resulting from irradiation of the PMMA phantom by monoenergetic 132 MeV/u, 153 MeV/u and 182 MeV/u proton beams, normalised per primary particle.
Figure 5B:
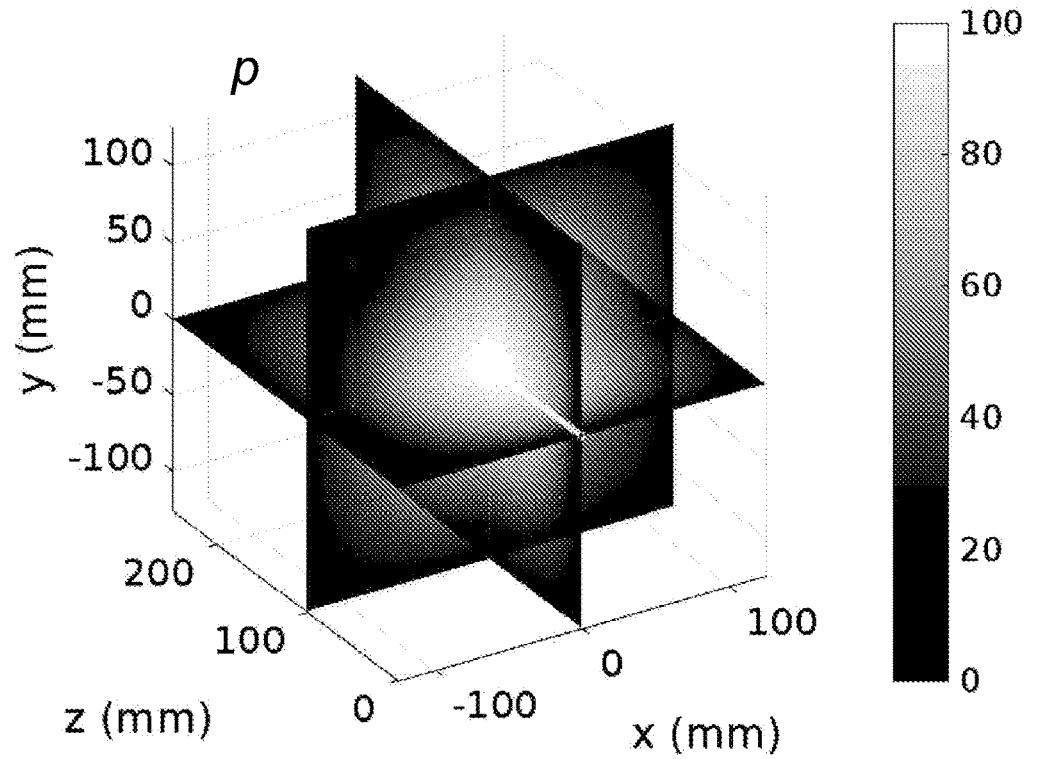
Figure 5C:
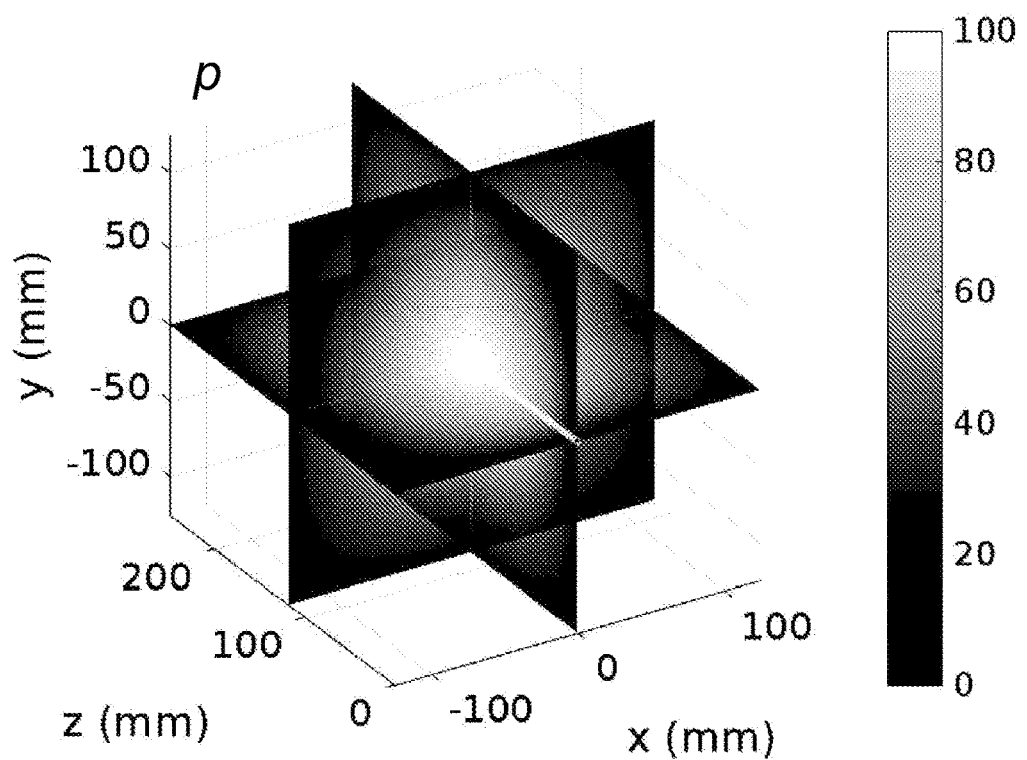
Figure 6A:
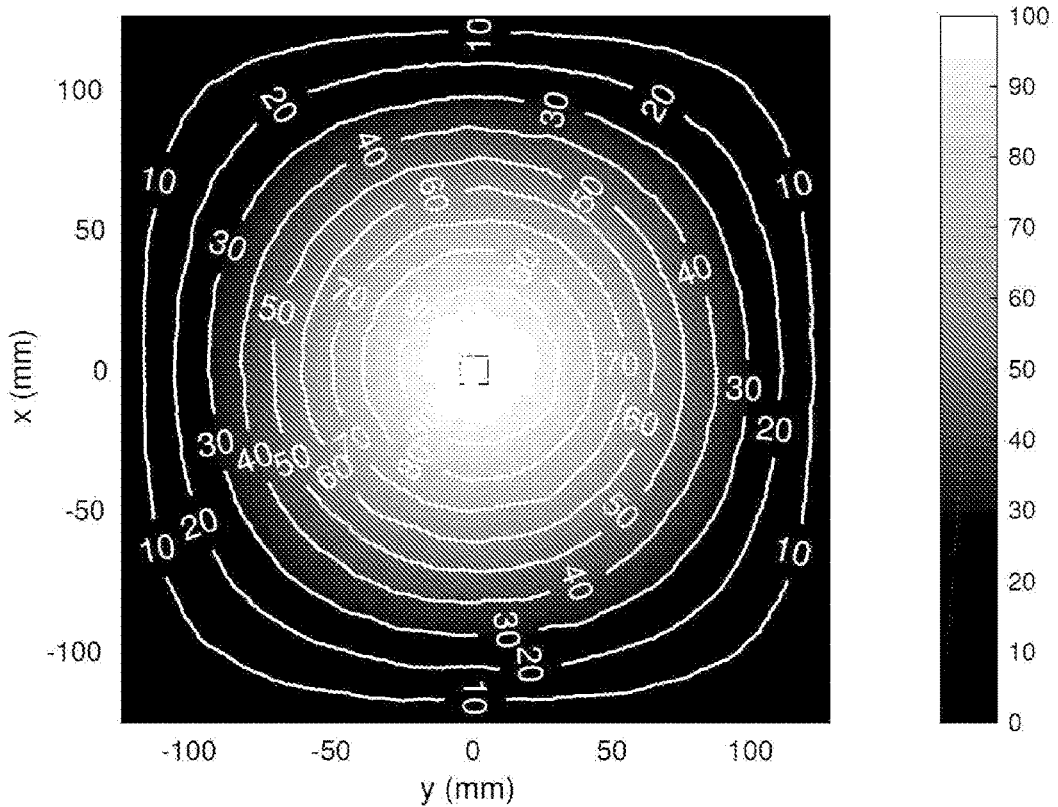
FIGS. 6A to 6F are two-dimensional thermal neutron fluence maps shown on the XY and XZ planes, intersecting with the incident beam and the point of maximum fluence, corresponding to the three-dimensional visualisations of FIGS. 5A to 5C.
Figure 6B:
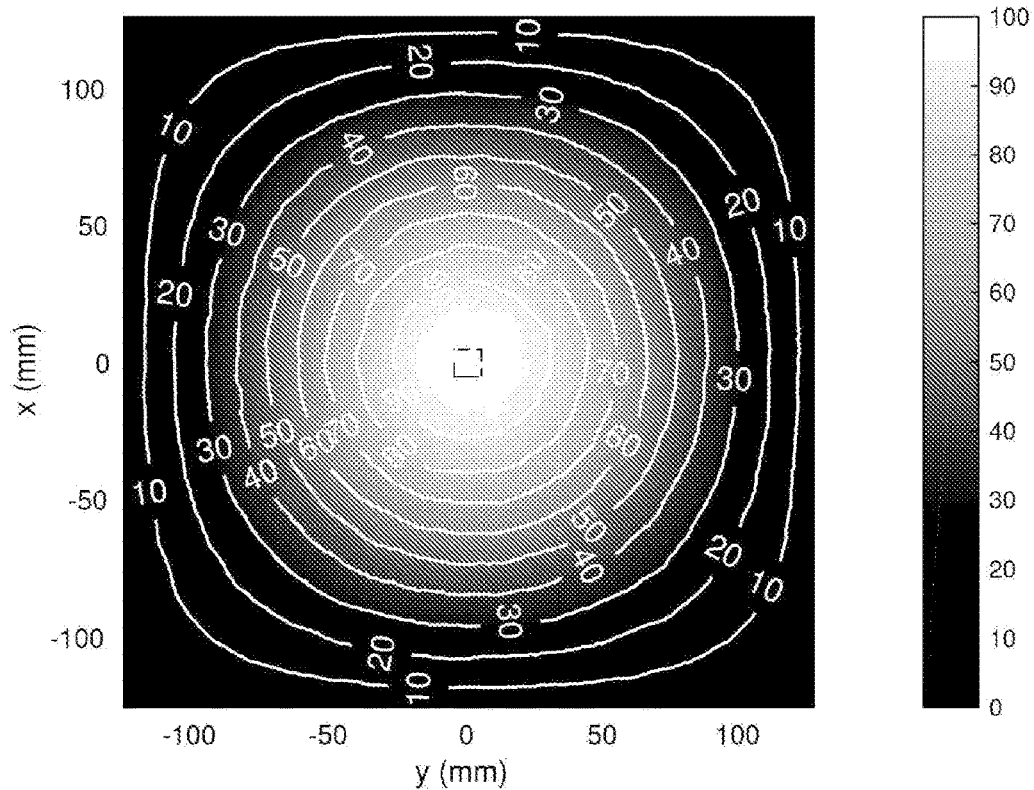
Figure 6C:
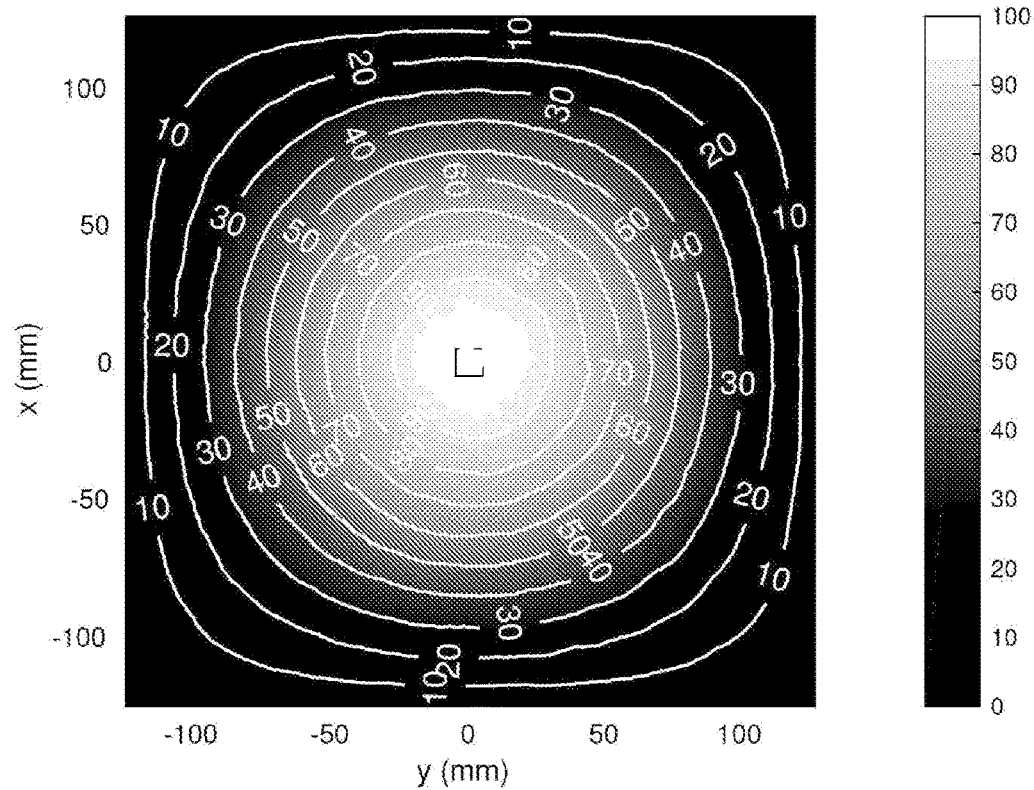
Figure 6D:
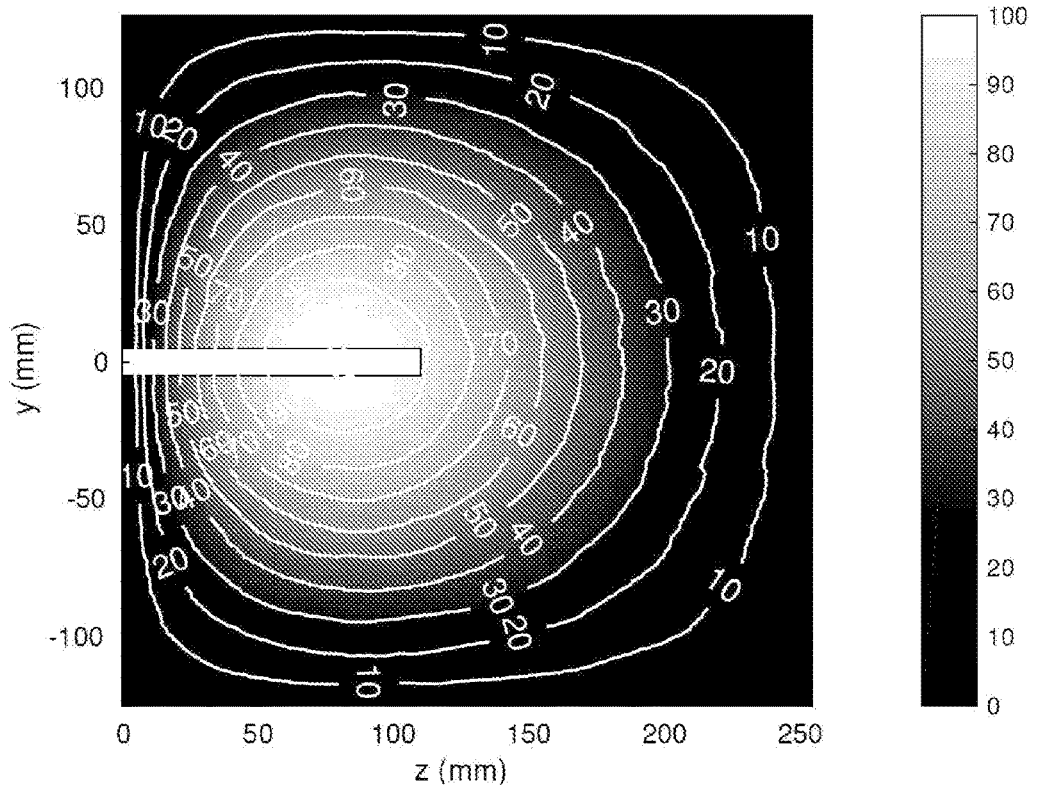
Figure 6E:
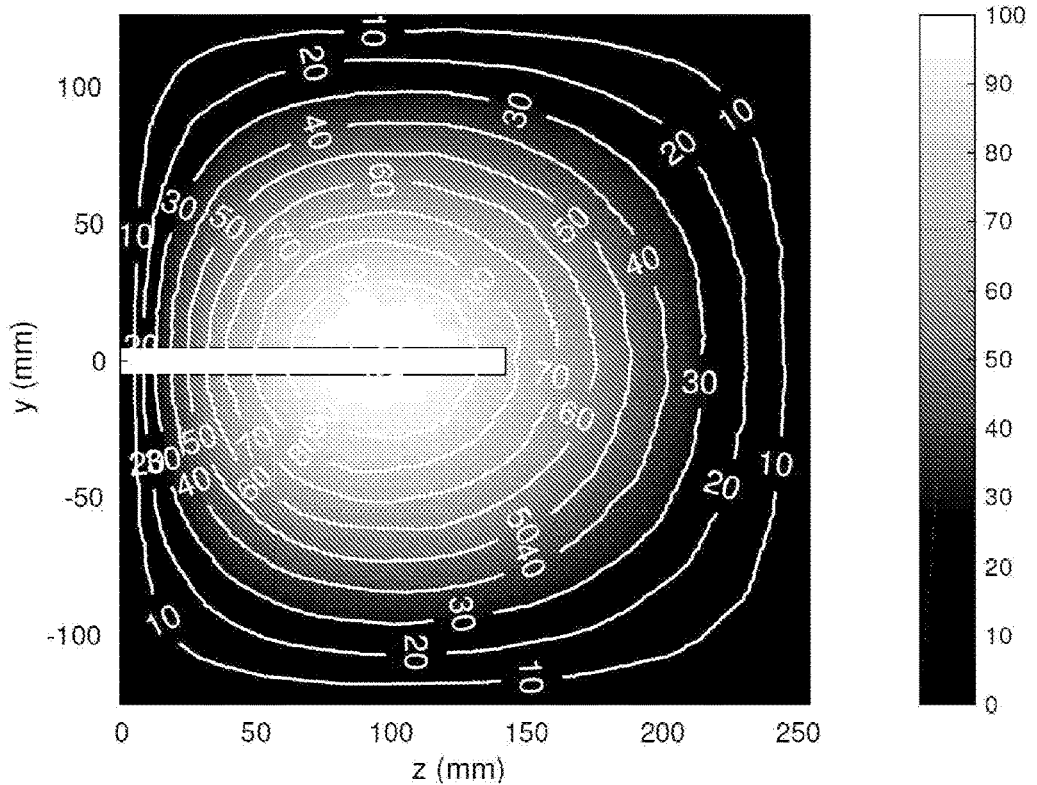
Figure 6F:
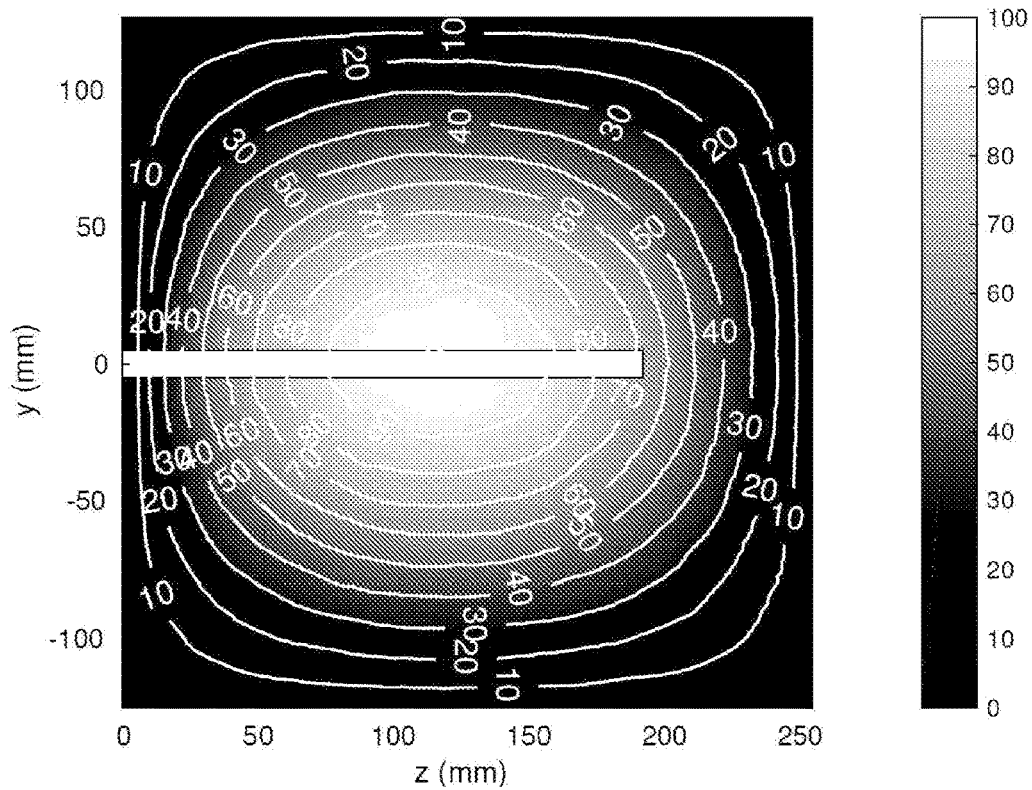

FIGS. 5A to 5C show the three-dimensional distribution of thermal neutrons within PMMA phantom 84 produced by monoenergetic proton beams with respective energies of 132 MeV/u (that is, MeV per nucleon), 153 MeV/u and 182 MeV/u, normalised per primary particle. In FIGS. 5A to 5C the incident beam is shown as a white cylindrical region, terminating at the Bragg peak. (Note: the beam profile is actually a Gaussian with 5 mm FWHM.)

FIGS. 6A to 6F show corresponding two-dimensional fluence contour maps estimated over slices parallel to the XY and XZ planes, intersecting with the incident beam and the point of maximum fluence.

FIGS. 7A to 7C show equivalent three-dimensional thermal neutron distributions within PMMA phantom 84 for carbon with monoenergetic beam energies of 250 MeV/u, 290 MeV/u and 350 MeV/u, normalised per primary particle. The incident beam is again shown as a white cylindrical region, terminating at the Bragg peak. (Note: the beam profile is actually a Gaussian with 5 mm FWHM.) FIGS. 8A to 8F show corresponding two-dimensional fluence maps, again shown on the XY and XZ planes, intersecting with the incident beam and the point of maximum fluence.

FIGS. 9A to 9F show simulated thermal neutron fluence plotted as a function of depth in a skull phantom for monoenergetic proton, $^{12}$C and $^{16}$O beams at each of the four beam energies used with each ion species.

The skull phantom was simulated as comprising 250× 250×10 mm³ of bone and 250×250×240 mm³ of muscle. Material compositions were based on tissue models taken from the National Institute of Standards and Technology (NIST) database.

As in FIGS. 4A to 4F, in FIGS. 9A to 9F, fluence is expressed in units of neutrons per square centimetre per primary particle and per gray of ion dose. Flux is averaged over square 5 mm×5 mm and 50×50 mm² regions normal to the beam and centred on the beam axis; results averaged over the full 50 mm×50 mm planes and over the central 5 mm×5 mm region of each plane only are indicated with solid lines and dashed lines, respectively. For clarity, 95% confidence intervals (±2σ) are shown only every 20 mm; inter-run fluence variations at any given depth are distributed approximately normally. The location of each Bragg peak is displayed as a solid vertical marker attached to the horizontal axis, with its width matching that of the corresponding fluence-depth curve.

B. Quantification of Neutron Capture Dose Enhancement

The estimated thermal neutron fluence values per gray were used to evaluate the additional biological effective dose deposited in the test target volumes resulting from boron neutron capture. The physical dose required to achieve a photon-equivalent dose of 100 Gy-Eq for is 90.91 Gy for protons and 40 Gy for both carbon and oxygen. The conversion factor $C_a=6.933\times10^{-14}$, together with the tumour boron concentrations listed in Table III, are combined with the specified physical dose and the estimated thermal neutron fluence per gray to produce an estimate for the dose boost; values are listed for all ion species and evaluated boron concentrations in Table VIII (below).

III. Discussion

For each of the simulated energies of all three ion species, the estimated thermal neutron fluence varies by less than 11% from the centre to the corner of the transaxial planes through both the Bragg peak (Table IV) and the point of maximum neutron fluence (Table V), within the two 50 mm×50 mm×50 mm target volumes defined inside the PMMA phantom.

TABLE IV

Neutron fluence (neutrons/cm²/primary) at periphery and centre of 50 mm square transaxial planes through Bragg peak in a 250 mm cubic PMMA phantom

| Primary | Energy (MeV) | $d_{BP}$ (mm) | Flux, corner | SD | Flux, central | SD | Corner/ central |
|---|---|---|---|---|---|---|---|
| proton | 73 | 36 | $2.34 \times 10^{-5}$ | $7.99 \times 10^{-7}$ | $2.72 \times 10^{-5}$ | $8.48 \times 10^{-7}$ | 85.7% |
|  | 132 | 106 | $9.18 \times 10^{-5}$ | $1.65 \times 10^{-6}$ | $1.02 \times 10^{-4}$ | $1.65 \times 10^{-6}$ | 89.8% |
|  | 153 | 141 | $1.05 \times 10^{-4}$ | $1.41 \times 10^{-6}$ | $1.16 \times 10^{-4}$ | $2.18 \times 10^{-6}$ | 91.0% |
|  | 182 | 188 | $1.03 \times 10^{-4}$ | $1.61 \times 10^{-6}$ | $1.14 \times 10^{-4}$ | $1.37 \times 10^{-6}$ | 90.4% |
| $^{12}$C | 150 | 44 | $4.90 \times 10^{-4}$ | $1.62 \times 10^{-5}$ | $5.56 \times 10^{-4}$ | $2.31 \times 10^{-5}$ | 88.1% |
|  | 250 | 108 | $1.41 \times 10^{-3}$ | $2.01 \times 10^{-5}$ | $1.56 \times 10^{-3}$ | $2.66 \times 10^{-5}$ | 90.6% |
|  | 290 | 140 | $1.62 \times 10^{-3}$ | $1.79 \times 10^{-5}$ | $1.78 \times 10^{-3}$ | $2.26 \times 10^{-5}$ | 91.0% |
|  | 350 | 190 | $1.54 \times 10^{-3}$ | $1.77 \times 10^{-5}$ | $1.69 \times 10^{-3}$ | $2.51 \times 10^{-5}$ | 90.9% |
| $^{16}$O | 177 | 44 | $6.17 \times 10^{-4}$ | $1.05 \times 10^{-5}$ | $6.91 \times 10^{-4}$ | $1.12 \times 10^{-5}$ | 89.3% |
|  | 297 | 108 | $1.82 \times 10^{-3}$ | $2.58 \times 10^{-5}$ | $2.00 \times 10^{-3}$ | $2.62 \times 10^{-5}$ | 91.0% |
|  | 345 | 138 | $2.11 \times 10^{-3}$ | $2.74 \times 10^{-5}$ | $2.32 \times 10^{-3}$ | $2.08 \times 10^{-5}$ | 91.3% |
|  | 418 | 190 | $2.01 \times 10^{-3}$ | $2.27 \times 10^{-5}$ | $2.19 \times 10^{-3}$ | $2.85 \times 10^{-5}$ | 91.5% |

TABLE V

Neutron fluence (neutrons/cm²/primary) at periphery and centre of 50 mm square transaxial planes through plane of maximum peak neutron fluence in a 250 mm cubic PMMA phantom

| Primary | Energy (MeV) | $d_{MF}$ (mm) | Flux, corner | SD | Flux, central | SD | Corner/central |
|---|---|---|---|---|---|---|---|
| proton | 73 | 54 | $2.62 \times 10^{-5}$ | $1.16 \times 10^{-6}$ | $2.93 \times 10^{-5}$ | $9.63 \times 10^{-7}$ | 89.3% |
|  | 132 | 82 | $9.99 \times 10^{-5}$ | $1.44 \times 10^{-6}$ | $1.12 \times 10^{-4}$ | $1.56 \times 10^{-6}$ | 89.0% |
|  | 153 | 92 | $1.25 \times 10^{-4}$ | $2.02 \times 10^{-6}$ | $1.40 \times 10^{-4}$ | $1.81 \times 10^{-6}$ | 89.4% |
|  | 182 | 112 | $1.51 \times 10^{-4}$ | $2.16 \times 10^{-6}$ | $1.68 \times 10^{-4}$ | $2.09 \times 10^{-6}$ | 89.6% |
| $^{12}$C | 150 | 66 | $5.54 \times 10^{-4}$ | $1.08 \times 10^{-5}$ | $6.17 \times 10^{-4}$ | $1.30 \times 10^{-5}$ | 89.7% |
|  | 250 | 98 | $1.42 \times 10^{-3}$ | $2.37 \times 10^{-5}$ | $1.57 \times 10^{-3}$ | $2.48 \times 10^{-5}$ | 90.4% |
|  | 290 | 98 | $1.42 \times 10^{-3}$ | $2.37 \times 10^{-5}$ | $1.57 \times 10^{-3}$ | $2.48 \times 10^{-5}$ | 90.4% |
|  | 350 | 132 | $1.93 \times 10^{-3}$ | $1.80 \times 10^{-5}$ | $2.13 \times 10^{-3}$ | $2.95 \times 10^{-5}$ | 90.8% |
| $^{16}$O | 177 | 82 | $7.14 \times 10^{-4}$ | $1.77 \times 10^{-5}$ | $7.89 \times 10^{-4}$ | $1.45 \times 10^{-5}$ | 90.5% |
|  | 297 | 96 | $1.81 \times 10^{-3}$ | $2.09 \times 10^{-5}$ | $2.00 \times 10^{-3}$ | $1.84 \times 10^{-5}$ | 90.5% |
|  | 345 | 120 | $2.16 \times 10^{-3}$ | $2.27 \times 10^{-5}$ | $2.37 \times 10^{-3}$ | $2.33 \times 10^{-5}$ | 90.9% |
|  | 418 | 134 | $2.48 \times 10^{-3}$ | $2.43 \times 10^{-5}$ | $2.72 \times 10^{-3}$ | $2.79 \times 10^{-5}$ | 91.2% |

Likewise, each of the simulated energies of all three ion species, the estimated thermal neutron fluence again varies by less than 11% from the centre to the corner of the transaxial planes through both the Bragg peak (Table VI) and the point of maximum neutron fluence (Table VII), within the two 50 mm×50 mm×50 mm target volumes defined inside the skull phantom.

TABLE VI

Neutron fluence (neutrons/cm²/primary) at periphery and centre of 50 mm square transaxial planes through Bragg peak in a 250 mm cubic skull phantom

| Primary | Energy (MeV) | $d_{BP}$ (mm) | Flux, corner | SD | Flux, central | SD | Corner/central |
|---|---|---|---|---|---|---|---|
| proton | 73 | 34 | $2.20 \times 10^{-5}$ | $7.40 \times 10^{-7}$ | $2.52 \times 10^{-5}$ | $1.12 \times 10^{-6}$ | 87.3% |
|  | 132 | 114 | $7.00 \times 10^{-5}$ | $1.12 \times 10^{-6}$ | $7.71 \times 10^{-5}$ | $1.66 \times 10^{-6}$ | 90.8% |
|  | 153 | 150 | $7.49 \times 10^{-5}$ | $1.24 \times 10^{-6}$ | $8.41 \times 10^{-5}$ | $1.37 \times 10^{-6}$ | 89.1% |
|  | 182 | 206 | $6.57 \times 10^{-5}$ | $1.15 \times 10^{-6}$ | $7.28 \times 10^{-5}$ | $1.63 \times 10^{-6}$ | 90.2% |
| $^{12}$C | 150 | 42 | $4.20 \times 10^{-4}$ | $1.04 \times 10^{-5}$ | $4.73 \times 10^{-4}$ | $1.21 \times 10^{-5}$ | 88.8% |
|  | 250 | 112 | $1.10 \times 10^{-3}$ | $1.44 \times 10^{-5}$ | $1.21 \times 10^{-3}$ | $1.65 \times 10^{-5}$ | 90.8% |
|  | 290 | 146 | $1.23 \times 10^{-3}$ | $2.32 \times 10^{-5}$ | $1.35 \times 10^{-3}$ | $2.19 \times 10^{-5}$ | 91.1% |
|  | 350 | 204 | $1.03 \times 10^{-3}$ | $1.70 \times 10^{-5}$ | $1.13 \times 10^{-3}$ | $2.00 \times 10^{-5}$ | 90.8% |
| $^{16}$O | 177 | 42 | $5.40 \times 10^{-4}$ | $1.22 \times 10^{-5}$ | $6.06 \times 10^{-4}$ | $1.45 \times 10^{-5}$ | 89.1% |
|  | 297 | 112 | $1.42 \times 10^{-3}$ | $2.16 \times 10^{-5}$ | $1.57 \times 10^{-3}$ | $1.72 \times 10^{-5}$ | 90.6% |
|  | 345 | 146 | $1.58 \times 10^{-3}$ | $1.97 \times 10^{-5}$ | $1.75 \times 10^{-3}$ | $2.07 \times 10^{-5}$ | 90.8% |
|  | 418 | 202 | $1.36 \times 10^{-3}$ | $1.65 \times 10^{-5}$ | $1.50 \times 10^{-3}$ | $1.76 \times 10^{-5}$ | 90.5% |

TABLE VII

Neutron fluence (neutrons/cm²/primary) at periphery and centre of 50 mm square transaxial planes through plane of maximum peak neutron fluence in a 250 mm cubic skull phantom

| Primary | Energy (MeV) | $d_{MF}$ (mm) | Flux, corner | SD | Flux, central | SD | Corner/central |
|---|---|---|---|---|---|---|---|
| proton | 73 | 48 | $2.32 \times 10^{-5}$ | $6.67 \times 10^{-7}$ | $2.63 \times 10^{-5}$ | $6.32 \times 10^{-7}$ | 88.2% |
|  | 132 | 72 | $8.00 \times 10^{-5}$ | $1.25 \times 10^{-6}$ | $9.00 \times 10^{-5}$ | $1.64 \times 10^{-6}$ | 88.9% |
|  | 153 | 86 | $9.87 \times 10^{-5}$ | $1.87 \times 10^{-6}$ | $1.10 \times 10^{-4}$ | $1.14 \times 10^{-6}$ | 89.5% |
|  | 182 | 116 | $1.16 \times 10^{-4}$ | $1.78 \times 10^{-6}$ | $1.29 \times 10^{-4}$ | $1.50 \times 10^{-6}$ | 90.2% |
| $^{12}$C | 150 | 62 | $4.63 \times 10^{-4}$ | $1.16 \times 10^{-5}$ | $5.16 \times 10^{-4}$ | $1.06 \times 10^{-5}$ | 89.7% |
|  | 250 | 94 | $1.11 \times 10^{-3}$ | $1.45 \times 10^{-5}$ | $1.24 \times 10^{-3}$ | $1.77 \times 10^{-5}$ | 89.8% |
|  | 290 | 104 | $1.30 \times 10^{-3}$ | $1.77 \times 10^{-5}$ | $1.45 \times 10^{-3}$ | $2.08 \times 10^{-5}$ | 90.0% |
|  | 350 | 126 | $1.48 \times 10^{-3}$ | $2.23 \times 10^{-5}$ | $1.63 \times 10^{-3}$ | $2.09 \times 10^{-5}$ | 90.3% |
| $^{16}$O | 177 | 76 | $6.00 \times 10^{-4}$ | $9.72 \times 10^{-6}$ | $6.65 \times 10^{-4}$ | $1.29 \times 10^{-5}$ | 90.3% |
|  | 297 | 96 | $1.43 \times 10^{-3}$ | $2.01 \times 10^{-5}$ | $1.58 \times 10^{-3}$ | $2.34 \times 10^{-5}$ | 90.8% |
|  | 345 | 116 | $1.67 \times 10^{-3}$ | $2.15 \times 10^{-5}$ | $1.85 \times 10^{-3}$ | $1.87 \times 10^{-5}$ | 90.4% |
|  | 418 | 136 | $1.87 \times 10^{-3}$ | $1.98 \times 10^{-5}$ | $2.06 \times 10^{-3}$ | $2.82 \times 10^{-5}$ | 90.8% |

The gradient of the thermal neutron fluence with respect to depth along the beam axis is dependent on the beam energy, and increases in the vicinity of the Bragg peak as the energy of the primary particle increases. Moreover, the distance between the plane of maximum thermal neutron fluence and the Bragg peak increases with the increase in the energy of the primary particle. Therefore, for a typical treatment plan, which would comprise a range of beam energies (and hence depths in Z) and horizontal and vertical steps (in the XY plane), the total thermal neutron fluence will integrate to produce a virtually uniform neutron field in the treatment volume.

The neutron fluence per unit of absorbed physical dose is such that delivery of a typical treatment plan will enable a total biological effective dose enhancement of the order of 20-40% for proton beams and 6-12% for carbon and oxygen ion beams within the target volume, for tissue boron concentrations previously reported in the literature.

TABLE VIII

Estimated percentage biological dose increase (Gy-Eq) for two target volumes obtained with four concentrations of $^{10}$B-bearing BPA

| Ion | $^{10}$B conc. (PPM) | % Increase at Treatment Volume Depth | |
|---|---|---|---|
| | | 100-150 mm | 140-190 mm |
| P | 30 | 5.22 | 7.32 |
| | 67 | 11.65 | 16.36 |
| | 123 | 21.39 | 30.02 |
| | 174 | 30.25 | 42.48 |
| $^{12}$C | 30 | 1.49 | 2.03 |
| | 67 | 3.32 | 4.54 |
| | 123 | 6.10 | 8.33 |
| | 174 | 8.62 | 11.79 |
| $^{16}$O | 30 | 1.20 | 1.67 |
| | 67 | 2.69 | 3.74 |
| | 123 | 4.93 | 6.87 |
| | 174 | 6.98 | 9.72 |

For each of the reported boron concentrations, the tumour to normal tissue ratio can be used to estimate the additional dose in the adjacent normal tissue, assuming a CBE factor of 1.3 for normal brain tissue [33, 34]. For the highest concentration of boron (174 ppm) and lowest tumour: healthy-tissue boron concentration ratio, a proton-beam dose of 100 Gy-Eq delivered to the treatment volume will induce a maximum additional dose of 4.8 Gy-Eq to surrounding tissue due to the presence of boron (for a dose boost to the treatment volume of 42.48 Gy-Eq). The corresponding values for $^{12}$C and $^{16}$O are 1.3 Gy-Eq and 1.1 Gy-Eq for dose boosts of 11.79 Gy-Eq and 9.72 Gy-Eq, respectively. For comparison, a BNCT treatment plan for glioblastoma multiforme typically delivers a peak dose of 8-14 Gy-Eq to normal brain tissue over 2-3 fractions [33].

Recent literature recommends delivery of heavy ion radiotherapy via hypofractionation (1-2 fractions only) [6, 35-37]. From a practical perspective, this makes addition of a boron-bearing drug infusion step to the treatment process a minimal additional burden on the patient, as it may only need to be performed once or twice.

It has recently been observed that the main impediment to widespread adoption of boron neutron capture therapy is the availability of suitable epithermal neutron sources rather than the availability of appropriate pharmaceutical agents for boron delivery, as was previously the case [38]. Embodiments of the present invention have the potential to offer a new source of thermal neutrons at any proton or heavy ion treatment facility, conveniently situated at the point of treatment inside the patient's own body. With the prospect of further progress in the development of new boron and gadoliniumbearing drugs and delivery methods, with greater tumour specificity and potentially achievable tissue concentrations, it is envisaged that it will become possible to achieve even greater dose enhancement in the future.

Example 2

In a further example, a similar set of simulations was conducted. Significance was arbitrarily defined as an average 10% increase in photon-equivalent dose within a tumour resulting from the administration of a non-toxic bolus of neutron-capture agent (though it is envisaged that the method of this embodiment can be used with any desired dose increase factor). To do so, the concentration of neutron capture agent required to provide a 10% increase in effective photon-equivalent dose is determined for a simple simulated therapeutic proton/heavy ion treatment plan, and this is compared with concentrations reported in the literature.

The first step is to evaluate the neutron fluence resulting from pencil-beam irradiation of a point within a target volume. A set of simulations of such a pencil beam, for both proton and $^{12}$C beams, was conducted with four different energies in a homogeneous PMMA target. Dose and neutron fluence distributions were recorded for each simulation; corresponding distributions at energies in between these were also estimated by interpolating between the distributions obtained at these energies. A simple treatment plan was then implemented, in which the pencil beam was stepped across an array of points inside a treatment volume at a series different energies. The primary particle fluence at each energy was then weighted such that an approximately flat biological effective dose (BED) was delivered to a defined treatment volume by the ion beam; two 50 mm cubic volumes were evaluated, one centred at a depth of 125 mm and a second centred at a depth of 165 mm. Neutron fluence distributions were then estimated based on the primary particle fluence weights and summed across the entire treatment volume in each case. Based on the neutron fluence estimates obtained through this process, the additional neutron-capture dose per unit of primary proton/heavy ion dose, per unit of $^{10}$B-BPA concentration was estimated such that the concentration required for a 10% increase in dose could be determined.

A. Pencil Beam Simulations

FIG. 10 is a view of the simulation configuration used for pencil beam thermal neutron fluence estimation in this example. The same number of incident protons and $^{12}$C ions was again employed, while the hadronic physics models used in the simulations are again listed in Table I and the full set of beam energies for the protons and $^{12}$C ions and the corresponding locations of Bragg peaks in each phantom are listed in Table II.

Pencil beam physical dose and neutron fluence distributions were obtained for each beam type and energy (see Table II), and normalised per primary particle. To estimate dose and neutron fluence distributions for beam energies which were not simulated (due to the substantial computational cost of performing simulations for all intermediate energies), an interpolation procedure was performed. Firstly, the expected location of the Bragg peak for each intermediate energy was estimated via a 2nd-order polynomial interpolation between the locations measured from the dose distributions obtained at each of the four simulated energies. Next, the dose and neutron fluence distributions from all but the highest-energy simulation were translated such that their Bragg peaks aligned with that of the highest energy simulation, and a 3D spatial interpolation of the dose and neutron fluence distributions for the intermediate energies was performed. Finally, the interpolated 3D dose and neutron fluence distributions were translated back to the previously-estimated location of the Bragg peak for each energy. The result was a library of estimated physical dose distributions and thermal neutron fluence distributions per primary particle for proton and $^{12}$C beams, for energies in steps of 1 MeV/u in the range 73-182 MeV/u for protons and 150-350 MeV/u for $^{12}$C. While the method is only an approximation, its accuracy can be improved if desired by performing simulations at additional energies in the range of interest.

The library of physical doses distributions deposited by the pencil beams were then converted to biological dose; for protons, the relative biological effectiveness factor was assumed to be 1.1, while for $^{12}$C it was assumed to be 3.0 at the Bragg peak, 1.5 in the entrance plateau and buildup region (defined as the region with a deposited dose less than 60% of the maximum value), and a linear interpolation between these values in the intermediate region. The biological dose distributions were then used to develop a simple treatment plan for two target volumes for each beam type. These three-dimensional dose distributions for the centred pencil beam at the kth energy (k ∈[1 . . . K]) are denoted $BED_{ctr,k}$. The corresponding neutron flux is denoted $\phi_{ctr,k}$.

B. Estimated Neutron Capture Dose Enhancement

As this example is concerned with determining the feasibility of this embodiment, rather than with evaluating a specific treatment plan, a set of simple, generic treatment plans were developed for the PMMA target in order to estimate the order of neutron capture agent concentration that would be required to achieve a 10% increase in photon-equivalent biological dose. For each energy, the BED and neutron fluence maps (calculated via the interpolation method previously introduced) are stepped across the transverse (xy) plane of the treatment volume corresponding to the Bragg peak depth at each energy, to a total of R×C positions for each of the k energies:

$$BED_k = \frac{1}{RC}\sum_{r=1}^{R}\sum_{c=1}^{C}\{BED_{ctr,k}(r,c)\}$$

$$\phi_k = \frac{1}{RC}\sum_{r=1}^{R}\sum_{c=1}^{C}\{\phi_{ctr,k}(r,c)\}$$

where $BED_{ctr,k}(r, c)$ is $BED_{ctr,k}$ laterally translated so that the centre of the Bragg peak is located at row and column (r, c) in the plane, and $\phi_k(r, c)$ is the corresponding neutron fluence. If the desired photon-equivalent dose is D, then the objective is to achieve the most uniform approximation of this dose possible within the treatment volume by determining the number of primary particles $N_k$ required at each energy $k$ which best approximate a flat dose. This is obtained by solving $$\operatorname*{argmin}_{N_k}\left\|\left(\sum_{k=1}^{K}N_k BED_k\right) - D\right\|^2$$

using an optimisation technique such as Levenberg-Marquardt optimisation, subject to the constraint that $N_k$ must be positive. The total number of primary particles required at each energy can then be multiplied by the corresponding map of neutron production per primary particle for each energy, to yield a map of total neutron fluence f throughout the phantom (both inside and outside of the treatment volume):

$$\phi = \sum_{k=1}^{K} N_k \phi_k.$$

The biological dose enhancement resulting from the presence of the neutron capture agent, normally referred to as the boron dose in BNCT literature, is estimated using the following relation:

$$D_B = \phi \sigma_{NCA} N_{NCA} \times CBE$$

where $\sigma_{NCA}$ is the fluence-to-kerma conversion factor (approximately $8:66\times10^{-14}$ for $^{10}$B and $9:27\times10^{-15}$ for $^{157}$Gd), NNCA is the concentration of neutron capture agent in parts per million, and the compound biological effectiveness CBE=3.8 for $^{10}$B-BPA and ≈40 for the DOTA 157-Gadolinium triphenylphosphonium salt complex (based on results of studies in the field of photon activated therapy using the same agent, and correcting for expected Auger electron production).

For this example, the target dose was set to D=1 GyE, R=C=11, and steps between rows and columns were set to 5 mm (i.e. the same as the FWHM of the beam) for a 50 mm square treatment plane at each energy. A range of energies were selected to extend the spread out Bragg peak (SOBP) between depths of 100 mm to 150 mm for the first treatment volume and 140 mm to 190 mm for the second; energies were incremented in steps of 1 MeV/u. Therefore, each treatment volume is a 50 mm cubic volume, with 1 GyE of dose delivered by the ion beam.

C. Reported Neutron Capture Agent Concentrations

A selection of reported clinical and/or preclinical tissue concentrations of boron and gadolinium, together with the ratio of concentration in tumours to healthy tissue, are listed in Tables III and IX, respectively.

TABLE IX

Gadolinium-based neutron capture agent concentrations reported in the literature. Tumour:normal tissue concentration ratios of at least 70 are commonly reported in the literature

| Reported by | Compound | Target | Concentration (ppM) |
|---|---|---|---|
| De Stasio et al., 2001 [40] | Gd-DOTA | GBM (in vitro) | 140 (1 h) |
| Le et al., 2006 [41] | Gd-DTPA encapsulated liposome | TC-1 (mouse lung endothelium, in vivo) | 159 |

TABLE IX-continued

Gadolinium-based neutron capture agent concentrations reported in the literature. Tumour:normal tissue concentration ratios of at least 70 are commonly reported in the literature

| Reported by | Compound | Target | Concentration (ppM) |
|---|---|---|---|
| Peters et al., 2015 [42] | Gd-DOTAP liposome | F98 & LN229 (glioma, in vitro) | 768 |
| Ichikawa et al., 2014 [43] | Gd-DTPA; Chitosan nanoparticles | B16F10 (mouse melanoma, in vivo) | 1500 |
| Tokumitsu et al., 2000 [44] | Gd-DTPA; Chitosan nanoparticles | B16F10 (mouse melanoma, in vivo) | 1800 |
| Morrison et al., 2014 [45] | $Gd^{III}$-triarylphosphonium salts | T98G (glioblastoma, in vitro) | 3000 |

D. Results

Treatment Plans and Neutron Fluence Distributions

Treatment plans were prepared for each target volume for both proton and carbon ion beams. The total number of primary particles at each energy required for achieving an average biological dose of 1 GyE across the target volumes were computed, and the 3D dose distributions calculated. The case of carbon-ion irradiation of the shallower treatment volume (at depths ranging from 100 mm to 150 mm) is shown in FIGS. 11A to 11D.

The per-primary-particle neutron distributions corresponding to each of the energies in the treatment plan were scaled by the number of primary particles determined for each plan and summed for all energies. An example of the resulting distribution of neutron fluence (shown as a percentage of the maximum value) is shown in FIGS. 12A to 12F.

The maximum, mean and minimum neutron fluences obtained within the treatment volumes are listed in Table X.

TABLE X

Neutron fluences obtained for each target volume and treatment plan, assuming a target volume average proton or heavy ion biological dose of 1 GyE

| Target Depth (mm) | Primary Ion | Neutron fluence per GyE primary dose (n/cm²/GyE) | | |
|---|---|---|---|---|
| | | Minimum | Mean | Maximum |
| 100-150 | Proton | $5.96 \times 10^8$ | $7.79 \times 10^8$ | $9.06 \times 10^8$ |
| | $^{12}C$ | $2.86 \times 10^8$ | $3.34 \times 10^8$ | $3.60 \times 10^8$ |
| 140-190 | Proton | $6.26 \times 10^8$ | $8.82 \times 10^8$ | $1.09 \times 10^9$ |
| | $^{12}C$ | $3.17 \times 10^8$ | $4.08 \times 10^8$ | $4.68 \times 10^8$ |

TABLE XI $^{10}$B-based neutron capture agent concentrations required to obtain a 10% increase in biological effective dose

| Target Depth (mm) | Primary | $^{10}$B neutron capture agent concentration (ppm) | | | |
|---|---|---|---|---|---|
| | | BPA (brain) [46] RBE = 3.8 | BSH (brain) [47] RBE = 1.2 | BPA (liver) [26] RBE = 9.94 | BSH (liver) [26] RBE = 4.22 |
| 100-150 | Proton | 390 | 1240 | 149 | 351 |
| | $^{12}C$ | 910 | 2880 | 348 | 820 |
| 140-190 | Proton | 345 | 1090 | 132 | 310 |
| | $^{12}C$ | 744 | 2360 | 285 | 670 |

TABLE XII $^{157}$Gd concentrations required to obtain a 10% increase in biological effective dose, with estimated values based on published RBEs for non-specific multiple-Auger-electron-emitting nuclei; the right-most columns are based on Monte Carlo simulation results

| Target Depth (mm) | Primary | $^{157}$Gd neutron capture agent concentration (ppm) | | | | |
|---|---|---|---|---|---|---|
| | | Cell [48] RBE = 5 | DNA [48] RBE = 20 | DNA [49] RBE = 10 | MC:DNA [50] RBE = 12.5 | MC:Cell [50] RBE = 1.5 |
| 100-150 | Proton | 2790 | 697 | 1400 | 1110 | 9300 |
| | $^{12}C$ | 6510 | 1630 | 3260 | 2580 | 21700 |
| 140-190 | Proton | 2460 | 616 | 1230 | 978 | 8220 |
| | $^{12}C$ | 5330 | 1330 | 2660 | 2110 | 17800 |

It will be noted that the results of Tables XI and XII are superior to and supersede those of Example 1 (cf. Table VIII). The ad hoc treatment plan implemented in Example 2 properly accounts for the entrance dose in calculating the weight factors of each discrete beam energy. Therefore, the subsequent estimation of the neutron fluence as a result of fragmentation and internal generation of thermal neutrons is a more accurate representation of that which would be seen in a clinical treatment plan, compared to Example 1.

Required NCA Concentrations

The tumour concentrations of $^{10}$B and $^{157}$Gd required to achieve a 10% increase in biological effective dose are listed in Table XI and XII, respectively. The CBEs for each agent are based on values estimated in each listed supporting publication. Based on these estimated tumour concentrations, reported tumour:normal tissue concentration ratios and normal-tissue CBEs, the maximum percentage increases in normal-tissue biological effective dose are listed in Table XIII.

TABLE XIII

Maximum percentage increase in biological dose delivered to normal tissue, for a 10% increase in biological effective dose in the tumour
Maximum increase in normal tissue biological dose (%)

| BPA (brain) [46] | BSH (brain) [47] | BPA (liver) [26] | BSH (liver) [26] | $^{157}$Gd (all) |
|---|---|---|---|---|
| 0.68 | 2.60 | 1.50 | 7.40 | 0.14 |

Tumour:healthy $^{10}$B concentration ratio for BPA and BPA in the brain are based on values reported by Barth et al. [14] and Koganei et al., respectively [32]; for BSH, the values are as reported by Suzuki et al. [26]. Tumour:healthy $^{157}$Gd concentration ratio is assumed to be 70:1, although even higher ratios are reported in the literature. As the normal-tissue CBE is not yet well known for $^{157}$Gd-based agents, it is assumed here to have the same value as for the tumour (a worst-case assumption).

E. Discussion

Several conclusions may be drawn by examining the tumour concentrations of each NCA listed in Tables XI and XII. Firstly, the NCA concentrations required to achieve a 10% increase in biological effective dose in the liver are substantially lower than those required in the brain for both BPA and BSH, with BPA looking particularly promising due to the combination of high CBE and good tumour/normal tissue contrast reported by Suzuki et al. [26]. On the other hand, BSH concentrations have been reported in the literature which would realise a dose boost of close to 10%—for example, Suzuki et al. [39] reported up to 200 and 234 ppm for BSH plus two different embolising agents, which would offer dose boosts of the order of 6.4-7.5% in the liver.

The situation is somewhat less positive for the brain; $^{10}$B-BPA concentrations required to achieve a 10% increase in biological effective dose during proton therapy in the brain would need to be around three times greater than the highest concentrations reported in the literature to date, while the concentration needed for carbon ion therapy is even greater.

Conversely, with the highest BPA concentration reported in the literature of 125 ppm, the increase in dose is approximately 3.2-3.6% for proton therapy, and about half that for carbon. These results do not rule out the use of boron neutron capture agents for treatment in the brain according to this embodiment, but demonstrate the need for further development of boron-based NCAs.

Tantalisingly, there are reports in the literature of strong uptake of BPA in the pancreas, an organ in which cancer is notoriously difficult to treat. While there appears to be very little research into BNCT specifically applied to the pancreas (particularly on tumour to normal NCA concentration ratios and CBE), it would appear to be a good candidate for this embodiment.

Several promising new $^{10}$B-based NCAs are still in development [30]. BSH has been somewhat disappointing as an NCA in BNCT, chiefly due to its inability to directly penetrate the cell membrane. However, several BSH-derived compounds have been proposed that combine up to 8 instances of the BSH compound with peptide chains, which are able to penetrate the membrane and deliver high concentrations of boron within the cell. Boron concentrations in excess of 5000 ppm have been reported for these compounds [51]. Other promising recent studies have investigated the use of using boron nitride nanotubes as NCAs in BNCT, which can also potentially deliver very high $^{10}$B concentrations to the tumour [52].

For $^{157}$Gd, the situation is more complex. The values are highly dependent on how the $^{157}$Gd atoms are distributed; when they are either electrostatically attached to DNA or concentrated in the cell nucleus, the required concentrations are well within the ranges reported in the literature; this remains true even when the gadolinium is present in the cytoplasm or outside of the cell membrane. Several of the gadolinium compounds now in development appear to have many very promising properties for highly selective tumour uptake, and in particular high uptake in the nucleus and mitochondria, where they are most effective for neutron capture therapy. Significantly, many of the recently developed gadolinium-based compounds appear to offer very high tumour:normal tissue concentration ratios.

Comparing the required tumour concentrations obtained in this study to values previously published for both boron (up to 231 ppm in the liver [26]) and gadolinium (up to 3000 ppm in vitro [45]) indicates that for some agents and some target tissues, achieving at least a 10% increase in biologically effective dose (or, equivalently, reducing the external radiation dose and hence reducing normal tissue complication probability) should be feasible.

Additionally, there is also the possibility of further increasing the neutron yield of heavy ion therapy. Since the production of neutrons within the target volume is typically considered a nuisance rather than a central objective, there has been little research aimed at identifying particular primary species which will result in greater rates of thermal neutron production in human tissue targets. We hypothesise that relatively neutron-rich primary ion species such as deuterium or helium may increase the thermal neutron yield, and therefore providing a larger dose boost via thermal neutron capture than is possible with either protons or carbon ions. This is currently a subject of further investigation, with results to be reported in future work.

Regarding the additional dose introduced to healthy tissues resulting from implementation of this embodiment, Table XIII shows that for most proposed NCAs, the increased dose is quite small compared to the dose boost delivered to the tumour (the worst-case scenario being BSH in the liver, due to the relatively low tumour:normal tissue contrast ratio of 0.3). For a 70 GyE primary ion dose to the tumour (typically delivered over several fractions), if the BPA concentration is sufficient to provide an extra 7 Gy tumour dose via NCEPT, the maximum additional normal-tissue dose (at the margin of the treatment volume) would be 0.47 GyE in the brain and 1.1 GyE in the liver (with 1.8 GyE and 5.2 GyE obtained with BSH in the brain and liver, respectively). For comparison, a BNCT treatment plan for glioblastoma multiforme typically delivers a peak dose of 8-14 GyE to normal brain tissue over 2-3 fractions [33].

One possible limitation of this embodiment is the need to fractionate the delivery of the therapeutic dose, which would either necessitate the use of a NCA with a long residence time or require repeated infusion of the NCA. However, the most recent literature recommends delivery of heavy ion radiotherapy via hypofractionation (1-2 fractions only) [6, 35-37]. From a practical perspective, this makes addition of a boron-bearing drug infusion step to the treatment process a minimal additional burden on the patient, as it may only need to be performed once or twice.

As a final observation on the practicality of this embodiment: the main impediment to widespread adoption of neutron capture therapy is the limited availability of suitable epithermal neutron sources rather than the availability of appropriate NCAs [38]. This approach has the potential to offer a new source of thermal neutrons at any proton or heavy ion treatment facility, conveniently situated at the point of treatment inside the patient's own body. With the prospect of further progress in the development of new NCAs, with greater tumour specificity and potentially very high achievable tumour concentrations, and possibly in combination with ultrasonic or other uptake enhancement methods, it may be possible to achieve even greater dose enhancement in the future.

F. Conclusion

This example demonstrates that the thermal neutron fluence distribution resulting from proton and carbon ion therapy mostly originates in the vicinity of the Bragg peak (i.e. from a point internal to the treatment volume), with the neutron fluence falling with increased distance from the Bragg peak in all directions. The fluence distribution resulting from a realistic treatment plan is sufficient to enable a significant increase of the order of 10% with realistic NCA concentrations of the order of magnitude previously reported in the literature. The resulting dose increase in normal tissues is quite modest, and is believed unlikely to cause additional harm to the patient.

Example 3

The approach of the aforementioned embodiments was tested experimentally. A series of proof-of concept experiments were performed at Japan's HIMAC facility, to quantify the effective increase in biological dose which can be achieved in vitro. Cultured T98-G cancer cells adhered to the inner surface of T25 cell culture flasks were irradiated in carbon and helium ion beams, with and without the presence of realistic concentrations of neutron capture agents.

Three frozen vials of T98G (JCRB9041, human glioblastoma multiforme) cell lines were purchased from the National Institutes of Biomedical Innovation, Health and Nutrition, JCRB Cell Bank and used throughout the experiments.

Prior to the start of the experiments, the cells were revived and passaged twice prior to seeding 160 T25 flasks, with 5 mL of complete growth medium (DMEM+10% FBS). Flasks were incubated at 37±1° C. in an atmosphere of 5±1% $CO_2$.

The experiments utilised $^{12}C$ and $^{4}He$ beams with 60 mm Spread Out Bragg Peak (SOBP60) spectra, and an approximate dose rate of 1 Gy/min. Cell viability was measured as a function of ion beam dose in cultured T98-G human glioblastoma cells, with and without the presence of two neutron capture agents, $^{10}B$ enriched 4-borono-L-phenylalanine ($^{10}B$-BPA) and 2,2',2"-(10-(4-(((triphenylphosphonio)methyl)benzyl)-1,4,7,10-tetraazacyclododecane-1,4,7-triyl) triacetatogadolinium(III) trifluoroacetate (157Gd-DOTA-TPP salt complex).

A set of 300×300×10 mm³ PMMA slabs were used in conjunction with a PMMA receptacle for holding two flasks. With this arrangement, the flasks containing the cell cultures were positioned inside a cubic 300×300×300 mm³ PMMA phantom in a plane normal to the incident beam, at a depth corresponding to the midpoint of the SOBP60 as illustrated schematically in FIG. 13. The neutron fluence predicted via Monte Carlo simulation in Example 2 is overlayed on this figure for illustrative purposes. The ion beams were $^{12}C$ and $^{4}He$ beams with dimensions of 100×100 mm² (width×height) and SOBP60 energy spectra with mean energies of 290 MeV/u and 150 MeV/u, respectively (corresponding to SOBP depth ranges of approximately 8 to 14 cm in PMMA).

In Vitro Measurements.

The irradiation campaign was conducted on four consecutive nights (carbon ion beam irradiations were conducted on the first and third nights, while helium ion beam irradiations were performed on the second and fourth night) at the HIMAC biological beamline. Forty flasks were irradiated during each night, at 80% to 90% confluence (corresponding to ~3.75×10⁵ cells per flask). Twenty-four hours prior to each irradiation, 10 flasks were incubated with 500 μM of $^{10}B$-BPA, while a second set of 10 flasks were incubated with 500 μM of $^{157}Gd$-DOTA-TPP salt complex. The remaining 20 flasks were used as control.

On the night of irradiation, the beam was calibrated for dose rate and dose-depth deposition and the dose-rate at the centre of the Bragg peak (corresponding to the location of the cells) was measured with an ionisation chamber. Immediately prior to irradiation, flasks were filled with a complete DMEM media (~30 mL per flask). Flasks were irradiated in pairs, with flasks containing the neutron capture agents irradiated together, followed by corresponding control flasks (containing no neutron capture agent). Ten different dose values were used with each ion beam: 0, 0.9, 1.8, 2.3, 2.7, 3.2, 3.6, 4.1, 4.6, and 7.3 Gy for helium, and 0, 0.6, 1.3, 1.6, 1.9, 2.2, 2.5, 2.8, 3.1 and 5 Gy for carbon.

After irradiation, the medium was aseptically removed from the irradiated flasks. Cells were washed with 5 mL of DPBS which was removed and discarded. Cells were then trypsinised, detached from the flasks and resuspended in completed growth medium. Cell count and viability was recorded.

Sixteen 96-well plates were populated each night, each well containing approximately 375 cells, and each set of three wells corresponding to one flask. One set of eight 96-well plates contained a full set of irradiated cells incubated with the neutron capture compounds (as shown in Table XIV), while a second set of 8 well plates contained irradiated cells without any neutron capture agent (Table XV).

TABLE XIV

Well plate layout for flasks containing neutron capture agent. Wells labelled 'a' corresponds to cells incubated and irradiated in the presence of boron-based neutron capture agent, while those labelled 'b' denote the those similarly treated with the gadolinium-based agent.

|   | 1 | 2 | 3 | 4 | 5 | 6 | 7 | 8 | 9 | 10 | 11 | 12 |
|---|---|---|---|---|---|---|---|---|---|----|----|----|
| a | a1 | a1 | a1 | a9 | a9 | a9 | b7 | b7 | b7 |  |  |  |
| b | a2 | a2 | a2 | a10 | a10 | a10 | b8 | b8 | b8 |  |  |  |
| c | a3 | a3 | a3 | b1 | b1 | b1 | b9 | b9 | b9 |  |  |  |
| d | a4 | a4 | a4 | b2 | b2 | b2 | b10 | b10 | b10 |  |  |  |
| e | a5 | a5 | a5 | b3 | b3 | b3 | mem | mem | mem |  |  |  |
| f | a6 | a6 | a6 | b4 | b4 | b4 | bl | bl | bl |  |  |  |
| g | a7 | a7 | a7 | b5 | b5 | b5 | bl | bl | bl |  |  |  |
| h | a8 | a8 | a8 | b6 | b6 | b6 | bl | bl | bl |  |  |  |

TABLE XV

Well plate layout for control (untreated) flasks. Wells labelled 'c' corresponds to flasks irradiated in the same positions as the 'a' flasks in Table XIV; wells labelled 'd' similarly correspond to flasks irradiated in the same position as the 'b' flasks in Table XIV.

|   | 1  | 2  | 3  | 4   | 5   | 6   | 7   | 8   | 9   | 10 | 11 | 12 |
|---|----|----|----|-----|-----|-----|-----|-----|-----|----|----|----|
| a | c1 | c1 | c1 | c9  | c9  | c9  | d7  | d7  | d7  |    |    |    |
| b | c2 | c2 | c2 | c10 | c10 | c10 | d8  | d8  | d8  |    |    |    |
| c | c3 | c3 | c3 | d1  | d1  | d1  | d9  | d9  | d9  |    |    |    |
| d | c4 | c4 | c4 | d2  | d2  | d2  | d10 | d10 | d10 |    |    |    |
| e | c5 | c5 | c5 | d3  | d3  | d3  | mem | mem | mem |    |    |    |
| f | c6 | c6 | c6 | d4  | d4  | d4  | bl  | bl  | bl  |    |    |    |
| g | c7 | c7 | c7 | d5  | d5  | d5  | bl  | bl  | bl  |    |    |    |
| h | c8 | c8 | c8 | d6  | d6  | d6  | bl  | bl  | bl  |    |    |    |

Response Evaluation

The dose response of the cell cultures to carbon and helium beams irradiated at the midpoint inside the SOBP60 at 10 dose values (viz. 0 to 5 Gy) was assessed using Resazurin (alamarBlue), an established high-throughput cell viability assay, first at approximately 18 hours post-irradiation and then every 24 hours for 7 consecutive nights. The cell numbers per well were then quantified by measuring the fluorescence signal from each well (proportional to the number of cells) using an automated plate reader, and normalised to the signal from wells containing blank medium.

FIG. 14 is a plot of T98G cell proliferation (two flasks) over 1 week (168 hours), following 3 Gy irradiation with a carbon ion beam. FIG. 15 is a plot of T98G cell proliferation (two flasks) over 1 week (168 hours), incubated with 10B-BPA (black) and 157Gd-DOTA-TPP (gray) following 3 Gy irradiation with a carbon ion beam. FIG. 16 is a plot of T98G cell proliferation (two flasks) over 1 week (168 hours), following 3 Gy irradiation with a helium ion beam., while FIG. 17 is a plot of T98G cell proliferation over 1 week (168 hours), incubated with 10B-BPA (black) and 157Gd-DOTA-TPP (gray), following 3 Gy irradiation with a carbon ion beam.

FIGS. 18A to 18D are plots of cell proliferation (growth in viable number of cells) versus time (hours) post irradiation, up to a maximum of 7 days (168 hours) after irradiation, for cells irradiated with all 9 dose values of a carbon beam (viz. 0 to 5 Gy).

Figure 18A:
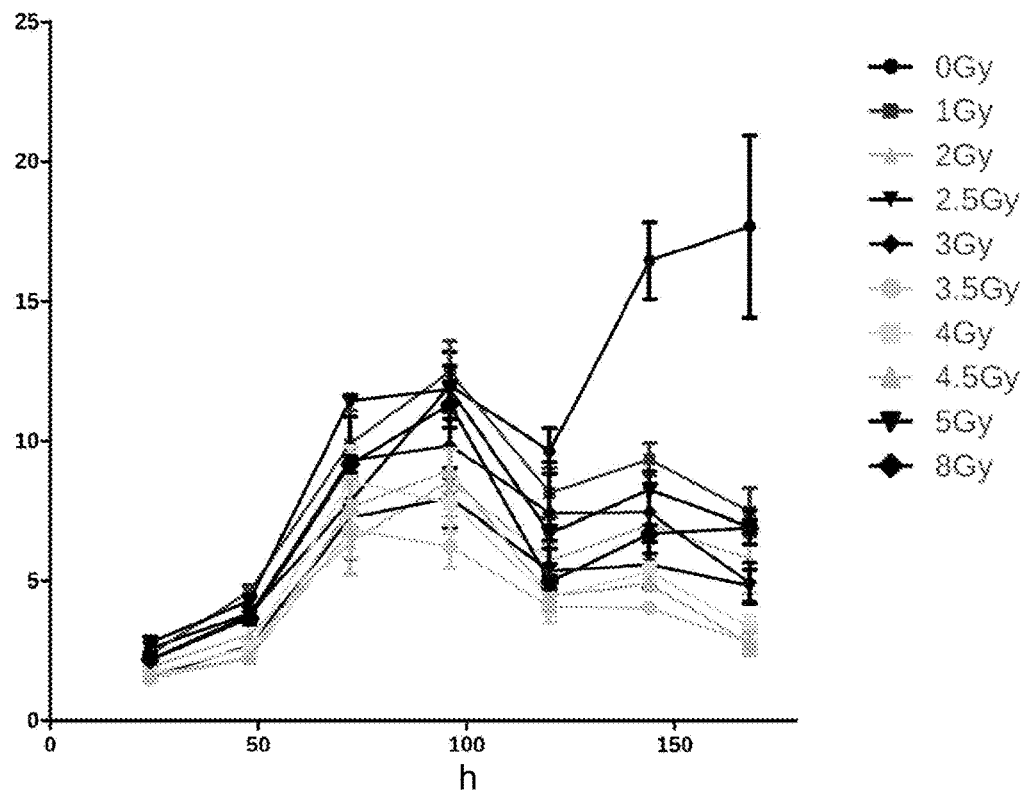
Figure 18B:
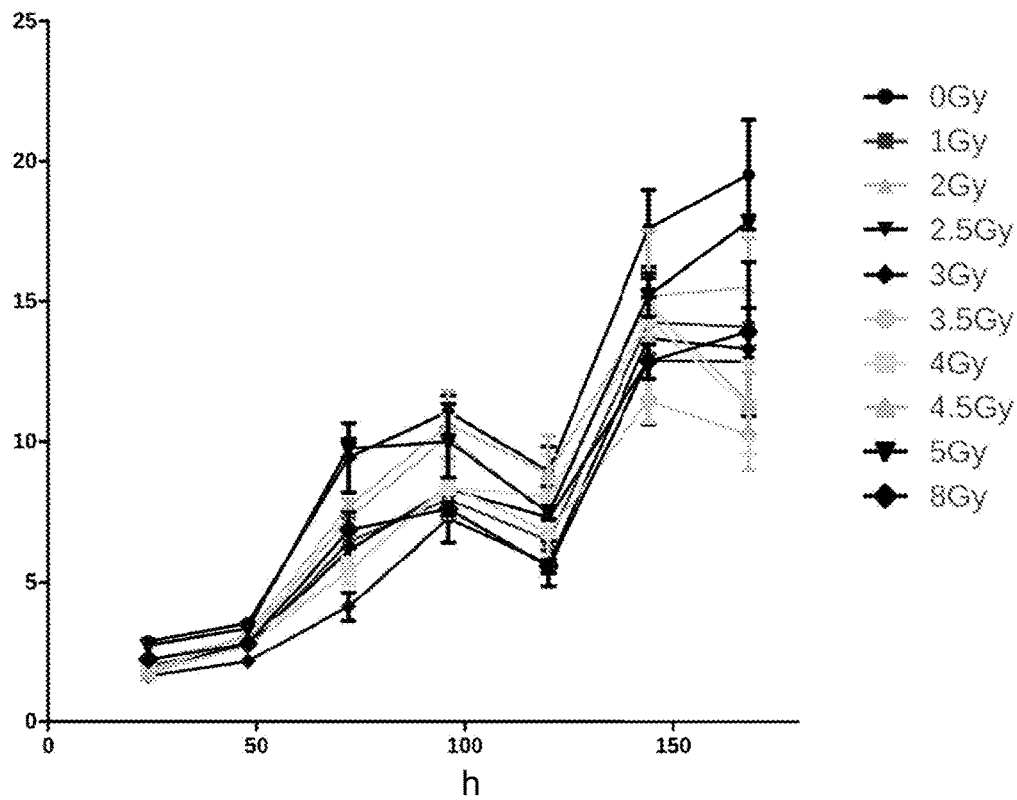
Figure 18C:
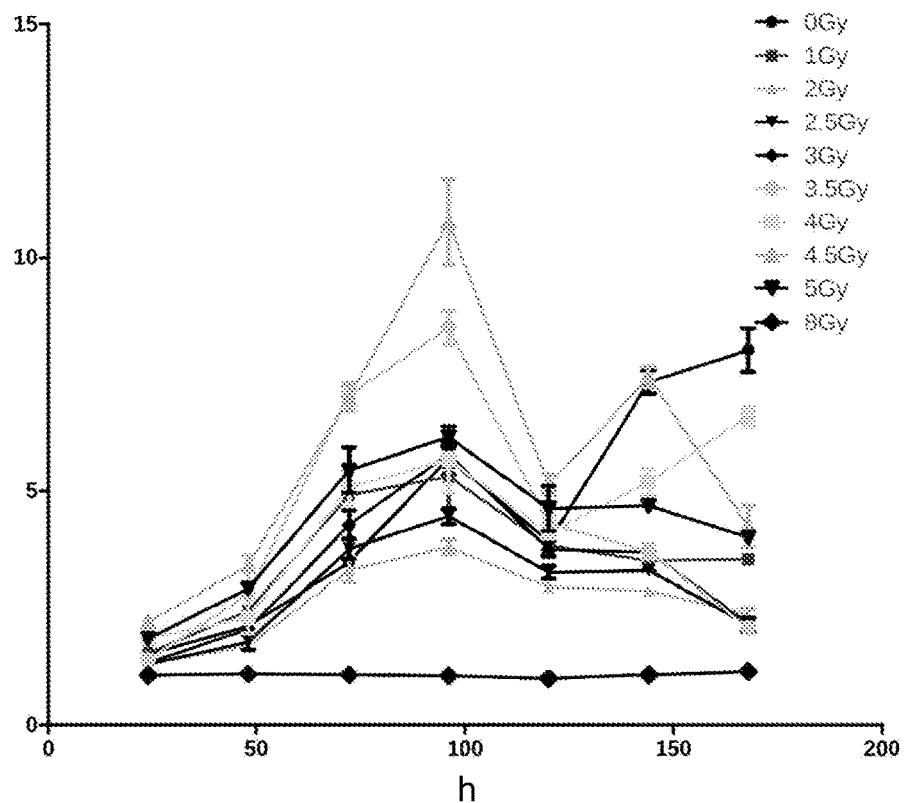
Figure 18D:
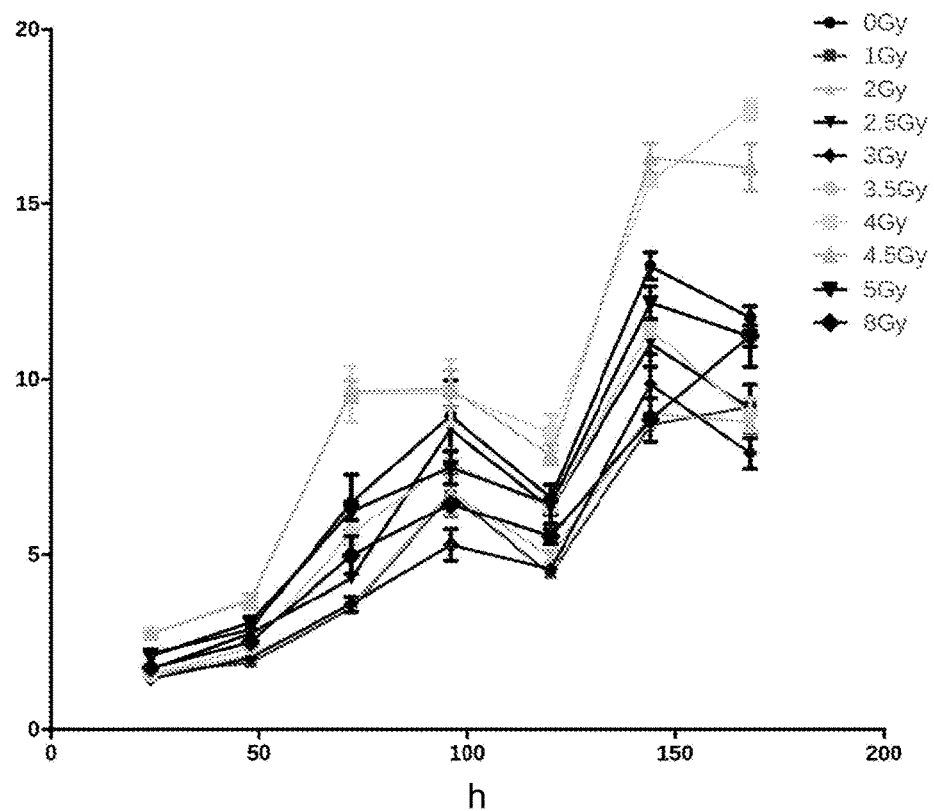

FIG. 18A corresponds to flasks containing cells which were incubated with the 10B neutron capture compound prior to irradiation, while FIG. 18B corresponds to flasks irradiated with the same dose values (0 to 5 Gy), in the absence of that neutron capture compound. FIG. 18C corresponds to flasks containing cells which were incubated with the 157Gd neutron capture compound prior to irradiation, while FIG. 18D corresponds to flasks irradiated with the same dose values (0 to 5 Gy), in the absence of that neutron capture compound. Cell proliferation is substantially reduced in those flasks incubated with a neutron capture compound prior to irradiation with the carbon beam.

FIGS. 19A to 19D are plots of cell proliferation (growth in viable number of cells) versus time (hours) post irradiation, up to a maximum of 7 days (168 hours) after irradiation, for cells irradiated with all 9 dose values of a helium beam (viz. 0 to 5 Gy).

Figure 19A:
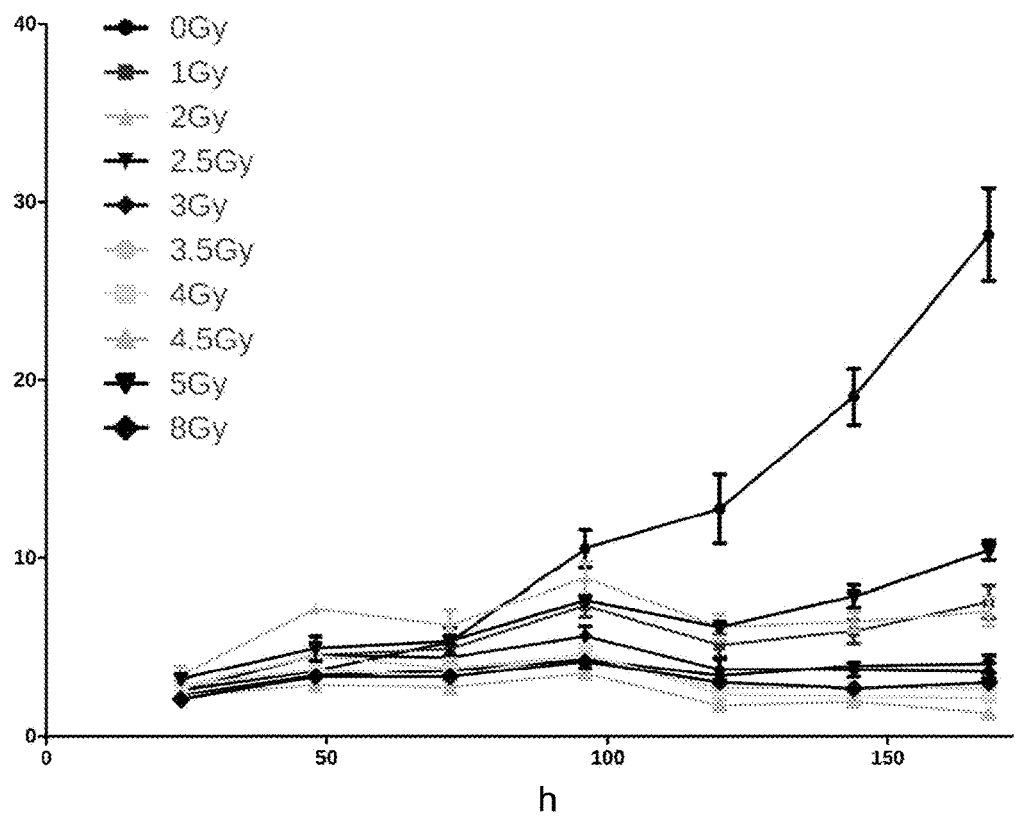
Figure 19B:
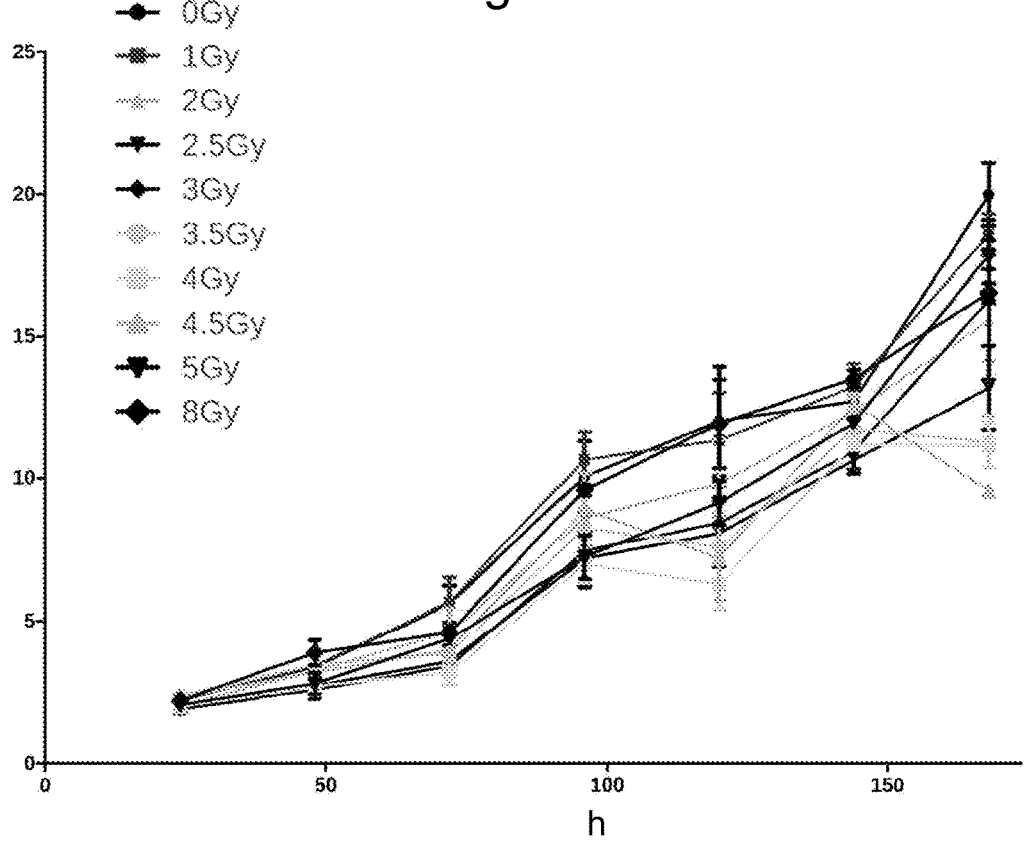
Figure 19C:
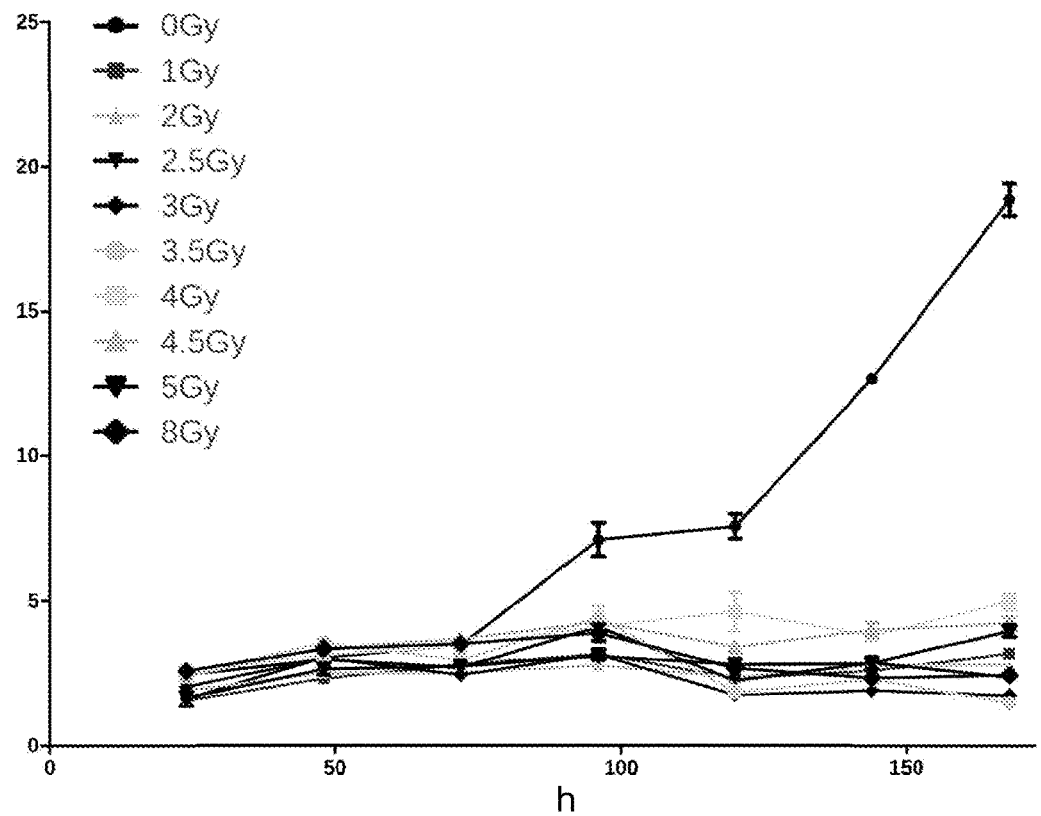
Figure 19D:
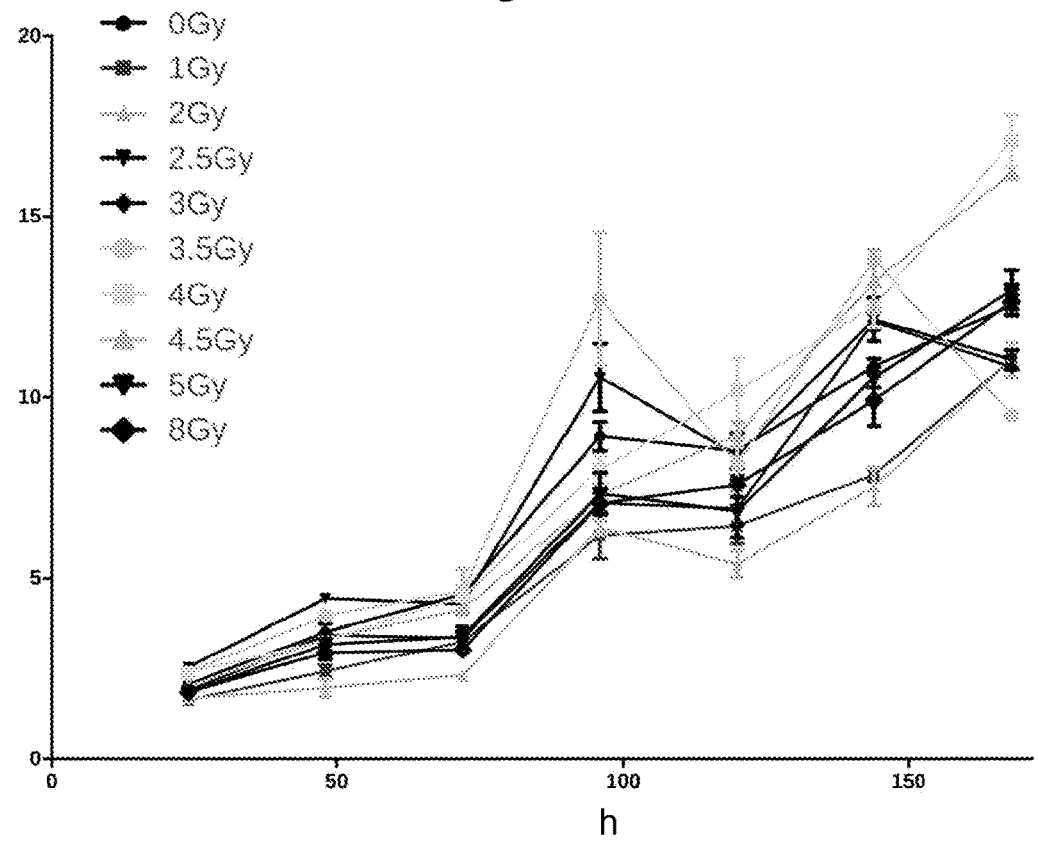
Figure 20A:
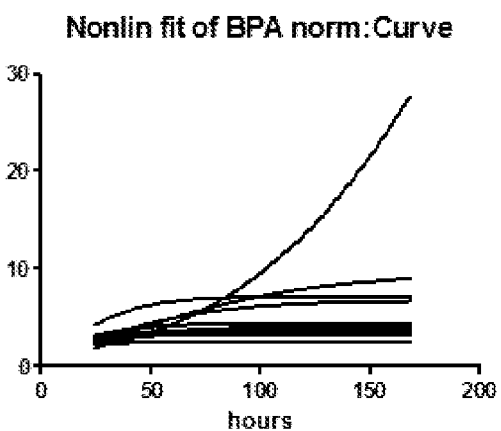
Figure 20C:
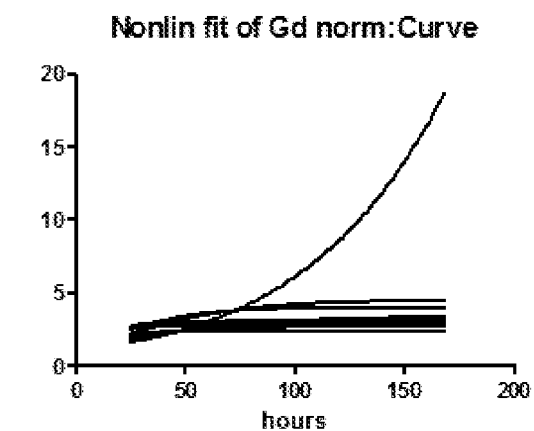
Figure 20B:
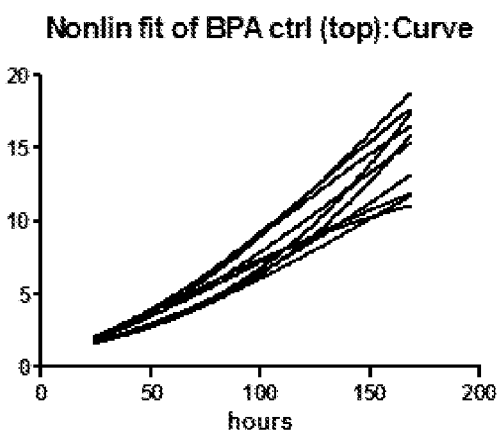
Figure 20D:
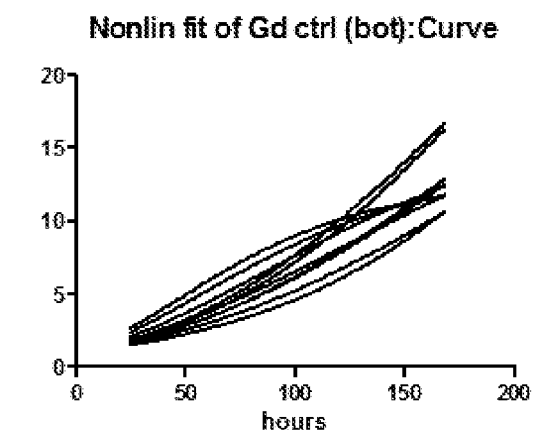

FIG. 19A corresponds to flasks containing cells which were incubated with the 10B neutron capture compound prior to irradiation, while FIG. 19B corresponds to flasks irradiated with the same dose values (0 to 5 Gy), in the absence of that neutron capture compound. FIG. 19C corresponds to flasks containing cells which were incubated with the 157Gd neutron capture compound prior to irradiation, while FIG. 19D corresponds to flasks irradiated with the same dose values (0 to 5 Gy), in the absence of that neutron capture compound. Cell proliferation is substantially reduced in those flasks incubated with a neutron capture compound prior and irradiated with the helium beam.

FIGS. 20A to 20D present the same data as that of FIGS. 19A to 19D (corresponding to the cells irradiated with the helium beam), respectively, but fitted with a growth model. These figures illustrate the cell proliferation (growth in viable number of cells) over 7 days post irradiation (i.e. 168 hours).

In summary, the analysis shows a clear and substantial radiosensitisation achieved by the introduction of the neutron capture agents ($^{10}$B-BPA and $^{157}$Gd-DOTA-TPP salt complex). The effect of all dose values on the control cell cultures (in the absence of neutron capture agents) is minimal. However, the cells treated with the $^{10}$B and $^{157}$Gd compounds show a reduction in proliferation rate by a factor of 4 to 5. Replication of these results in tumour-bearing animals and subsequently human patients is expected to result in achieving effective tumour control, at a fraction of the dose delivered by the primary particle beam. This is expected to result in a reduction of the normal tissue complications and unwanted side-effects of radiation on critical organs.

These results further support an additional hypothesis with regards to the impact of NCPET: its ability to target lesions adjacent or close to the target volume. In clinical particle therapy, tissue adjacent and close to the target volume receives 40 to 60% of the dose (the latter corresponding to organs in the path of the beam). The above results demonstrate that only a fraction of such a primary beam, with the addition of a neutron capture agent, can affect cell viability. Using neutron capture agents with high selectivity, it can be envisaged that a precise lethal dose can be targeted to malignant lesions at a cellular level.

REFERENCES

[1] L. Murray, A. Henry, P. Hoskin, F. Siebert, and J. Venselaar, "Second primary cancers after radiation for prostate cancer: A systematic review of the clinical data and impact of treatment technique," Radiother Oncol 110, 213-228 (2014).

[2] A. Gomez-Iturriaga, J. Cacicedo, A. Navarro, et al., "Incidence of pain flare following palliative radiotherapy for symptomatic bone metastases: multicenter prospective observational study," BMC Palliat Care 14, 48 (2015).

[3] T. Grantzau and J. Overgaard, "Risk of second non-breast cancer after radiotherapy for breast cancer: a systematic review and meta-analysis of 762,468 patients," Radiother Oncol 114, 56-65 (2015).

[4] S. Arcangeli, T. Zilli, B. D. Bari, and F. Alongi, "Hit the primary: A paradigm shift in the treatment of metastatic prostate cancer?" Crit Rev Oncol Hematol 97, 231-237 (2016).

[5] P. Blanchard, A. J. Wong, G. B. Gunn, et al., "Toward a model-based patient selection strategy for proton therapy: External validation of photon-derived normal tissue complication probability models in a head and neck proton therapy cohort," Radiother Oncol 121, 381-386 (2016).

[6] M. Durante, R. Orecchia, and J. S. Loeffler, "Charged-particle therapy in cancer: clinical uses and future perspectives," Nat Rev Clin Oncol (2017), 10.1038/nrclinonc.2017.30.

[7] S. L. Liauw, P. P. Connell, and R. R. Weichselbaum, "New paradigms and future challenges in radiation oncology: an update of biological targets and technology," Sci Transl Med 5, 173sr2 (2013).

[8] A. Wambersie, T. Auberger, R. A. Gahbauer, D. T. Jones, and R. Potter, "A challenge for high-precision radiation therapy: the case for hadrons," Strahlenther Onkol 175 Suppl 2, 122-128 (1999).

[9] M. Durante and H. Paganetti, "Nuclear physics in particle therapy: a review," Rep Prog Phys 79, 096702 (2016).

[10] G. Battistoni, I. Mattei, and S. Muraro, "Nuclear physics and particle therapy," Adv Phys X 1, 661-686 (2016).

[11] C. Zeitlin and C. L. Tessa, "The Role of Nuclear Fragmentation in Particle Therapy and Space Radiation Protection," Front Oncol 6, 65 (2016).

[12] S. H. Park and O. J. Kang, "Basics of particle therapy I: physics," Radiat Oncol J 29, 135-146 (2011).

[13] R. Barth, J. A. Coderre, M. G. H. Vicente, and T. H. Blue, "Boron neutron capture therapy of cancer: Current status and future prospects," Clin Cancer Res 11, 3987-4002 (2005).

[14] R. F. Barth, M. G. H. Vicente, O. K. Harling, et al., "Current status of boron neutron capture therapy of high grade gliomas and recurrent head and neck cancer," Radiat Oncol 7, 146 (2012).

[15] G. L. Locher, "Biological effects and therapeutic possibilities of neutrons," Am J Roentgenol Radi 36, 1-13 (1936).

[16] J. A. Coderre and G. M. Morris, "The radiation biology of boron neutron capture therapy," Radiat. Res. 151, 1-18 (1999).

[17] A. J. Coderre, J. C. Turcotte, K. J. Riley, P. J. Binns, 0. K. Harling, and W. S. Kiger, "Boron neutron capture therapy: cellular targeting of high linear energy transfer radiation," Technol. Cancer Res. Treat. 2, 355-375 (2003).

[18] E. Gonzalez and G. Hernandez, "An accelerator-based boron neutron capture therapy (bnct) facility based on the 7li(p,n)7be," Nucl Instrum Meth A (2016), http://dx.doi.org/10.1016/j.nima.2016.11.059.

[19] D. Kasatov, A. Koshkarev, A. Kuznetsov, et al., "The accelerator neutron source for boron neutron capture therapy," Journal of Physics: Conference Series 769, 012064 (2016).

[20] J. W. Hopewell, T. Gorlia, L. Pellettieri, V. Giusti, B. H-Stenstam, and K. Skold, "Boron neutron capture therapy for newly diagnosed glioblastoma multiforme: an assessment of clinical potential," Appl Radiat Isot 69, 1737-1740 (2011).

[21] S. Miyatake, S. Kawabata, R. Hiramatsu, et al., "Boron Neutron Capture Therapy for Malignant Brain Tumors," Neurol. Med. Chir. (Tokyo) 56, 361-371 (2016).

[22] IAEA, "Current status of neutron capture therapy," TECDOC 1223 (International Atomic Energy Agency, 2001).

[23] S. Agostinelli, J. Allison, K. Amako, et al., "Geant4—a simulation toolkit," Nucl Instrum Meth A 506, 250-303 (2003).

[24] J. Allison, K. Amako, J. Apostolakis, et al., "Geant4 developments and applications," IEEE T Nucl Sci 53, 270-278 (2006).

"Geant4 material database," Online: https://geant4.web.cern.ch/geant4/workAreaUserDocKA/Backup/Docbook_UsersGuides_beta/ForApplicationDeveloper/html/apas08.html (2016).

[26] M. Suzuki, Y. Sakurai, S. Masunaga, et al., "The effects of boron neutron capture therapy on liver tumors and normal hepatocytes in mice," Jpn J Clin Oncol 91, 1058-1064 (2000).

[27] M. Suzuki, Y. Sakurai, S. Masunaga, et al., "A preliminary experimental study of boron neutron capture therapy for malignant tumors spreading in thoracic cavity," Jpn J Clin Oncol 37, 245-249 (2007).

[28] IAEA, "Relative biological effectiveness in ion beam therapy," TECDOC 461 (International Atomic Energy Agency, 2008).

[29] R. Zamenohof, J. Brenner, J. Yanch, et al., "Treatment planning for neutron capture therapy of glioblastoma multiforme using an epithermal neutron beam from the Mitr-ii research reactor and monte carlo simulation," in Progress in Neutron Capture Therapy in Cancer, edited by B. Allen, B. Harrington, and D. Moore (Springer US, 1992) pp. 173-179.

[30] M. J. Luderer, P. de la Puente, and A. K. Azab, "Advancements in Tumor Targeting Strategies for Boron Neutron Capture Therapy," Pharm. Res. 32, 2824-2836 (2015). DOI https://doi.org/10.1007/s11095-015-1718-y.

[31] R. D. Alkins, P. M. Brodersen, R. N. Sodhi, and K. Hynynen, "Enhancing drug delivery for boron neutron capture therapy of brain tumors with focused ultrasound," Neuro-oncology 15, 1225-1235 (2013).

[32] H. Koganei, M. Ueno, S. Tachikawa, et al., "Development of high boron content liposomes and their promising antitumor effect for neutron capture therapy of cancers," Bioconjug Chem 24, 124-132 (2013).

[33] H. Joensuu, L. Kankaanranta, T. Seppala, et al., "Boron neutron capture therapy of brain tumors: clinical trials at the finnish facility using boronophenylalanine," J Neurooncol 62, 123-134 (2003).

[34] A. Z. Diaz, "Assessment of the results from the phase I/II boron neutron capture therapy trials at the Brookhaven National Laboratory from a clinician's point of view," J Neurooncol 62, 101-109 (2003).

[35] T. Hong, J. Wo, B. Yeap, et al., "Multi-Institutional Phase II Study of High-Dose Hypofractionated Proton Beam Therapy in Patients With Localized, Unresectable Hepatocellular Carcinoma and Intrahepatic Cholangiocarcinoma," J Clin Oncol 34, 460-468 (2016).

[36] C. Crane, "Hypofractionated ablative radiotherapy for locally advanced pancreatic cancer," J. Radiat. Res. 57 Suppl 1, i53-i57 (2016).

[37] A. Laine, A. Pompos, R. Timmerman, et al., "The Role of Hypofractionated Radiation Therapy with Photons, Protons, and Heavy Ions for Treating Extracranial Lesions," Front Oncol 5, 302 (2015).

[38] W. Sauerwein, "Neutron capture therapy," (Springer, 2012) Chap. Principles and Roots of Neutron Capture Therapy, pp. 1-16.

[39] Suzuki, M. et al. "Biodistribution of 10b in a rat liver tumor model following intra-arterial administration of sodium borocaptate (BSH)/degradable starch microspheres (DSM) emulsion," Appl. Radiat. Isot. 61, 933-937 (2004). URL https://doi.org/10.1016/j.apradiso.2004.05.014. DOI 10.1016/j.apradiso.2004.05.014.

[40] De Stasio, G. et al., "Gadolinium in Human Glioblastoma Cells for Gadolinium Neutron Capture Therapy". Cancer Res. 61, 4272-4277 (2001).

[41] Le, U. M. & Cui, Z., "Long-circulating gadolinium-encapsulated liposomes for potential application in tumor neutron capture therapy." Int. J. Pharm. 312, 105-112 (2006). URL https://doi.org/10.1016/j.ijpharm.2006.01.002. DOI 10.1016/j.ijpharm.2006.01.002.

[42] Peters, T. et al., "Cellular uptake and in vitro antitumor efficacy of composite liposomes for neutron capture therapy." Radiat. Oncol. 10, 52 (2015). URL https://doi.org/10.1186/s13014-015-0342-7. DOI 10.1186/s13014-015-0342-7.

[43] Ichikawa, H. et al., "Gadolinium-loaded chitosan nanoparticles for neutron-capture therapy: Influence of micrometric properties of the nanoparticles on tumor-killing effect." Appl. Radiat. Isot. 88, 109-113 (2014). URL https://doi. org/10.1016/j.apradiso.2013.12.018. DOI 10.1016/j.apradiso.2013.12.018.

[44] Tokumitsu, H. et al., "Gadolinium neutron-capture therapy using novel gadopentetic acid-chitosan complex nanoparticles: in vivo growth suppression of experimental melanoma solid tumor." Cancer Lett. 150, 177-182 (2000). URL https: //doi.org/10.1016/s0304-3835 (99) 00388-2. DOI 10.1016/s0304-3835 (99)00388-2.

[45] Morrison, D. E. et al., "High mitochondrial accumulation of new gadolinium(III) agents within tumour cells." Chem. Commun. 50,2252-2254 (2014).

[46] Capala, J., Coderre, J. & Chanana, A. A treatment planning comparison of bpa- or bsh-based bnct of malignant gliomas. Tech. Rep. BNL-64626, Brookhaven National Laboratories (1996).

[47] Morris, G. M. et al. Boron microlocalization in oral mucosal tissue: implications for boron neutron capture therapy. Br. J. Cancer 82,1764-1771 (2000). URL http://dx.doi.org/10.1054/bjoc.2000.1148. Regular Article.

[48] Fairlie, I. RBE and w(R) values of Auger emitters and low-range beta emitters with particular reference to tritium. J. Radiol. Prot. 27, 157-168 (2007).

[49] Humm, J. L., Howell, R. W. & Rao, D. V. Erratum: "Dosimetry of Auger electron-emitting-radionuclides: Report No. 3 of AAPM Nuclear Medicine Task Group No. 6" [Med. Phys. 21, 1901-1915 (1994)]. Med. Phys. 22, 1901-1915 (1995).

[50] Cerullo, N., Bufalino, D. & Daquino, G. Progress in the use of gadolinium for NCT. Appl. Radiat. Isot. 67, S157-160 (2009).

[51] Michiue, H. et al. The acceleration of boron neutron capture therapy using multi-linked mercap-toundecahy-drododecaborate (BSH) fused cell-penetrating peptide. Biomater. 35, 3396-3405 (2014). DOI https://doi.org/10.1016/j.biomaterials.2013.12.055.

[52] Nakamura, H. et al. Antitumor effect of boron nitride nanotubes in combination with thermal neutron irradiation on BNCT. Bioorganic & Medicinal Chem. Lett. 25, 172-174 (2015). DOI https://doi.org/10.1016/j.bmcl.2014.12.005.

[53]. Meyers, C. A. et al. Neurocognitive function and progression in patients with brain metastases treated with whole-brain radiation and motexafin gadolinium: results of a randomized phase III trial. J. Clin. Oncol. 22, 157-165 (2004).

[54]. De Stasio, G. et al. Motexafin-gadolinium taken up in vitro by at least 90% of glioblastoma cell nuclei. Clin. Cancer Res.12, 206-213 (2006).

[55]. Forouzannia, A., Richards, G. M., Khuntia, D. & Mehta, M. P. Motexafin gadolinium: a novel radiosensitizer for brain tumors. Expert. Rev. Anticancer. Ther. 7, 785-794 (2007).

[56]. Thomas, S. R. & Khuntia, D. Motexafin gadolinium: a promising radiation sensitizer in brain metastasis. Expert. Opin. Drug Discov. 6, 195-203 (2011). Modifications within the scope of the invention may be readily effected by those skilled in the art. It is to be understood, therefore, that this invention is not limited to the particular embodiments described by way of example hereinabove.

In the claims that follow and in the preceding description of the invention, except where the context requires otherwise owing to express language or necessary implication, the word "comprise" or variations such as "comprises" or "comprising" is used in an inclusive sense, that is, to specify the presence of the stated features but not to preclude the presence or addition of further features in various embodiments of the invention.

Further, any reference herein to prior art is not intended to imply that such prior art forms or formed a part of the common general knowledge in any country.

The invention claimed is:

1. An irradiation method for irradiating a target volume of a subject, the method comprising:
   providing thermal neutron absorbing nuclides in or adjacent to the target volume of the subject, in the absence of a separate proton-absorbing substance provided to the subject; and
   producing neutrons by irradiating nuclei with a beam of particles consisting of any one or more of protons, deuterons, tritons or heavy ions, thereby prompting production of the neutrons in the subject through non-elastic collisions within the subject between the nuclei and the particles;
   wherein the neutron absorbing nuclides absorb neutrons produced in the non-elastic collisions, thereby producing capture products or fragments that irradiate the target volume.

2. The method as claimed in claim 1, further comprising configuring the beam of particles so as also to irradiate the target volume.

3. The method as claimed in claim 1, wherein the beam comprises protons, $^4$He, $^{10}$C, $^{11}$C, $^{12}$C, $^{15}$O, $^{16}$O, highly energetic protons or heavy ions.

4. The method as claimed in claim 1, further comprising providing the thermal neutron absorbing nuclides in the form of a composition containing $^{10}$B or $^{157}$Gd.

5. The method as claimed in claim 1, wherein the composition is preferentially absorbed by a malignant target tissue.

6. The method as claimed in claim 1, wherein the capture products or fragments comprise energetic charged particles of high relative biological effectiveness or other energetic charged particles.

7. A method of irradiating biological tissue using a proton, deuteron, triton or heavy ion beam, the method comprising irradiating a target volume that includes the biological tissue according to the method of claim 1.

8. The method as claimed in claim 1, wherein the beam of particles has a Bragg peak that is outside the subject.

9. A method of inhibiting growth of any one or more of a tumour, satellite lesion or metastatic lesion of a subject, the method comprising:
- dosing the tumour, satellite lesion or metastatic lesion with a composition comprising thermal neutron absorbing nuclides, in the absence of a separate proton-absorbing substance provided to the subject; and
- irradiating nuclei in the subject with a beam of particles consisting of any one or more of protons, deuterons, tritons or heavy ions, thereby producing neutrons in the subject through non-elastic collisions within the subject between the nuclei and the particles;
- wherein the neutron absorbing nuclides absorb neutrons produced in the non-elastic collisions, thereby producing capture products or fragments that irradiate the tumour, satellite lesion or metastatic lesion.

10. The method as claimed in claim 9, wherein the beam comprises protons, $^4$He, $^{10}$C, $^{11}$C, $^{12}$C, $^{15}$O, $^{16}$O, highly energetic protons or heavy ions.

11. The method as claimed in claim 9, further comprising providing the thermal neutron absorbing nuclides in the form of a composition containing $^{10}$B or $^{157}$Gd.

12. The method as claimed in claim 11, wherein the composition is preferentially absorbed by the tumour, satellite lesion or intracranial metastatic lesion.

13. The method as claimed in claim 9, wherein the capture products or fragments comprise energetic charged particles of high relative biological effectiveness or other energetic charged particles.

14. The method as claimed in claim 9, wherein said beam irradiates matter along its path in a spot scanning manner, a uniform scanning manner, a fast scanning manner, raster scanning manner, or a passively scattered manner.

15. The method as claimed in claim 9, wherein the beam has a Bragg peak that is outside the subject.

16. A computer-implemented method of determining parameters for particle therapy of a subject, the method comprising:
- modelling or simulating, based on a set of default or selected parameters:
  - a) irradiation of nuclei in the subject with a beam of primary particles consisting of any one or more of protons, deuterons, tritons or heavy ions;
  - b) production of neutrons in the subject through non-elastic collisions within the subject between the nuclei in or adjacent to the target volume and the primary particles, in the absence of a separate proton-absorbing substance provided to the subject; and
  - c) production of capture products or fragments released as a result of the neutron capture and nuclear reactions between at least one high neutron cross section agent located in or adjacent to a target volume and the thermal neutrons produced from the non-elastic collisions within the subject between the nuclei and the primary particles;
- determining a difference between the production of the capture products or fragments with either (i) a predetermined template or desired production of the capture products or fragments, or (ii) empirical reaction validation data; and
- generating a modified set of parameters according to the difference.

17. The method as claimed in claim 16, wherein the modelling further comprises:
- modelling irradiation of a tumour or a portion thereof, one or more satellite lesions or one or more metastatic lesions, or other tissue, within or adjacent to the target volume by the capture products or fragments; or
- locating a composition comprising the thermal neutron absorbing nuclides in the target volume; or
- modelling or simulating the target volume as PMMA (poly(methyl methacrylate)) or other tissue equivalent material.

18. The method as claimed in claim 16, wherein the parameters comprise any one or more of:
- i) duration of the irradiation;
- ii) composition of the beam;
- iii) energy of the particles of the beam;
- iv) peak radiobiological effectiveness of the particles of the beam;
- v) physical dose deposition of the particles of the beam;
- vi) the composition that comprises thermal neutron absorbing nuclides;
- vii) concentration of the composition that comprises thermal neutron absorbing nuclides;
- viii) spatial distribution of the composition that comprises thermal neutron absorbing nuclides;
- ix) fluence of the neutrons produced in the subject through the non-elastic collisions;
- x) target volume position relative to the beam; or
- xi) ion specific radiobiological efficacy.

19. The method as claimed in claim 16, further comprising modelling or simulating the beam so as to have a Bragg peak that is outside of the subject.

20. A non-transitory computer-readable medium, comprising computer software configured to, when executed by one or more processors, implement the method of determining parameters for particle therapy according to claim 16.

21. A control system for controlling an irradiation system, wherein:
- the irradiation system provides a particle beam of accelerated particles comprising any one or more of protons, deuterons, tritons or heavy ions; and
- the control system includes or is configured to access an irradiation program for implementing a predetermined irradiation of a target volume, the predetermined irradiation comprising:
- irradiating nuclei of a subject with the particle beam, thereby prompting production of neutrons in the subject through non-elastic collisions within the subject between the nuclei and the particles, whereby thermal neutron absorbing nuclides provided before irradiation at or adjacent to the target volume, in the absence of a separate proton-absorbing substance provided to the subject, absorb neutrons produced in the non-elastic collisions, thereby producing capture products or fragments that irradiate the target volume.

22. The control system as claimed in claim 21, comprising:
- a particle supply controller configured to control a particle source of the irradiation system, the particle source supplying the particles;

an accelerator controller configured to control an accelerator of the irradiation system, the accelerator providing the particle beam by accelerating the particles;

a beam steerer for controlling one or more beam steering units configured to direct the particle beam; and an extraction controller for controlling extraction of the accelerated particles from the accelerator.

23. The control system as claimed in claim 21, further comprising a treatment planning system (TPS) configured to determine the irradiation program.

24. The control system as claimed in claim 21, wherein the control system is operable so that the beam has a Bragg peak that is outside the subject.

25. An irradiation system, comprising:

a particle source for supplying primary particles comprising any one or more of protons, deuterons, tritons or heavy ions;

an accelerator for providing a particle beam by accelerating the particles;

an extraction beamline for extracting the particle beam from the accelerator;

one or more beam steering units configured to direct the particle beam; and a control system as claimed in claim 21.

26. The irradiation system as claimed in claim 25, wherein the irradiation program, or a set of parameters employed thereby, is adapted or personalized for a specific target volume or subject.

* * * * *

UNITED STATES PATENT AND TRADEMARK OFFICE
CERTIFICATE OF CORRECTION

| | |
|---|---|
| PATENT NO. | : 11,850,449 B2 |
| APPLICATION NO. | : 16/644368 |
| DATED | : December 26, 2023 |
| INVENTOR(S) | : Mitra Safavi-Naeini |

It is certified that error appears in the above-identified patent and that said Letters Patent is hereby corrected as shown below:

On the Title Page

On Page 3, Column 1, Line 1, item (56) under Other Publications, delete ""Dosimtery" and insert --Dosimetry--.

In the Specification

In Column 1, Line 37, delete "targetting" and insert --targeting--.

In Column 5, Line 29, delete "$^6$He," and insert --$^5$He,--.

In Column 15, Line 64, delete "2k" and insert --$2^k$--.

In Column 16, Line 8 (Approx.), delete "ofthermal" and insert --of thermal--.

In Column 17, Line 7, delete "(Nth)" and insert --($N_{th}$)--.

In Column 18, Line 11, TABLE III, delete "lipidol" and insert --lipiodol--.

In Column 24, Line 3, delete "gadoliniumbearing" and insert --gadolinium-bearing--.

In Column 28, Line 19 (Approx.), delete "biologica1" and insert --biological--.

In Column 37, Lines 64-65, delete "mercap-toundecahydrododecaborate" and insert --mercaptoundecahydrododecaborate--.

Signed and Sealed this
Thirtieth Day of April, 2024

Katherine Kelly Vidal
*Director of the United States Patent and Trademark Office*